(12) United States Patent
Griffith et al.

(10) Patent No.: US 6,197,575 B1
(45) Date of Patent: Mar. 6, 2001

(54) VASCULARIZED PERFUSED MICROTISSUE/ MICRO-ORGAN ARRAYS

(75) Inventors: Linda G. Griffith, Cambridge; Steven Tannenbaum, Framingham; Mark J. Powers, Cambridge; Karel Domansky, Cambridge; Charles D. Thompson, Cambridge, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/272,227

(22) Filed: Mar. 18, 1999

Related U.S. Application Data
(60) Provisional application No. 60/078,452, filed on Mar. 18, 1998.

(51) Int. Cl.[7] ............................... C12M 1/34; C12M 3/00
(52) U.S. Cl. .................... 435/288.4; 435/288.7; 435/297.5; 435/305.2; 435/33; 435/373; 435/395
(58) Field of Search .................. 435/1.1, 1.2, 29, 435/32, 33, 284.1, 287.1, 395, 401, 288.3, 402, 288.4, 373, 288.5, 288.7, 297.2, 297.5, 305.1, 305.2, DIG. 6, DIG. 43–45, DIG. 47

(56) References Cited

U.S. PATENT DOCUMENTS

| | | |
|---|---|---|
| 4,060,081 | 11/1977 | Yannas et al. . |
| 4,485,096 | 11/1984 | Bell . |
| 4,485,097 | 11/1984 | Bell . |
| 4,520,821 | 6/1985 | Schmidt et al. . |
| 4,539,716 | 9/1985 | Bell . |

(List continued on next page.)

FOREIGN PATENT DOCUMENTS

| | | |
|---|---|---|
| 0 363 262 A1 | 4/1990 | (EP) . |
| 0 455 508 A1 | 11/1991 | (EP) . |

(List continued on next page.)

OTHER PUBLICATIONS

Arias, et al., eds., *The Liver*, Raven Press:New York, NY, 1988.

Bain, et al., "Embryonic stem cells express neuronal properties in vitro," *Dev. Biol.* 168(2):342–57 (1995).

(List continued on next page.)

*Primary Examiner*—William H. Beisner
(74) *Attorney, Agent, or Firm*—Arnall Golden & Gregory, LLP

(57) ABSTRACT

Systems including (1) a micromatrix and perfusion assembly suitable for seeding and attachment of cells within the matrix and for morphogenesis of seeded cells into complex, hierarchical tissue or organ structures, wherein the matrix includes channels or vessels through which culture medium, oxygen, or other nutrient or body fluids can be perfused while controlling gradients of nutrients and exogenous metabolites throughout the perfusion path independently of perfusion rate, and (2) sensor means for detecting changes in either cells within the matrix or in materials exposed to the cells, have been developed. Methods for making the micromatrices include micromachining, micromolding, embossing, laser drilling, and electro deposition machining. Cells can be of one or more types, either differentiated or undifferentiated. In a preferred embodiment, the matrix is seeded with a mixture of cells including endothelial cells which will line the channels to form "blood vessels", and at least one type of parenchymal cells, such as hepatocytes, pancreatic cells, or other organ cells. The system can be used to screen materials for an effect on the cells, for an effect of the cells on the materials (for example, in a manner equivalent to tissue metabolism of a drug), or to test a material on a biological that must first infect cells or tissues, such as viruses. The apparatus also can be used to provide a physiological environment for expansion of stem cells, or for enabling gene therapy in vitro.

28 Claims, 16 Drawing Sheets

U.S. PATENT DOCUMENTS

| | | |
|---|---|---|
| 4,546,500 | 10/1985 | Bell . |
| 4,729,949 * | 3/1988 | Weinreb et al. . |
| 4,734,372 * | 3/1988 | Rotman . |
| 4,894,343 * | 1/1990 | Tanaka et al. . |
| 5,153,132 | 10/1992 | Goodwin et al. . |
| 5,169,601 * | 12/1992 | Ohta et al. . |
| 5,190,878 | 3/1993 | Wilhelm . |
| 5,204,055 | 4/1993 | Sachs et al. . |
| 5,424,209 | 6/1995 | Kearney . |
| 5,443,950 | 8/1995 | Naughton et al. . |
| 5,451,524 | 9/1995 | Coble et al. . |
| 5,459,069 * | 10/1995 | Palsson et al. . |
| 5,510,254 | 4/1996 | Naughton et al. . |
| 5,512,474 | 4/1996 | Clapper et al. . |
| 5,518,680 | 5/1996 | Cima et al. . |
| 5,559,022 | 9/1996 | Naughton et al. . |
| 5,595,909 | 1/1997 | Hu et al. . |
| 5,599,788 | 2/1997 | Purchio et al. . |
| 5,602,026 | 2/1997 | Dunn et al. . |
| 5,602,028 * | 2/1997 | Minchinton . |
| 5,602,029 | 2/1997 | Miyamoto . |
| 5,605,835 | 2/1997 | Hu et al. . |
| 5,612,188 | 3/1997 | Shuler, et al. . |
| 5,624,840 | 4/1997 | Naughton et al. . |
| 5,650,323 | 7/1997 | Root . |
| 5,658,797 | 8/1997 | Bader . |
| 5,674,742 | 10/1997 | Northup et al. . |
| 5,700,688 | 12/1997 | Lee et al. . |
| 5,843,767 * | 12/1998 | Beattie . |
| 6,015,674 * | 1/2000 | Woudenberg et al. . |
| 6,037,171 * | 3/2000 | Larsson ............................ 435/297.1 |

FOREIGN PATENT DOCUMENTS

| | | |
|---|---|---|
| 0 539 888 A1 | 5/1993 | (EP) . |
| 0 870 823 A1 | 10/1998 | (EP) . |
| 04278080 | 2/1992 | (JP) . |
| 04262780 | 9/1992 | (JP) . |
| 8-154663 * | 6/1996 | (JP) . |
| WO 90/04645 A1 | 5/1990 | (WO) . |
| WO 95/24464 A1 | 9/1995 | (WO) . |
| WO 96/34087 A1 | 4/1996 | (WO) . |
| WO 96/40002 A1 | 12/1996 | (WO) . |
| 97/153394 * | 5/1997 | (WO) . |

OTHER PUBLICATIONS

Block, et al., "Population expansion, clonal growth, and specific differentiation patterns in primary cultures of hepatocytes induced by HGF/SF, EGF and TGF alpha in a chemically defined (HGM) medium," *J. Cell Biol.* 132(6):1133–49 (1996).

Brandup & Immergut, *The Polymer Handbook*, 3rd edition, Wiley:N.Y., 1989.

Cima, et al., "Tissue Engineering by Cell Transplantation Using Degradable Polymer Substrates," *J. Biomechan. Eng.* 113:143–51 (1991).

Cima, et al., "A theoretical and experimental evaluation of a novel radial–flow hollow fiber reactor for mammalian cell culture," *Bioprocess Eng.* 5:19–30 (1990).

Cima, et al., "Hepatocyte culture on biodegradable polymeric substrates," *Biotech. Bioeng.* 38:145–58 (1991).

Denk, et al., "Two–photon laser scanning fluorescence microscopy," *Science.* 248(4951):73–6 (1990).

Dhadwal, et al., "Effects of anatomic variability on blood flow and pressure gradients in the pulmonary capillaries," *J Appl Physiol.* 83(5):1711–20 (1997).

Dimilla, et al., "Maximal migration of human smooth muscle cells on fibronectin and type IV collagen occurs at an intermediate attachment strength," *J Cell Biol.* 122(3):729–37 (1993).

Doetschman, et al., "The in vitro development of blastocyst–derived embryonic stem cell lines: formation of visceral yolk sac, blood islands and myocardium," *J Embryol Exp Morphol.* 87:27–45 (1985).

Doktycz, et al., "Genosensors and Model Hybridization Studies" in *Automation Technologies for Genome Characterization*, T.J. Beugelsdijk, ed. (John Wiley & Sons, New York 1997).

Encke, et al., "Genetic immunization generates cellular and humoral immune responses against the nonstructural proteins of the hepatitis C virus in a murine model," *J Immunol.* 161(9):4917–23 (1998).

Fontaine, et al., "Human hepatocyte isolation and transplantation into an athymic rat, using prevascularized cell polymer constructs," *J Pediatr Surg.* 30(1):56–60 (1995).

Geissler, et al., "Enhancement of cellular and humoral immune responses to hepatitis C virus core protein using DNA–based vaccines augmented with cytokine–expressing plasmids," *J Immunol.* 158(3):1231–7 (1997).

Gendron, et al., "Induction of embryonic vasculogenesis by bFGF and LIF in vitro and in vivo," *Dev Biol.* 177(1):332–46 (1996).

Griffith, et al., "In vitro organogenesis of vascularized liver tissue," *Ann. N.Y.Acad. Sci.*, 831:382–97 (1997).

Ingber, et al., "Mechanochemical Switching Between Growth Factor–Stimulated Angiogenesis In Vitro: Role of Extracellular Matrix," *J. Cell. Biol.*, 109:317–330 (1989).

Irvine, et al., "Comparison of tethered star and linear poly(ethylene oxide) for control of biomaterials surface properties," *J Biomed Mater Res.* 40(3):498–509 (1998).

Irvine, et al., "Self–consistent field analysis of grafted star polymers," *Macromolecules* 29:6037–43 (1996).

Kennedy, et al., "A common precursor for primitive erythropoiesis and definitive haematopoiesis," *Nature.* 386(6624):488–93 (1997).

Kuhl & Griffith–Cima, "Tethered epidermal growth factor as a paradigm for growth factor–induced stimulation from the solid phase," *Nat Med.* 2(9):1022–7 (1996).

Lautt, et al., "Hepatic circulation and toxicology," *Drug Metab Rev.* 29(1–2):369–95 (1997).

Lee & Laibinis, "Protein–resistant coatings for glass and metal oxide surfaces derived from oligo(ethylene glycol)–terminated alkyltrichlorosilanes," *Biomaterials.* 19(18):1669–75 (1998).

Lee, et al., "Protein–resistant surfaces prepared by PEO–containing block copolymer surfactants," *J. Biomed. Mat. Res,* 23:351–68 (1989).

Li, et al., "Characterization of a 120–Kilodalton pre–S–binding protein as a candidate duck hepatitis B virus receptor," *J Virol.* 70(9):6029–35 (1996).

Liang, et al., "Rapid identification of low level hepatitis B–related viral genome in serum," *J Clin Invest.* 84(4):1367–71 (1989).

Masters, et al., "Multiphoton excitation fluorescence microscopy and spectroscopy of In Vivo human skin," *Biophys. J.* 72:2405–12 (1996).

Melegari, et al., "The small envelope protein is required for secretion of a naturally occurring hepatitis B virus mutant with pre–S1 deleted," *J Virol.* 71(7):5449–54 (1997).

Millauer, et al., "High affinity VEGF binding and developmental expression suggest Flk–1 as a major regulator of vasculogenesis and angiogenesis," *Cell.* 72(6):835–46 (1993).

Mooney, "Switching from Differentiation to Growth in Hepatocytes: Control by Extracellular Matrix," *J. Cell. Phys.* (151):497–505 (1992).

Moradpour, et al., "Specific targeting of human hepatocellular carcinoma cells by immunoliposomes in vitro," Hepatology. 22(5):1527–37 (1995).

Moradpour, et al., "Understanding hepatitis B virus infection," *N Engl J Med.* 332(16):1092–3 (1995).

Powers, et al., "Cell–substratum adhesion strength as a determinant of hepatocyte aggregate morphology," *Biotech. Bioeng.* 53:415–26 (1997).

Reddy, et al., "Proliferative response of fibroblasts expressing internalization–deficient epidermal growth factor (EGF) receptors is altered via differential EGF depletion effect," *Biotechnol Prog.* 10(4):377–84 (1994).

Sachs, et al., "CAD–Casting: Direct Fabrication of Ceramic Shells and Cores by Three Dimensional Printing," *Manufacturing Review* 5(2):117–26 (1992).

Saito, et al., "Molecular cloning of a murine IL–6 receptor–associated signal transducer, gp130, and its regulated expression in vivo," *J Immunol.* 148(12):4066–71 (1992).

Scaglioni, et al., "Posttranscriptional regulation of hepatitis B virus replication by the precore protein," *J Virol.* 71(1):345–53 (1997).

Steinberg, et al., "Experimental specification of cell sorting, tissue spreading, and specific spatial patterning by quantitative differences in cadherin expression," *Proc Natl Acad Sci U S A.* 91(1):206–9 (1994).

Tatarowicz, et al.,. "Repression of the HSV–1 latency–associated transcript (LAT) promoter by the early growth response (EGR) proteins: involvement of a binding site immediately downstream of the TATA box," *J Neurovirol.* 3(3):212–24 (1997).

Tesh & O'Brien, "The pathogenic mechanisms of Shiga toxin and the Shiga–like toxins," *Mol Microbiol.* 5(8):1817–22 (1991).

Vacanti, et al., "Beyond Transplantation," *Arch. Surg.* 123:545–49 (1988).

Wakita, et al., "Specific inhibition of hepatitis C virus expression by antisense oligodeoxynucleotides. In vitro model for selection of target sequence," *J Biol Chem.* 269(19):14205–10 (1994).

Wallis & Pomerantz, "Field assisted glass–metal sealing," *J. Appl. Physics* 40:3946–3949 (1969).

Walton, et al., "Creation of stable poly(ethylene oxide) surfaces on poly(methyl methacrylate) using blends of branched and linear polymers," *Macromolecules* 30:6947–56 (1997).

Williams, et al., "Myeloid leukaemia inhibitory factor maintains the developmental potential of embryonic stem cells," *Nature.* 336(6200):684–7 (1988).

Yoo, et al., "Regulation of transforming growth factor–beta 1 expression by the hepatitis B virus (HBV) X transactivator. Role in HBV pathogenesis," *J Clin Invest.* 97(2):388–95 (1996).

Zlokarnik, et al., "Quantitation of transcription and clonal selection of single living cells with beta–lactamase as reporter," *Science.* 279(5347):84–8 (1998).

\* cited by examiner

REACTOR DURING CELL SEEDING

REACTOR OPERATING IN FORCED FLOW MODE

REACTOR OPERATING IN CROSS FLOW MODE

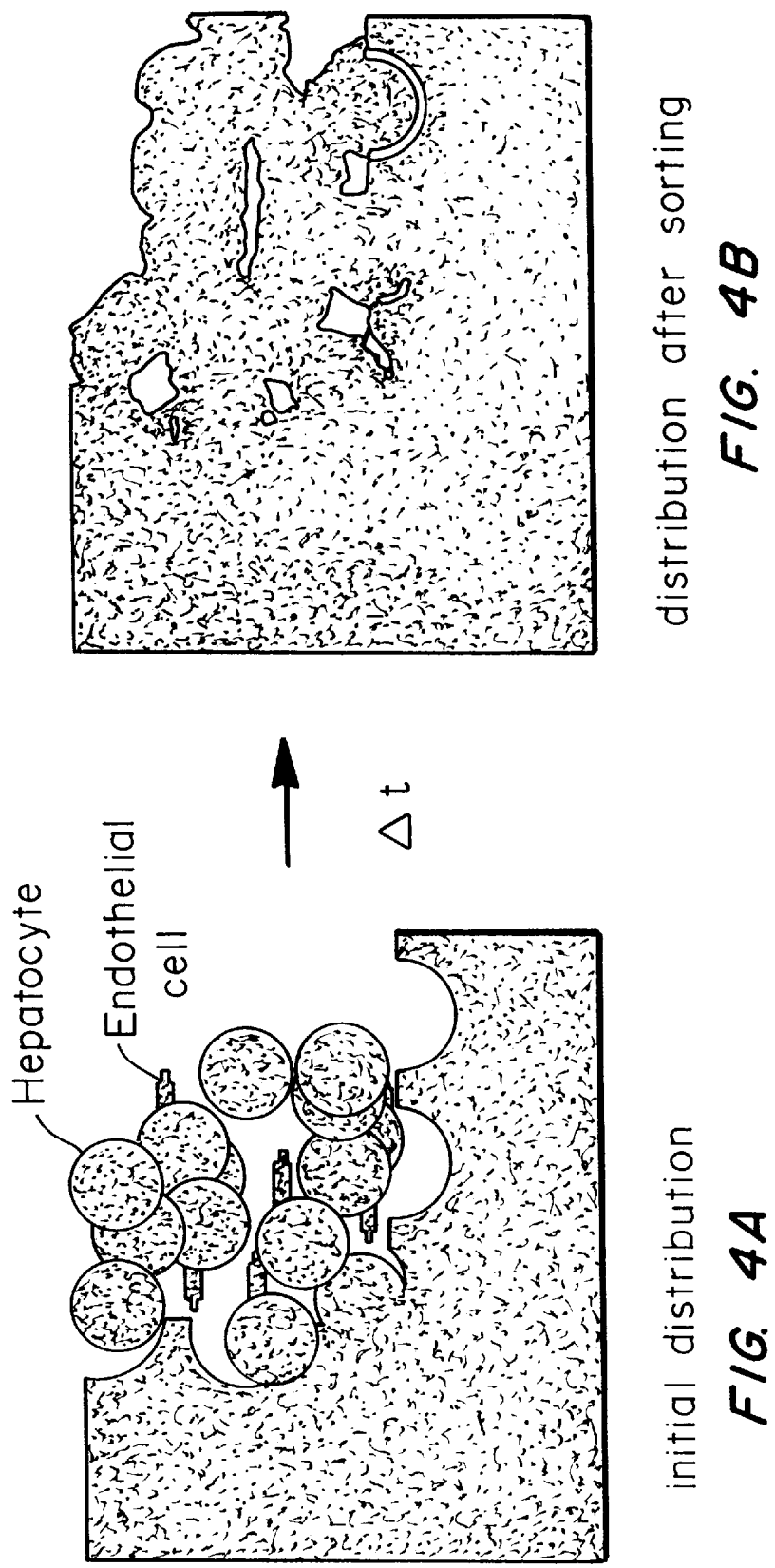

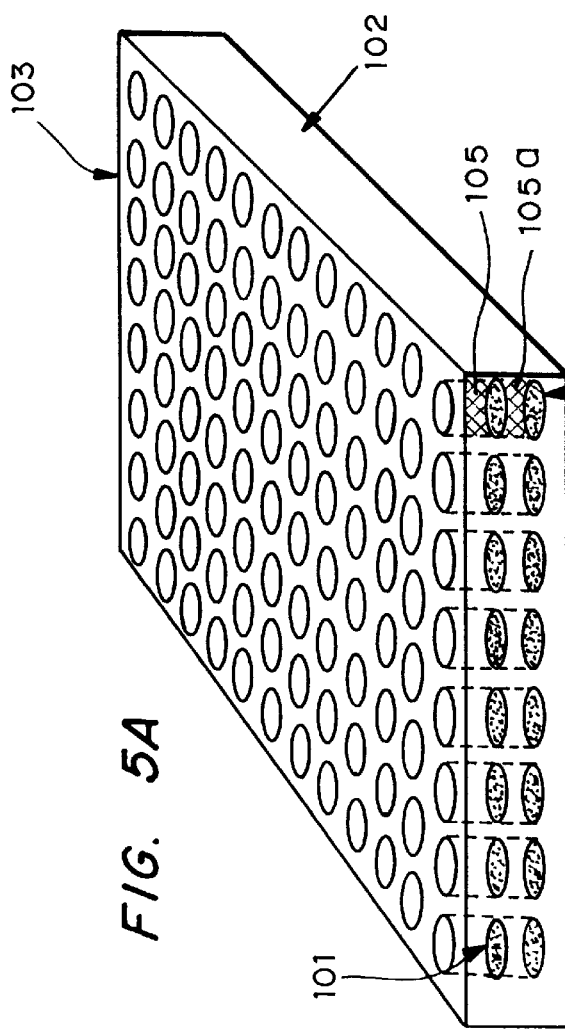
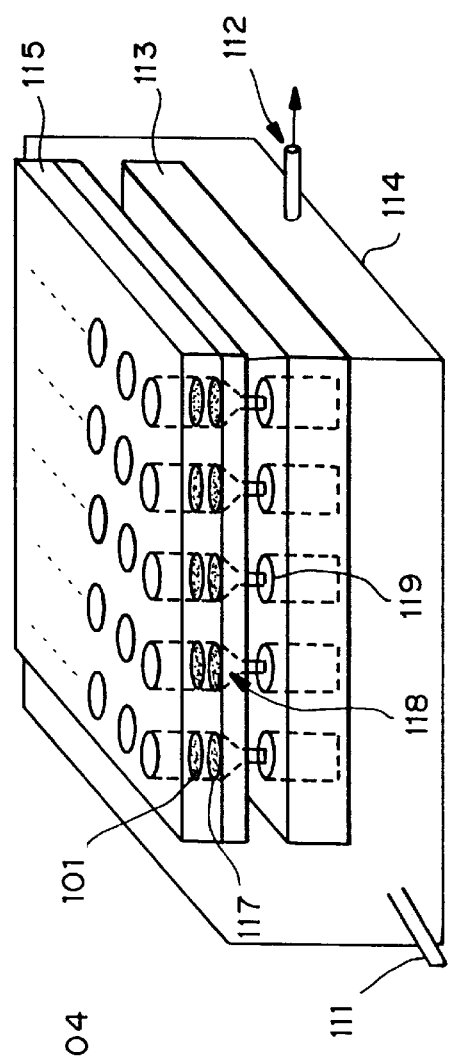

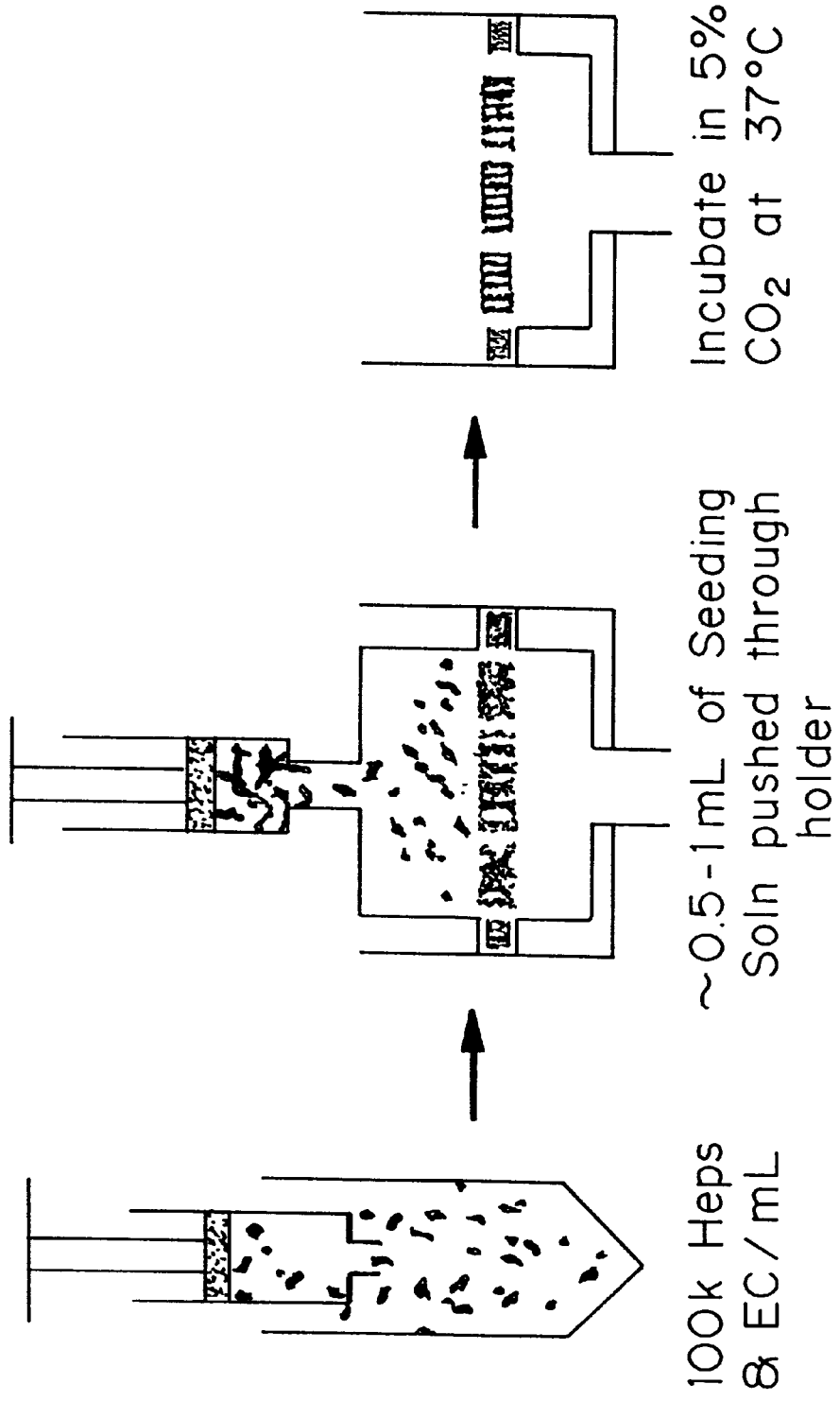

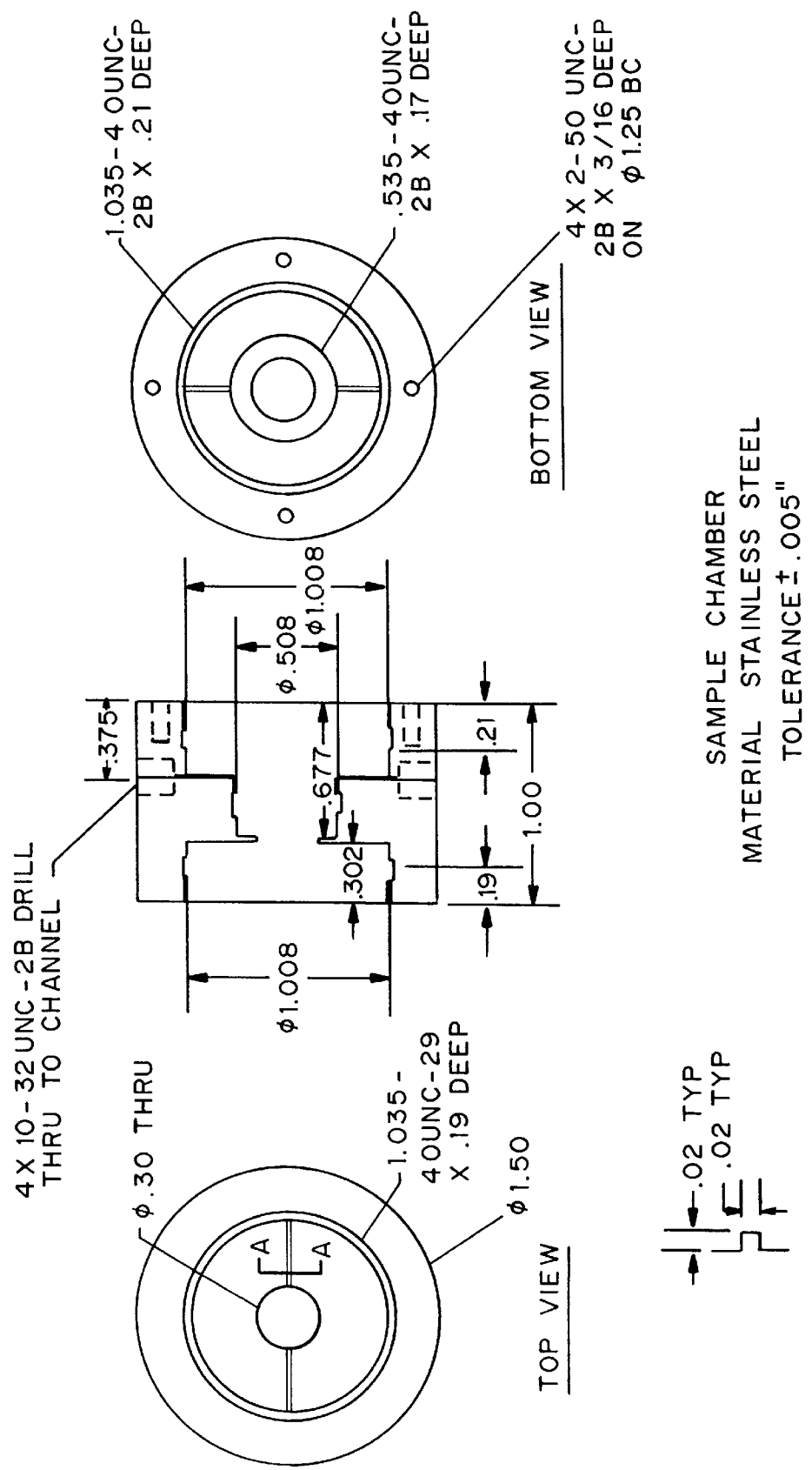

VASCULARIZED PERFUSED MICROTISSUE/MICRO-ORGAN ARRAYS

CROSS-REFERENCE TO RELATED APPLICATIONS

Priority is claimed to U.S. provisional application Ser. No. 60/078,452, filed Mar. 18, 1998.

BACKGROUND OF THE INVENTION

The present invention relates to microscale tissue arrays and their construction, where the microscale tissue array is constructed from a micromatrix seeded with cells which forms a microtissue and/or a micro-organ, and to methods for using the microscale tissue arrays in a variety of systems and assays, for example, for determining the effect of biological and/or chemical agents on the microscale tissue arrays, or for detecting the presence of biological and/or chemical agents using microscale tissue arrays.

Tissue engineering has emerged as a scientific field which has the potential to aid in human therapy by producing anatomic tissues and organs for the purpose of reconstructive surgery and transplantation. It combines the scientific fields of materials science, cell and molecular biology, and medicine to yield new devices for replacement, repair, and reconstruction of tissues and structures within the body. Many approaches have been advocated over the last decade. One approach is to combine tissue specific cells with open porous polymer scaffolds which can then be implanted. Large numbers of cells can be added to the polymer device in cell culture and maintained by diffusion. After implantation, vascular ingrowth occurs, the cells remodel, and a new stable tissue is formed as the polymer degrades by hydrolysis.

A number of approaches have been described for fabricating tissue regeneration devices for either in vitro or in vivo growth of cells. Polymeric devices have been described for replacing organ function or providing structural support. Such methods have been reported by Vacanti, et al., *Arch. Surg.* 123:545–49 (1988); U.S. Pat. No. 4,060,081 to Yannas, et al.; U.S. Pat. No. 4,485,097 to Bell; and U.S. Pat. No. 4,520,821 to Schmidt, et al. In general, the methods used by Vacanti, et al., and Schmidt, et al., can be practiced by selecting and adapting existing polymer fiber compositions for implantation and seeding with cells, while the methods of Yannas and Bell produce very specific modified collagen sponge-like structures.

Tissue regeneration devices must be porous with interconnected pores to allow cell and tissue penetration, if the device is of any significant thickness. Factors such as pore size, shape, and tortuosity can all affect tissue ingrowth but are difficult to control using standard processing techniques. U.S. Pat. No. 5,518,680 to Cima & Cima describes the use of solid free form fabrication techniques, especially three dimensional printing of polymer powders, to form matrices which can be seeded with dissociated cells and implanted to form new structures. The advantages of the solid free form methods to construct specific structures from biocompatible synthetic or natural polymers, inorganic materials, or composites of inorganic materials with polymers, where the resulting structure has defined pore sizes, shapes and orientations, particularly different pore sizes and orientations within the same device, with more than one surface chemistry or texture at different specified sites within the device, is readily apparent. However, the devices still have a major limitation: ingrowth of new tissue to form blood vessels which sustain the implanted cells must occur at the right time relative to the increasing cell density within the matrix to sustain the implanted cells, and other tissues must not encapsulate or infiltrate the matrix to choke out or otherwise destroy the implanted cells.

PCT/US96/09344 to Massachusetts Institute of Technology and Childrens' Medical Center Corporation describes the use of solid free-form fabrication (SFF) methods to manufacture devices for allowing tissue regeneration and for seeding and implanting cells to form organ and structural components, which can additionally provide controlled release of bioactive agents, wherein the matrix is characterized by a network of lumens functionally equivalent to the naturally occurring vasculature of the tissue formed by the implanted cells, and which can be lined with endothelial cells and coupled to blood vessels or other ducts at the time of implantation to form a vascular or ductile network throughout the matrix.

None of this technology, however, provides a means to maintain the tissue in vitro, nor to use the tissue as a diagnostic or screening tool.

Cells placed in typical in vitro culture generally lose at least some key differentiated physiological functions that they normally exhibit as part of organized tissues in the body. Thus, while cultured cells may be adequate for certain applications, for example, in detection of toxins and pathogens, they are certain to fail in other applications, for example, screening of drug which are metabolized by the tissues, or drugs which are cleared through interaction with a complex organ, not just a single isolated cell type. For example, no in vitro model of infection exists for hepatitis B virus (HBV) and hepatitis C virus (HCV), presumably because primary hepatocytes in typical culture situations rapidly stop expressing the cell surface receptors the viruses use to enter the cell. One can infer from this example of a known pathogen, which cannot currently be screened using cultured cells, that unknown pathogens (or toxins), which often utilize receptor-mediated uptake, could similarly elude detection in cultured cells. Similarly, drugs that must be bound by cell specific receptors to be taken up by the cells to be active, also cannot be tested in such systems. Xenobiotic metabolism, which is primarily carried out by a set of enzymes in the liver, is another function rapidly lost by cultured hepatocytes. Although the hepatic enzymes render most exogenous compounds less toxic, other molecules (as a common example, the pain-relieving drug acetaminophen) can actually become more toxic when metabolized by the liver. It is therefore critical to have a system for screening of drugs which can mimic in vivo conditions.

It is therefore an object of the present invention to provide an apparatus for in vitro analyses that effectively model tissue and/or organ physiological responses such as viral infection, and metabolism of xenobiotic agents.

SUMMARY OF THE INVENTION

Systems including (1) a micromatrix and perfusion assembly suitable for seeding and attachment of cells on and throughout the matrix and for morphogenesis of seeded cells into complex, hierarchical tissue or organ structures, wherein the matrix includes channels or vessels through which culture medium, blood, gases, or other nutrient or body fluids can be perfused while controlling gradients of nutrients and exogenous metabolites throughout the perfusion path independently of perfusion rate, and (2) sensor means for detecting changes in either cells attached on and to the matrix or to materials which are exposed to the cells on and within the matrix, have been developed. The micromatrices are made using conventional silicon processing technology, such as photolithography, wet etching, or deep reactive ion etching; micromachining; electro-discharge machining; reaction injection molding; thermoplastic injection molding; micromolding; punching; any of the solid free form technologies, such as three dimensional printing; or other types of manufacturing which can create micro through-holes in sheets of material, especially manufacturing technologies for plastics, such as micromolding, embossing, laser drilling, or electron deposition machining. Cells can be of one or more types, either differentiated cells, such as endothelial cells or parenchymal cells, including nerve cells, or undifferentiated cells, such as stem cells or embryonic cells. In a preferred embodiment, the matrix is seeded with a mixture of cells including endothelial cells, or with totipotent/pluripotent stem cells which can differentiate into cells including endothelial cells, which will line the channels to form "blood vessels", and at least one type of parenchymal cells, such as hepatocytes, pancreatic cells, or other organ cells.

The functional unit in these micromatrices is the channel containing cells and their exudates (such as extracellular matrix molecules) in the desired morphological structure. The term "channel" refers to a hole of constant or systematically varied cross-sectional area through a sheet of material approximately 50–500 $\mu$m thick; with a defined cross-sectional geometry, which may be rectangular, ovoid, circular, or one of these geometries with an imposed finer feature, such as scallops of cell dimension or smaller; defined surface chemistry; and defined dimensions, typically in the range of 75–1000 $\mu$m across, with dimensions optimized for each individual tissue or organ type (e.g., preferred channel dimensions for liver in rectangular or ovoid channels is 100–200 $\mu$m across one axis with at least 100 $\mu$m across on the other axis; embryonic stem cells prefer channels with dimensions between 200 and 1200 $\mu$m). Features of the channels are designed to achieve an effect on cell behavior, such as cell organization. The cell behavior does not occur simply because there is an arbitrary hole; the channel is designed to induce cells to organize in the channel to form tissue, either in solid form with blood vessels integrated therein, or in aggregate or spheroidal form. Induction of structure may occur under static conditions (no perfusion) or fluid may be perfused through the channels during morphogenesis to aid formation of histotypical structure, depending on the tissue. One can independently control both the perfusion rate through the array and the nutrient/metabolite/test compound concentrations on each side of the channels by any means.

A microscale tissue refers to a synthetically formed mass of cells forming a tissue structure or a structure that carries out tissue functions. As used herein, tissue refers to an aggregation of cells more or less similar morphologically and functionally; while a micro-organ includes cells of different morphology and/or function, such as hepatocytes and endothelial cells. The microscale tissue or organ unit contained in a single channel preferably is formed of less than about 10,000 cells, more preferably less than about 5,000 cells, and most preferably less than about 2,000 cells. The microscale tissue or organ unit contained in a single channel preferably is formed of at least about 150 cells. Microscale tissues (or micro-organs if formed of mixed cell types) may be combined to form multiunit tissue arrays. The density of channels in the array depends on the detection limits of the assay being performed, the size of the channels, and the materials of construction; preferable densities are at least 10–100 tissues/cm$^2$, with the total number of channels determined by the mass or number of cells required for a particular assay. A microscale tissue array refers to an array of synthetically fabricated microscale tissues. The array preferably contains at least about 4 microscale tissues, more preferably at least about 50 microscale tissues, but may contain only one channel if the readout is sensitive to the number of cells contained in a single channel.

The system can be used to screen materials for an effect on the cells, for an effect of the cells on the materials (for example, in a manner equivalent to tissue metabolism of a drug), to test a material on a biological that must first infect cells or tissues, such as viruses, to expand a biologic or unique cell population, such as stem cells, or to provide an environment for gene therapy. The microscale tissue arrays are particularly useful for the study of many phenomena, including clearance, metabolism, activation, transport, and bioavailability of xenobiotics, including drug candidates. The microscale tissue arrays can also be used to study toxicity, teratogenicity, genotoxicity, carcinogenicity, and mutagenicity, in terms of basal, local, and/or organ-specific impact, under conditions of acute or chronic exposure. The microscale tissue arrays can be used to construct disease models, for use in studies on the impact of chemical and/or biological agents on the course of the disease. The microscale tissue arrays can be used to detect the presence of infectious agents, as well as chemical and biological weapons. The microscale tissue arrays can also be used for dose ranging studies for drug candidates.

The results from these studies can be entered into mathematical models to predict the response of organs in vivo. The results can also be entered into mathematical models to predict pharmacokinetics and/or pharmacodynamics of chemical and biological agents. The systems employing the microscale tissue arrays can be integrated with other test systems, such as those which concern genomics, gene transcription, protein expression, and other biological phenomena of interest. In comparison to test systems using whole organs, test systems using microscale tissue arrays provide results at far less expense per test. In comparison to test systems using tissue slices and cells, test systems using microscale tissue arrays provide results at comparable expense per test; however, the results are more relevant to human health, as the cells in the microscale tissue array maintain high viability, phenotype, and differentiated function.

BRIEF DESCRIPTION OF THE FIGURES

FIG. 3A, mask pattern to produce channels with cylindrical grooves in the walls; channels will have the cross section shown. The diameter of the grooves can be tailored to match the diameter of the parenchymal cells (e.g., 25 $\mu$m for ES cells). FIG. 3B, illustration of proposed selective modification of channel surface chemistry. The interior of the grooves remains unmodified silicon or silicon coated with a fluoropolymer, while the exposed surfaces are coated with a PEG-based silane layer to inhibit initial cell adhesion. The interior of the grooves are coated with ECM proteins or other adhesion promoters to engender cell adhesion: the exposed silanized portions resist protein adhesion.

FIGS. 4A and 4B are schematics of the reorganization of cell mixtures in channels with surface texture and selectively modified surface chemistry, at an initial time (FIG. 4A) and after reorganization (FIG. 4B).

FIGS. 5A and 5B are schematics of an apparatus for using microscale tissue arrays as part of a high-throughput batch system for chemical and biological testing, wherein a microscale tissue array is placed in each well of a multi-well plate (FIG. 5A), and wherein the multi-well plate is placed on top of a vacuum box (FIG. 5B).

FIGS. 14A–14C are illustrations showing construction of a tissue matrix by mixing 100,000 hepatocytes and endothelial cells/ml (FIG. 14A); injecting the hepatocytes and endothelial cells (approximately 0.5 to 1 ml) into the matrix (FIG. 14B); and incubation of the matrix seeded with cells in 5% $CO_2$ at 37° C. (FIG. 14C).

FIG. 15A shows albumin secretion (pg/cell/hr) from perfused cell-scaffold constructs (circles) after 24 or 48 hrs. static culture. Scaffolds were perfused with culture medium for 90 min. and the effluent assayed for rat albumin. Squares show secretion data from 3 µg/ml collagen coated dishes. FIG. 15b shows albumin secretion (ng/min) over time of perfusion (hours) from three separate perfused cell-scaffold constructs (200 µm×400 µm channels) after 48 hrs. static culture. Scaffolds were perfused with culture medium and the effluent collected every hour beginning at 30 min. after the onset of perfusion.

FIG. 16 is a plan view of a sample chamber.

DETAILED DESCRIPTION OF THE INVENTION

I. Micromatrix Systems

Matrices

Figure 1:
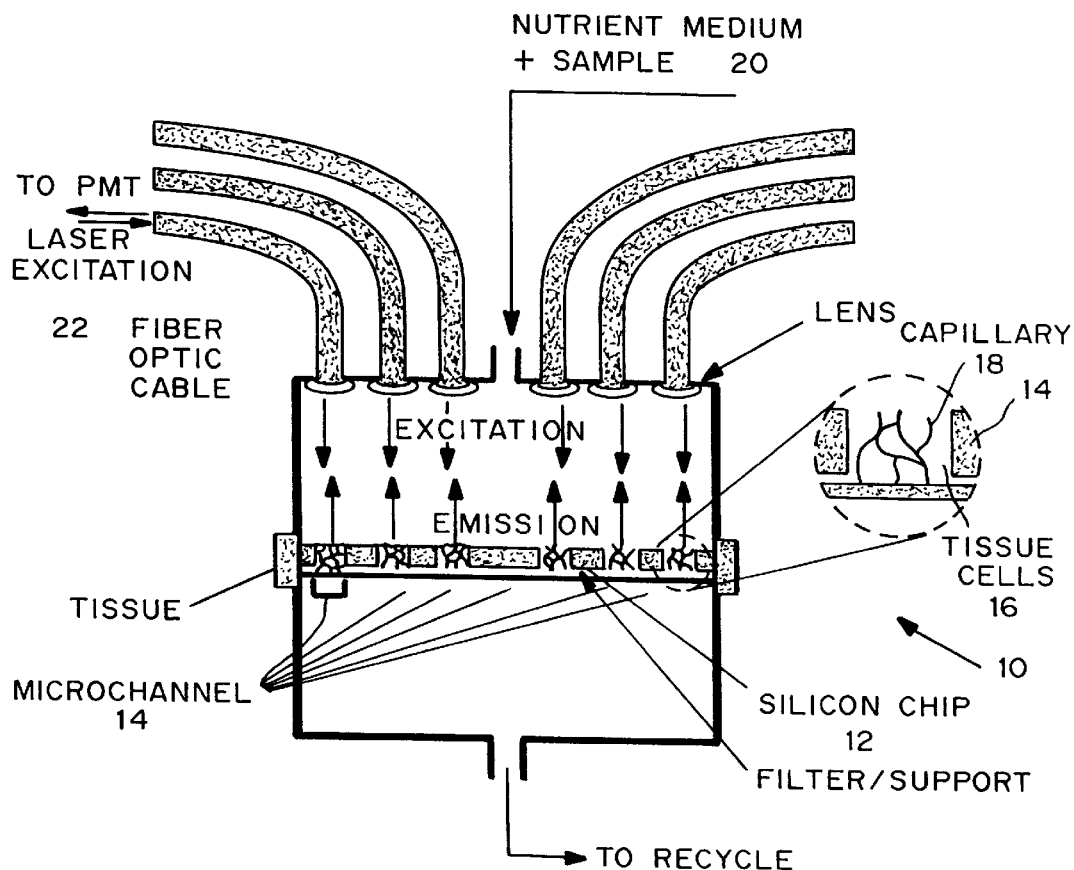
FIG. 1 is a schematic of a microarray of capillary bed-sized tissue units with an optical spectroscopy sensing system to detect changes in fluorescence intensity/spectrum of endogenous or exogenous fluorophores in the tissue upon injury.

A system is described which includes a matrix, cells attached to the matrix and forming organized tissue or organ structures within the matrix, a source of nutrients and oxygen for maintaining cell viability, a means for controlling gradients of nutrients and other molecules across the perfusion path in the matrix independently of fluid flow rate, and sensor means for detecting changes in the cells or agents administered to the cells.

The functional unit of the matrix are channels. These are typically between 75 and 400 µm in diameter. In the preferred embodiments, the matrix is a micromatrix, although the dimensions can range from nanometers to millimeters. The array will typically have a cross-sectional area of a few square centimeters or less, preferably 1 square centimeter or less. The depth of the array will typically be less than 1 centimeter, preferably 1 mm or less. These same size considerations apply to arrays of microscale tissues for test purposes.

The channels are seeded with cells which form tissue within the channel, or which form aggregates or spheroids suspended or maintained within the channels. Each layer of matrix containing channels within a single plane is referred to as a microtissue. These "microtissues" can be either tissues, i.e. formed of functionally similar cells, or organs, i.e. formed of a mixture of cells having different functions and/or phenotypes. For convenience, both terms are referred to as "microtissue" unless otherwise noted. Microtissues are layered together to form microscale tissue or micro-organ arrays. The arrays can consist of tissues stacked on top of each other, side by side each other, or both. They may be interconnected or isolated. In the preferred embodiment, an organ is formed in each channel, wherein each channel contains several cell types with different functions. The primary reason they are in individual channels is that they will not form appropriate tissue structures over large length scales. The number of cells which will form a tissue/organ structure is fixed and thus the mass of cells needed for a particular assay is obtained by scaling the number of each micro-organ in the total array. The microscale tissue preferably is formed of less than about 10,000 cells, more preferably less than about 5,000 cells, and most preferably less than about 2,000 cells. The microscale tissue preferably is formed of at least about 150 cells, although the micromatrix may be seeded with as few as 25 to 50 cells. A microscale tissue array refers to an array of synthetically fabricated microscale tissues, preferably at least about 4 microscale tissues, more preferably at least about 50 microscale tissues.

The type(s) of cells determine the function of the tissue. As used herein, tissue refers to an aggregation of cells more or less similar morphologically and functionally. In one embodiment, the matrix is seeded with a mixture of cells including endothelial cells and at least one type of parenchymal cells, such as hepatocytes, pancreatic cells, or other organ cells, or the matrix is seeded with totipotent/pluripotent stems cells which can differentiate into cells, including endothelial cells to form a micro-organ. Mixtures of cells of diverse function are referred to as micro-organs. With either approach, the endothelial cells (and in some cases other cells such as pericytes or stellate cells) will form "blood vessels" throughout the tissue. An organ refers to a differentiated structure of an organism composed of various cells or tissues and adapted for a specific function (*McGraw-Hill Dictionary of Bioscience*). As used herein, a microscale organ refers to a microscale tissue, or combination of microscale tissues, which exhibits at least one function or characteristic of a particular organ, at an representative, specific level. Specific level refers to absolute level per unit of scale, such as level per cell number, volume, mass, or surface area, considering only the cellular compartments, not the substrate. The cross-sectional area is typically less than 1 $cm^2$, and the depth is typically less than 0.5 cm. For example, in terms of the function of xenobiotic biotransformation, a microscale liver would transform a xenobiotic at a specific rate representative of a whole liver, where the specific rate might be measured in moles per unit time and cell volume. In terms of the characteristic of susceptibility to viral hepatitis infection, a microscale liver would exhibit a time course of infection representative of a whole liver, when infected with the same number of viral particles per cell or per cell surface area. The required degree of cell representation will depend on the particular user requirements. In certain circumstances, specific levels which are representative of the actual organ within an order of magnitude may be sufficiently accurate. In other circumstances, the specific levels may need to be within 10% or less of the actual organ levels. Sufficient accuracy over extended duration of testing will be critical for certain tests. Qualification studies will generally be performed with arrays of microscale tissue. If the compounds yield the desired results with the arrays, they are then screened using arrays of microscale organs.

A microscale organ mimicking liver function or characteristics is useful for monitoring drug clearance, production of metabolites, activation of prodrugs, capture of asiolo proteins, and susceptibility to toxins or acute or chronic infection.

High throughput screening can be carried out by preparing multiwell plates, and inserting microscale organs in each well. Different drugs can be evaluated simultaneously by adding different drugs to each well. The microscale organs can also be used in a differential bioreactor system. The reactor includes one or more microscale organs and means for maintaining the viability of the organs, for example, a supply of oxygen and nutrients. Sensors for following the metabolism of the agents can be present. Preferably, the reactor can be equipped with a computer to control, for example, the supply of oxygen and nutrients and the collection, analysis and purification of samples. Metabolites of the agents can be prepared and isolated by administering various agents to the bioreactor. In one embodiment, the microscale organ is sandwiched between filters which prevent passage of the organ but which allow passage of the metabolites. A steady stream of fluids, for example, blood, through the organ can remove the metabolites in a continuous manner. The metabolite can be extracted from the fluid and the fluid recycled through the organ. This represents a continuous process for preparing metabolites using the microscale organs. The reactor can be operated in a one-pass mode, a recirculating mode, or combination thereof.

Microscale organs can be used to monitor the effect of exposure of the organs to various therapeutic agents. If the organ is challenged in such a way that it can react to an effective dose of the therapeutic agent, the minimum effective dose can be calculated. Further, as the dose is increased, one can determine the maximum tolerated level. Accordingly, both dosage and efficacy can be measured using the microscale organs described herein.

The potential benefits of monitoring the exposure of the microscale organs to various therapeutic agents is that faster, cheaper secondary screens can be developed, which represent actual human organs, and which may be used in new disease models. This offers a potential reduction in animal testing and also offers testing on actual human tissue without subjecting human test patients to untested drugs. The microscale organs also offer an opportunity to test drugs in which no animal model is adequate.

The results from tests with microscale organs can be entered into appropriate scale-up models to predict the response of whole organs in vivo. Tests can furthermore be performed using a series of microscale organ arrays, arranged so as to provide a scale down model of an organ system. The results can be scaled-up to predict the response of the organ system in vivo or an entire organism, such as a human.

In some embodiments, the apparatus is used for in vitro analyses, for example, high throughput screenings of chemical and biological agents. In other embodiments, the apparatus is used as a bioreactor to produce chemical or biological agents. In other embodiments, the apparatus is used to generate hard-to-produce cells and tissue, such as stem cells. In still further embodiments, the apparatus is used to generate cells for implantation, optionally after the cells have been transfected. Examples of the apparatuses include micro-tissue devices, micro-scale organs, bioreactors and high throughput screening systems.

The apparatuses effectively model tissue physiological responses such as viral infection and metabolism of xenobiotic agents.

Test systems using microscale tissue arrays have a broad range of uses, including, but not limited to, studies on biotransformation, clearance, metabolism, and activation of xenobiotics; studies on bioavailability and transport of chemical agents across epithelial layers; studies on bioavailability and transport of biological agents across epithelial layers; studies on transport of biological or chemical agents across the blood-brain barrier; studies on acute basal toxicity of chemical agents; studies on acute local or acute organ-specific toxicity of chemical agents; studies on chronic basal toxicity of chemical agents; studies on chronic local or chronic organ-specific toxicity of chemical agents; studies on teratinogenicity of chemical agents; studies on genotoxicity, carcinogenicity, and mutagenicity of chemical agents; detection of infectious biological agents and biological weapons; detection of harmful chemical agents and chemical weapons; studies on infectious diseases; studies on the efficacy of chemical agents to treat disease; studies on the efficacy of biological agents to treat disease; studies on the optimal dose range of agents to treat disease; prediction of the response of organs in vivo to biological agents; prediction of the pharmacokinetics of chemical or biological agents; prediction of the pharmacodynamics of chemical or biological agents; studies concerning the impact of genetic content on response to agents; filter or porous material below microscale tissue may be chosen or constructed so as bind denatured, single-stranded DNA; studies on gene transcription in response to chemical or biological agents; studies on protein expression in response to chemical or biological agents; studies on changes in metabolism in response to chemical or biological agents; prediction of agent impact through database systems and associated models; prediction of agent impact through expert systems; and prediction of agent impact through structure-based models.

The apparatus addresses applications which cannot currently be fulfilled by existing systems of cultured cells; i.e., applications where the crucial biological response requires the integrated physiological function of at least two cell types interacting within a normal tissue structure. The phrase "normal tissue structure" means collections of at least one epithelial or mesenchymal-type cell i.e., a "tissue cell" in a three dimensional structure permeated by capillary blood vessels, where the capillaries are continuously perfused with fluid, as they generally would be with blood in the body. This type of organization provides the most promising means of retaining differentiated physiological cell and tissue functions outside the body, and consequently the most promising means of retaining sensitivity to the broadest range of pathogens and toxic agents.

Whereas known pathogens, xenobiotic agents, drugs, and toxins can potentially be detected by molecular assays, unknown pathogens and toxins may enter cells via as-yet-unidentified receptors, and act through as-yet-unknown enzymatic pathways, precluding molecular assays or even cell-based assays when the cultured cells have lost the relevant receptor or enzyme function. Of particular interest in the development of pharmaceuticals is the specificity of many receptor and enzyme pathways to human tissues, precluding screening or analysis of functions in animals or animal tissue. A sensor in which the combination of cells that form the tissue retain their complete physiological ability to respond to pathogens and toxins, combined with a means to detect tissue injury or infection, thus offers the broadest possible scope of detecting new agents.

The examples use known viral and chemical toxins acting on two different tissues: liver and embryonic stem cells to illustrate the necessity of the organized tissue structure, rather than isolated cells, in detecting pathogens which may be unknown as well as known.

Systems

The approach is exemplified by the system shown schematically in FIG. 1, where a unique flow-through micro array of capillary bed-sized tissue units is combined with an optical spectroscopy sensing system to detect changes in fluorescence intensity/spectrum of endogenous or exogenous fluorophores in the tissue upon injury. The technology combines a chip-based micro tissue arrangement with sensors to detect the changes in tissue behavior resulting from infection or toxic insult. Each of the system components are discussed separately below.

Figure 2A:
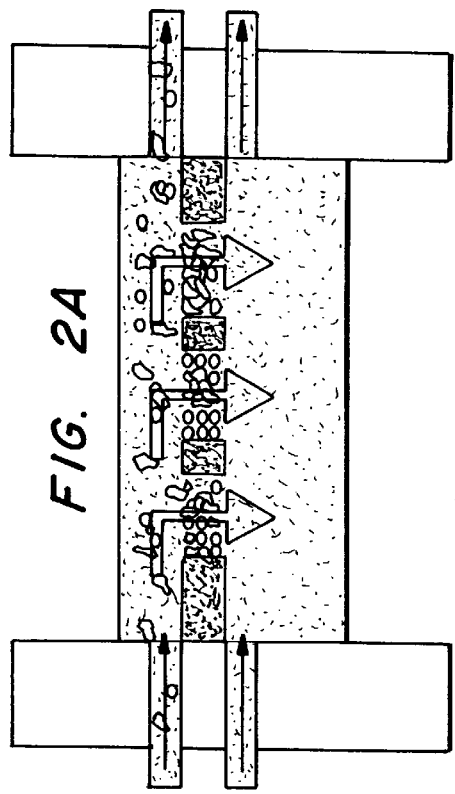
FIGS. 2A–2C are schematics of the reactor configuration for Prototype II, showing the reactor during cell seeding (FIG. 2A), the reactor operating in cross flow mode (FIG. 2B), and the reactor operating in forced flow mode (FIG. 2C).
Figure 2C:
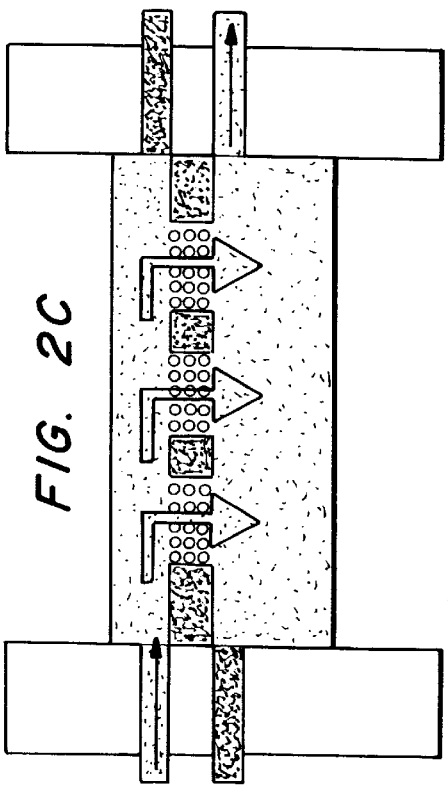
Figure 2B:
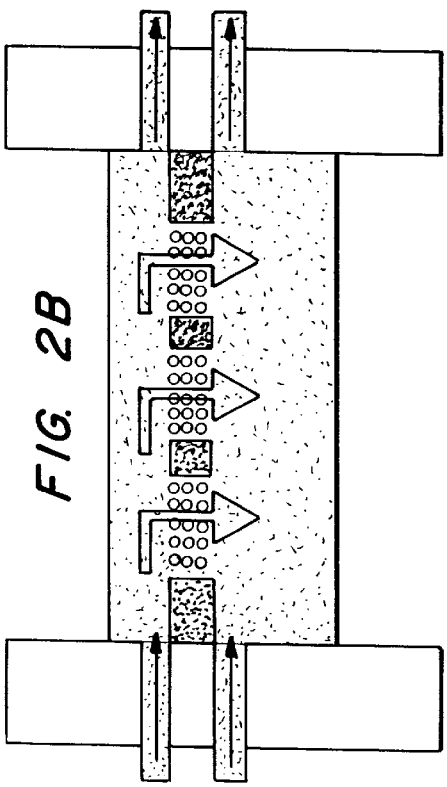

FIG. 1 is a cross-sectional view of a tissue-based biosensor system 10, with a view of the scaffold 12 (silicon chip with an array of open channels 14 through the thickness), which contains tissue-like structures 16 penetrated by perfused microvascular networks 18 through which culture medium 20 flows. The heart of the system is an array of tiny "tissue" units, for example, each about 300×300×300 $\mu$m, contained in an array of channels 14 etched through a silicon chip 12, as shown in FIG. 1. FIGS. 2A–2C illustrate a reactor system in which this array can be cultured. The reactor system can be operated in a cross-flow mode (FIG. 2B), in which medium perfusion through the arrays is driven by the pressure differential between two independent tangential perfusion circuits (one on either side of the scaffold). Other parameters of the perfusion circuits such as flowrate or nutrient concentration, may also be independently controlled, allowing for accurate control of gradients present in the system. The reactor system may also be operated in a forced flow mode (FIG. 2C), in which the entire flow from a single perfusion circuit is diverted through the array. In this configuration the flowrate dictates the pressure drop, gradients, etc. within the system. Culture medium containing the sample flows normal to the chip 12 and through the tissue units 16. When sample is applied, metabolic changes occur in the tissue which can be detected by a change in fluorescent intensity/spectrum of various endogenous or exogenous fluorescent markers. A miniaturized fiber optic system 22 is used to provide single or multi-photon excitation to individual channels, and to detect fluorescent intensity. Nutrient medium is circulated from a stirred reservoir in a recycle loop, with continuous medium replenishment in the reservoir.

Micromatrices Materials and Fabrication

The matrices can be formed of an inert material such as silicon, preferably coated with a material to enhance biocompatibility and cell adhesion, or a biocompatible polymer, preferably one which is not biodegradable.

Several levels of sophistication in scaffold surface chemistry are needed. At a simple level, one must control grossly where cells seeded on to the chip adhere and migrate. At a higher level of sophistication, one must pattern the surfaces of the channels to influence cell organization in three dimensions ("3D"). Finally, one can modify the surfaces of the channels to provide specific growth and differentiation signals to the cells. Methods of tethering growth factors to silicon substrates have been developed.

The initial design of the scaffold is constrained by two requirements: (1) Cell number—each scaffold must hold enough cells (approximately 150 to 500,000) to perform the sorts of chemical, biochemical and molecular biology assays needed to interpret the fluorescent readouts; and (2) Channel dimensions—the depth of the channel is constrained to approximately 300 $\mu$m by the need to prevent nutrient depletion (although this constraint may be relieved by using a perfusion medium which contains components of artificial blood; i.e., which transports more oxygen per unit volume than culture medium), while the cross sectional geometry and dimensions are determined by the need to optimize morphogenesis, for example, with dimensions (100–600) $\mu$m) of various geometries.

With representative channel dimensions of 300×300×300 $\mu$m and formation of tissue-like cell density ($2\times10^8$ cells/$cm^3$), approximately 100 channels (approximately 1 $cm^2$) will be required. A multichannel array is also desirable to determine the statistical variation in performance of tissue within each channel and to allow combinatorial approaches to optimizing channel dimensions and geometry.

Silicon Matrices

Choosing silicon wafers to form the sensor platform provides several advantages. The thickness of a wafer is the desired depth of the tissue and arrays of channels can easily be created within the wafer using deep-trench etching technology, for example, available in the Microsystems Technology Lab (MTL) at MIT. Silicon matrices can be also fabricated by electron-discharge machining (EDM) techniques such as die-sinking EDM and wire EDM. Silicon wafers combine ease of fabrication—both of many different channel geometries during optimization studies as well as large-scale production—with a platform for precise control of surface chemistry to achieve specific cell behaviors. Silicon also may offer advantages in terms of heat transfer properties needed for rapid cryopreservation of tissue structures.

Scaffolds can be produced by etching single-side polished silicon wafers of standard thicknesses followed by grinding and polishing to reduce the wafer thickness to 150 to 400 µm. Alternatively, etch through microchannels can be fabricated in thin, double-side polished wafers of desirable target thickness. In this case, no further grinding and polishing is necessary. During etching, the active thin wafers can be mounted with photoresist to quartz handle wafers, facilitating end etch point determination. The photoresist can be applied to the whole surface of the handle wafer or only to its perimeter. Discs of 1.5 to 2 cm diameter can be produced with the appropriate array of channels in each; with the current design, seven scaffolds can be produced from each wafer, with relatively large features compared to standard Si microfabrication. This allows one to make photolithography masks by printing designs on high resolution (3386 dpi) photographic film. This flexibility in mask production allows us to produce masks much more cheaply and quickly than the standard chrome-on-glass approach and thus to test many different channel geometries.

There are at least two feasible deep-etching approaches to achieve an array of channels etched through a silicon chip. The preferred approach is to use an inductively-coupled plasma (ICP) etcher. A machine for producing high-aspect ratio features in silicon, the Surface Technology Systems (STS) Si deep-trench etcher, can be used to etch through holes in Si using photoresist or Si dioxide as masks. The STS deep reactive ion etcher uses $SF_6$ for etching and $C_4F_8$ for passivation. Therefore, the polymer covering the surfaces will contain mainly carbon and fluorine, possibly with some traces of sulfur. The channels formed with the STS have vertical walls, with the cross sectional geometry determined by the mask. The channels may thus have features such as parallel grooves in the wall if such features are desired for inducing appropriate tissue morphogenesis. During etching, etch gases react on the exposed Si etchant surfaces to form fluorocarbon oligomeric/polymeric species, such as C(HF)$_x$C(F$_2$)$_y$C(H$_2$)$_z$, which are hydrophobic in character and which persist after removal of the photoresist. Although this "polymer" can be removed by a combination of $O_2$ plasma etch followed by washes in either HF or pirhana solution, its presence is advantageous for initial studies for two reasons: the hydrophobic character allows cell adhesion to the walls of the channels to be tailored by adsorption of extracellular matrix (ECM) proteins; and it provides a natural mask to allow selective modification of the top and bottom surfaces of the wafer, since the polymer is unreactive to many standard silane chemistries.

The second approach to channel formation is to use wet chemical etching with KOH. Prior to the availability of deep-trench plasma etchers, KOH etching was the dominant approach to deep Si etching. KOH etching is very anisotropic—certain crystal faces are preferentially etched to produce Si (111) surfaces—resulting in channels with sloped walls. Crystal orientation determines the slopes of the walls, and the cross-section geometry is also dictated by crystal structure. Negative and positive wall slopes can be achieved by careful selection of the pattern orientation relative to the crystal. Channels with diverging flow may offer some advantages in physiological function. Faceting is a more serious problem with KOH etching and may thus limit its use.

Following etching, cleaning, and polishing of the Si wafer, a macroporous filter, for example, a PDVF filter, is attached to the back of the scaffold. The filter surface is made hydrophilic by exposure to an oxygen plasma. By positioning the filter onto a clean oxide surface of the etched silicon wafer, the high energy surface on the filter forms chemical bonds to the silicon oxide surface resulting in a strongly adherent assemblage. The presence of a thin layer of water at the interface along with the application of heat have been used by us to produce this composite structure.

To ensure cell adhesion preferentially in the channels, the upper surface of the silicon substrate can be coated with an ethylene oxide-based film using silane chemistry to couple the organic material to the oxide surface. Other treatments can also be used to enable bonding of a second wafer to the first water. This derivatization can be performed selectively on the outer surface of the wafer as the presence of the fluoropolymer materials on the walls of the channels will prevent attachment to this location. Reacting between chemically synthesized $CH_3(OCH_2CH_2)_3O(CH_2)_{11}SiCl_3$ and the oxide surface can be used to produce self-assembled monolayer films that are known to passivate silicon substrates against the adsorption of many types of adventitious species. With this silane, the reaction proceeds to anchor an oriented molecular film on the oxide surface and expose ethylene oxide groups to the surrounding environment. For channels produced using KOH as the etchant, the channels and top surface can be first treated with $CH_3(CH_2)_{17}SiCl_3$ to coat the channels and outer surface with alkyl chains to make the surface hydrophobic. The outer surface can be selectively cleaned using applied $UV/O_2$ treatments at a grazing angle to minimize decomposition of coated regions within the channel or the use of aqueous cleaning solutions that will be prevented from entering the channels due to capillary forces that restrict penetration of the aqueous solution into the hydrophobic channels. For these cases, the exposed cleaned surface can be made non-adsorbing by reaction with $CH_3(OCH_2CH_2)_3O(CH_2)_{11}SiCl_3$ that will again form a layer selectively on the outer surface due to the presence of the hydrophobic film within the channel areas.

Following silanization, materials which promote adhesion, such as extacellular matrix materials ("ECM"), RGD peptides, or tethered growth factors, can be adsorbed from aqueous buffer onto the discs to ensure cell adhesion preferentially to the channels. Because of the different surface chemistries present within the channels and at the outer surfaces, the proteins will adsorb preferentially on the channel walls, as neither $CH_3(OCH_2CH_2)_3O(CH_2)_{11}SiCl_3$-derived upper surface nor the filer are protein adhesive. Verification of the surface chemistries and their ability to direct protein and cell adsorption can be confirmed using optical and fluorescent microscopies and various surface spectroscopies on both whole and cleaved samples.

Patterning of the channel walls may improve tissue morphogenesis and function. Examples of the types of geometric features to be imposed are depicted in the channel cross-section shown in FIGS. 3A and 3b. The surface chemistry of the recessed and exposed portions of the features can be selectively modified to induce cell patterning along the specific regions of the channel walls. Adsorptive regions will be patterned with a hydrophobic alkyltrichlorosilane, $CH_3(CH_2)_{17}SiCl_3$, to direct placement of the proteins and cells while non-adsorptive regions within the channel and covering the upper surface will use an ethylene oxide-terminated trichlorosilane, $CH_3(OCH_2CH_2)_{2,3}O(CH_2)_{11}SiCl_3$, to prevent protein and cell attachment to these areas. This patterning of adsorbates and their resulting regions of specific surface chemistries can be directed to allow specified inner areas of the channel walls to be made adsorptive while producing spacer areas that are non-adsorptive between them. The approach will use a modification of microcontact printing to localize the desired reagents into the corners of the channels. In brief, a polydimethylsiloxane (PDMS) stamp prepared using a master pattern etched into silicon by the above methods will be constructed to dictate the locations of applied reagents (and thus surface chemistries) within the channel. The master will produce a patterned stamp of PDMS that copies the periodic spacing of the channels; however, its size will be smaller in dimension than the channel. A likely geometry is a spoke design so that the PDMS stamp will contact a limited subset of available area within the channel walls and deposit silane only in these regions. After stamping this pattern of silane within the channel, exposure of the sample to a solution of silane can be used to fill in the open regions of the channel not derivatized by the stamp with a silane to yield a different surface chemistry and adsorption characteristic in these regions. This latter silane can be $CH_3(OCH_2CH_2)_3O(CH_2)_{11}SiCl_3$ to produce non-adsorptive surfaces in specific regions of the channel (those not derivatized by stamping with the first silane) and on the upper surface.

The channel can be tailored to present specific ligands, such as tethered epidermal growth factor ("EGF"). The procedure used previously to attach EGF to surface uses silane reagents to prime the surface and subsequent reaction chemistry using tresyl chloride chemistry to attach the EGF material to the surface. As the methoxy-terminated ethylene glycol surface and filter are inert to the tresyl chloride chemistry used for attaching EGF to tethering sites on the surface, patterned regions of EGF within the channels can be constructed by exposing a patterned channel system and exposing its subsequent reaction solutions to construct EGF domains within the channels.

Polymeric Matrices

In addition to silicon, the matrices can be formed from polymers, such as polycarbonate, polystyrene, polyurethane, polypropylene, polyethylene, polymethyl methacrylate, polyester, and polytetrafluoroethylene (TEFLON™), using methods such as solid free-form methods or standard polymer processing methods such as micromolding. Depending on the processing method, the material forming the matrix may be in solution, as in the case of SLA, or in particle form, as in the case of SLS, BPM, FDM, and 3DP. In a preferred embodiment using SSF, the material is a polymer. In the first method, the polymer must be photopolymerizable. In the latter methods, the material is preferably in particulate form and is solidified by application of heat, solvent, or binder (adhesive). In the case of SLS and FDM, it is preferable to select polymers having relatively low melting points, to avoid exposing incorporated bioactive agent to elevated temperatures.

In the case of 3DP, a biocompatible material, preferably in particulate form, or as a porous sheet, is applied to a solid platform on a movable piston for solidification and/or incorporation of bioactive agent. A roller evenly spreads the particles over the platform bed. Solvent and/or binder is then selectively printed onto the polymer particles. After each layer is "printed", the piston lowers the polymeric material so that the process can be repeated to form the next layer. The particles can be of any shape, including fibrous or rod shaped, although a more spherical particle will typically flow more smoothly. The particles are preferably in the range of ten micrometers or greater in diameter, although smaller particles can be used if spread in a liquid medium and allowed to dry in between printings.

In addition, polymeric micromatrices can be formed by reaction injection molding, thermoplastic injection molding, micro-molding, and punching. Molds for some of these processes can be made using e.g. lithography and micromachining, electro-discharge machining, and electroplating.

A number of materials are commonly used to form a matrix. Unless otherwise specified, the term "polymer" will be used to include any of the materials used to form the matrix, including polymers and monomers which can be polymerized or adhered to form an integral unit, as well as inorganic and organic materials, as discussed below. In one embodiment the particles are formed of a polymer which can be dissolved in an organic solvent and solidified by removal of the solvent, such as a synthetic thermoplastic polymer, preferably non-biodegradable, such as polyesters, polyurethanes, polystyrene, and polycarbonates, although biodegradable polymers may be useful for some applications. Examples include ethylene vinyl acetate, poly (anhydrides), polyorthoesters, polymers of lactic acid and glycolic acid and other $\alpha$ hydroxy acids, and polyphosphazenes, protein polymers, for example, albumin or collagen, or polysaccharides. The polymer can be non-biodegradable or biodegradable, typically via hydrolysis or enzymatic cleavage. Examples of non-polymeric materials which can be used to form the matrix include organic and inorganic materials such as hydoxyapatite, calcium carbonate, buffering agents, and lactose, as well as other common excipients used in drugs, which are solidified by application of adhesive or binder rather than solvent. In the case of polymers for use in making devices for cell attachment and growth, polymers are selected based on the ability of the polymer to elicit the appropriate biological response from cells, for example, attachment, migration, proliferation and gene expression.

Photopolymerizable, biocompatible water-soluble polymers include polyethylene glycol tetraacrylate (Mw 18,500) which can be photopolymerized with an argon laser under biologically compatible conditions using an initiator such as triethanolamine, N-vinylpyrrolidone, and eosin Y. Similar photopolymerizable macromers having a poly(ethylene glycol) central block, extended with hydrolyzable oligomers such as oligo(d,l-lactic acid) or oligo(glycolic acid) and terminated with acrylate groups, may be used.

Examples of biocompatible polymers with low melting temperatures include polyethyleneglycol (PEG) 400 which melts at 4–8° C., PEG 600 which melts at 20–25° C., and PEG 1500 which melts at 44–48° C. Another low melting material is stearic acid, which melts at 70° C.

Other suitable polymers can be obtained by reference to The Polymer Handbook, 3rd edition (Wiley, N.Y., 1989), the teachings of which are incorporated herein.

For microstructures tailored to bone, inorganic powders in the final device increase the strength of the device and provide a source of minerals for the regenerating tissue. The strength requirements of soft tissues such as liver are substantially less than for bone, so greater void fractions in the final devices can be tolerated.

The polymeric matrices can be formed using solid free-form processes, reaction injection molding, thermoplastic injection molding, micromolding, and punching.

b. Solid Free Form Manufacturing Processes

Three Dimensional Printing (3DP)

3DP is described by Sachs, et al., "CAD-Casting: Direct Fabrication of Ceramic Shells and Cores by Three Dimensional Printing" *Manufacturing Review* 5(2); 117–26 (1992) and U.S. Pat. No. 5,204,055 to Sachs et al., the teachings of which are incorporated herein. Suitable devices include both those with a continuous jet stream print head and a drop-on-demand stream print head.

3DP is used to create a solid object by ink-jet printing a binder into selected areas of sequentially deposited layers of powder. Each layer is created by spreading a thin layer of powder over the surface of a powder bed. The powder bed is supported by a piston which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three dimensional structure. The unbound powder supports temporarily unconnected portions of the component as the structure is built but is removed after completion of printing. The powder/binder layer forming process is repeated so as to build up the device layer by layer. While the layers become hardened or at least partially hardened as each of the layers is laid down, once the desired final part configuration is achieved and the layering process is complete, in some applications it may be desirable that the form and its contents be heated or cured at a suitably selected temperature to further promote binding of the powder particles. In either case, whether further curing is required, the loose, unbonded powder particles are removed using a suitable technique, such as ultrasonic cleaning, to leave a finished device. Finer feature size is also achieved by printing polymer solutions rather than pure solvents. For example, a 10 wt % PLC solution in chloroform produces 200 $\mu$m lines under the same conditions as above. The higher solution viscosity prevents slows the migration of solvent away from the center of the primitive, i.e. the structural elements that result from printing individual binder droplets.

Stereo-Lithography (SLA) and Selective Laser Sintering (SLS)

SFF methods are particularly useful for their ability to control composition and microstructure on a small scale for the construction of these medical devices. The SFF methods, in addition to 3DP, that can be utilized to some degree as described herein are stereo-lithography (SLA), selective laser sintering (SLS), ballistic particle manufacturing (BPM), and fusion deposition modeling (FDM).

Stereolithography is based on the use of a focused ultraviolet (UV) laser which is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired device is obtained. The most recently created layer in each case is always lowered to a position for the creation of the next layer slightly below the surface of the liquid bath. A system for stereolithography is made and sold by 3D Systems, Inc. (Valencia, Calif., USA), which is readily adaptable for use with biocompatible polymeric materials.

SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation (Austin, Tex., USA).

Ballistic Particle Manufacturing (BPM) and Fusion Deposition Modeling (FDM)

BPM uses an ink-jet printing apparatus wherein an ink-jet stream of liquid polymer or polymer composite material is used to create three-dimensional objects under computer control, similar to the way an ink-jet printer produces two-dimensional graphic printing. The device is formed by printing successive cross-sections, one layer after another, to a target using a cold welding or rapid solidification technique, which causes bonding between the particles and the successive layers. This approach as applied to metal or metal composites has been proposed by Automated Dynamic Corporation (Troy, N.Y., USA).

FDM employs an x-y plotter with a z motion to position an extrudable filament formed of a polymeric material, rendered fluid by heat or the presence of a solvent. A suitable system is available from Stratasys, Incorporated (Minneapolis, Minn., USA).

Other Device Variables

The effects of texture can be beneficial in designing devices to get optimal tissue growth rates. A single channel of square cross-section can have smooth surfaces on one or two sides and textured surfaces on the other. Smooth surfaces can allow rapid cell migration, while textured surfaces can provide a site for cells to differentiate.

Composite devices can be made by combining inorganic and organic components. In particular, it may be desired to increase the amount of matrix material in the device above that which can be obtained by one-pass printing of a solution of a matrix material into an inorganic powder bed, for example, by adding a polymer latex to the printing solution. Another method is to mix a polymer powder with an inorganic powder. Still another method is to spread only polymer powder in the bed, and print a dispersion of inorganic particles (up to 30 vol %) in a solvent which will bind the polymer powder together.

Controlling Porosity in Devices

Porosity can be created either at the level of the feature size (between 10 and 20 $\mu$m and greater) or at a sub-feature size level. At the level of the feature size, porosity is controlled by where the features are placed, and thus pore size and shape can vary in three dimensions.

Porosity at a subfeature size level can be created in a variety of ways.

(1) Printing a polymer solution onto a bed of particles which are not soluble in the polymer and which can be subsequently leached with a non-solvent for the polymer. In this case, the polymer which forms the device is printed onto a bed of particles such as salt, sugar, or polyethylene oxide. After the printing process is complete, the device is removed from the powder bed and placed in a nonsolvent for the polymer which will dissolve the particles. For example, polymer in chloroform can be printed onto a bed of sugar particles, and the sugar subsequently can be leached with water.

(2) Printing a polymer solution onto a bed of particles which are partially soluble in the printed solvent. An example is printing a polyester (PE) solution onto a bed of polyethylene oxide particles (PEO). This procedure may allow interpenetration of PEO into the surface of the PE and improve surface properties of the final device. Following printing, the PEO can be leached with water.

(3) Printing a polymer solution onto a heated bed of polymer. An example is printing PE in chloroform onto a bed of PE particles heated to 100° C. The boiling point of chloroform is 60° C., and it will thus boil on hitting the particle bed, causing a foam to form.

(4) Printing a polymer solution onto a bed containing a foaming agent.

(5) Printing with solvents which have only a small solubility for the powder. In this manner, only a small amount of polymer is deposited at the necks between the particles leaving much of the original porosity in the powder bed.

Modifying surface properties in select regions of the device is also important and can be accomplished by printing a solution containing surface-active agents into the regions or lines in between where the binder is printed. As used herein, a "surface-active agent" may be an agent which promotes cell adhesion, such as an RGD peptide, or a material which inhibits cell adhesion, such as a surfactant, for example, polyethylene glycol or a PLURONIC™ (polypropylene oxide-polyethylene oxide block copolymers). The surface-active agent should in general be contained in a solvent immiscible with the solvent used to print the binder.

For example, it may be desirable to incorporate adhesion peptides such as the RGD adhesion peptide into certain channels (e.g., those for blood vessel ingrowth). An adhesion peptide, such as the peptide having a hydrophobic tail marketed as PEPTITE™ by Telios (La Jolla, Calif.), can be dissolved in water and printed into the "voids" using a second set of printing nozzles. Adding water, a relatively non-volatile solvent, can alter the kinetics of solvent removal from regions printed with binder. For example, adding water can slow solvent removal by occluding the surface area for evaporation, and can help decrease warpage. On contact with the polymer surface, the peptide will adsorb out of solution onto the polymer surface.

The surface can also be modified to prevent cellular adhesion. This may be desirable to prevent excessive soft connective tissue ingrowth into the device from the surrounding tissue, and can be accomplished, for example, by printing an aqueous solution of a PLURONIC™ (BASF) or POLOXAMER™ in the voids. The hydrophobic block of such copolymers will adsorb to the surface of the channels, with the hydrophilic block extending into the aqueous phase. Surfaces with adsorbed PLURONICS™ resist adsorption of proteins and other biological macromolecules. Other adhesion-preventing materials are described in Lee, et al., *J. Biomed. Mat. Res.*, 23:351–68 (1989), the teachings of which hereby are incorporated by reference.

Printing the device with surface active agents while the "walls" of the device are still "wet" with organic solvent (such as chloroform) can enhance the adsorption of the adhesion-preventing material to the walls and can even allow the hydrophobic block to become blended into the surface, enhancing the stability of the resulting surface modification.

Figure 3A:
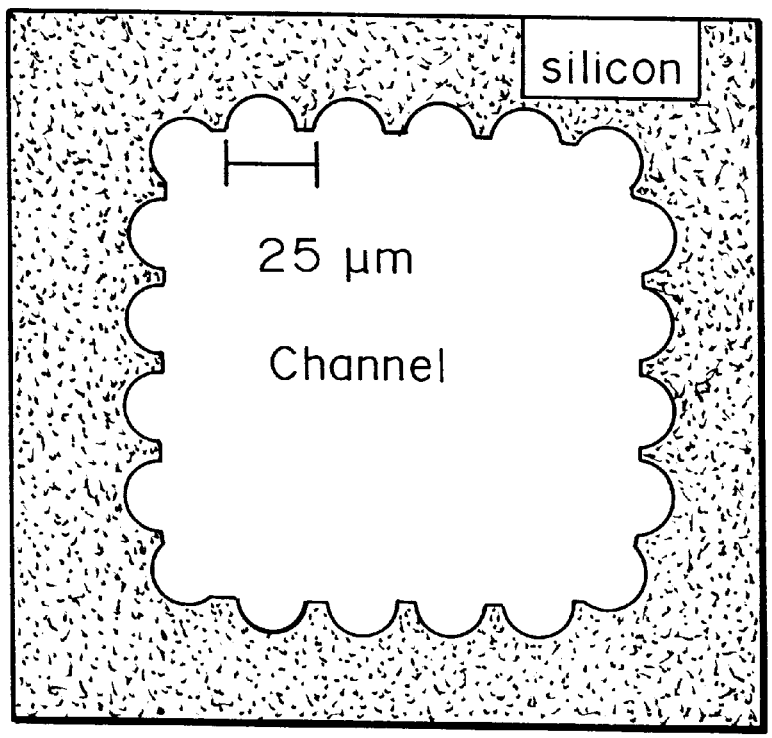
FIGS. 3A and 3B are schematics of making a silicon based device.
Figure 3B:
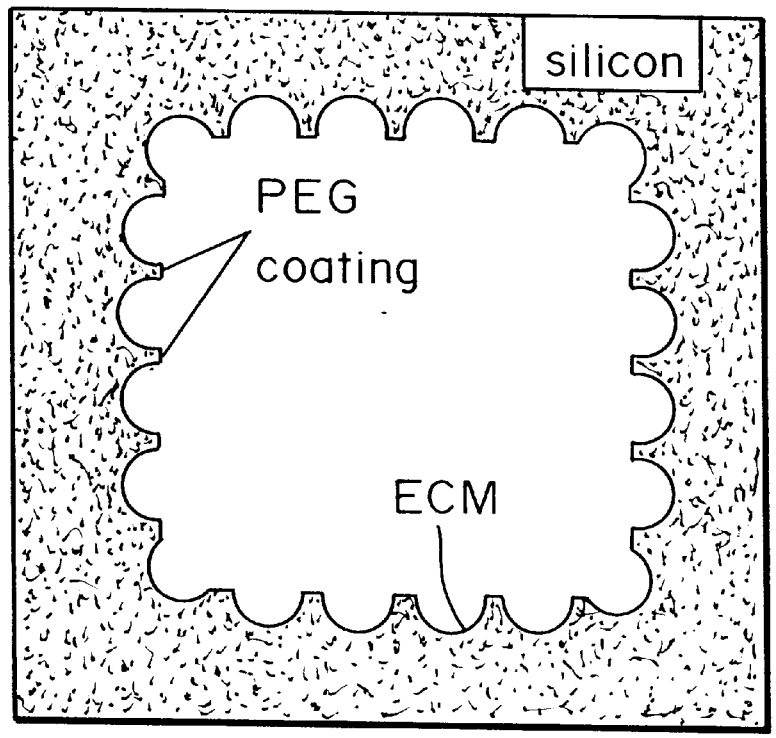

Cells can be positioned at specific sites in the matrix by using selective surface chemistries locally. Referring to FIGS. 3A and 3B, cells can be targeted to specific sites within the matrix in any of several ways:

(1) Region A of a polymer channel is printed with a general cell adhesion molecules such as fibronectin, collagen, or laminin, to enhance cell adhesion, while region B is printed with a surfactant such as PLURONIC™ 68 (polyethylene oxide-polypropylene oxide block copolymers) to inhibit cell adhesion. Printing the surface modifiers can be accomplished by printing an aqueous solution of the desired surface modifier in a line next to the binder line printed to form the channel; the protein or surfactant will adsorb from the aqueous solution to the surface of the polymer. Alternatively, the surface modifier can be included with the binder itself. Surfactants, including proteins, can modify surface properties when included at very low concentrations in the binder, 0.1 to 1% by weight. At these concentrations, changes in the bulk properties are small. At an initial time, parenchymal cells are seeded and adhere in region A while no cells adhere in Region B. After approximately one to two weeks of culture, endothelial cells or another cell type can be seeded on top of the parenchymal cells. Region B can be modified prior to seeding the second cell type by treating with an aqueous solution of an adhesion protein such as fibronectin, which can displace the surfactant and thus enable cell adhesion in regions where it was previously inhibited to allow a complete coating by endothelial cells on all interior surfaces of the matrix.

(2) Region A can be printed with a molecule which is selective for one cell type and Region B with a molecule selective for another cell type. Such molecules will generally include a highly specific small ligand, such as REDV for endothelial cells or galactose for hepatocytes, linked to a strong hydrophobic moiety (such as than in Cell-Tak, a commercially available reagent) which will adsorb strongly to the surface of PLLA and poly(lactic acid-glycolic acid) (PLGA). This allows spatial segregation when seeding more than one cell type at the initial time.

Bioactive Agents Which Can Be Incorporated

There are essentially no limitations on the bioactive agents that can be incorporated into the devices, although preferred materials are those which can be processed into particles using spray drying, atomization, grinding, or other standard methodology, or those materials which can be formed into emulsifications, microparticles, liposomes, or other small particles, or applied as a coating, and which remain stable chemically and retain biological activity in a polymeric matrix.

Bioactive agents include compounds having principally a structural role, for example, hydroxyapatite crystals in a matrix for bone regeneration. The particles may have a size of greater than or less than the particle size of the polymer particles used to make the matrix. Examples generally include proteins and peptides, nucleic acids, polysaccharides, nucleic acids, lipids, and non-protein organic and inorganic compounds, referred to herein as "bioactive agents" unless specifically stated otherwise. These materials have biological effects including, but not limited to, anti-inflammatories, antimicrobials, anti-cancer, antivirals, hormones, antioxidants, channel blockers, and vaccines. It is also possible to incorporate materials not exerting a biological effect such as air, radiopaque materials such as barium, or other imaging agents.

In one embodiment, cell growth, differentiation, and/or migration modulators are incorporated into specific regions of the device at the same level of resolution as the pores and channels. These materials are commercially available from suppliers such as Sigma Chemical Company, and have been extensively described in the literature.

There are two principle methods for incorporation of bioactive agents: as a dispersion within a polymeric matrix and as discrete units within a discrete polymeric matrix. In the first case, the bioactive agent is preferably applied in the polymer particle binder; in the second, the bioactive agent is applied in a non-solvent for the polymer particles.

The devices can include particles of bioactive agent dispersed or embedded in a matrix of degradable polymer, such as PLA, PGA, and their copolymers (PLGAs). The release rate of bioactive agent is determined by the erosion rate of the polymer rather than just diffusion. Thus, the drug release rate can be controlled by the distribution of the drug throughout the matrix or by variation of the polymer microstructure so that the erosion rate varies with the position in the device. A drug concentration profile that is periodic with position away from the device surface will, for example, yield a drug release rate that is periodic in time as the polymer is eroded. The same effect can be achieved by periodic variation in polymer composition or porosity.

In another embodiment, a bioactive agent can be incorporated by adsorption onto the surface of the structural polymer during fabrication in the following way: print a line of binder (for example, chloroform for poly(L-lactic acid) (PLLA)), then adjacent to the line print a line of aqueous solution with a fibroblast growth factor (FGF)-heparin angiogenic factor mixture in it. The FGF-heparin will adsorb out of the solution onto the polymer surface to locally provide the angiogenic factors.

Cells

Slicing up pieces of donor organs to obtain tissue is impractical: The pieces of tissue obtained by slicing have a layer of dead cells at the surface, and the vascular architecture of tissue is such that a small slice cannot readily be perfused with a test fluid. In the preferred embodiment, donor tissue is dissociated into individual cells, the cell types separated and purified, and recombined within the channels in a way which allows the histotypic architecture of the tissues to reform. Standard procedures are used to obtain and dissociate cells. For example, primary rat hepatocytes and non-parenchymal cells can be isolated using standard collagenase perfusion (Griffith, et al., *Ann. N.Y. Acad. Sci.* 831 (1997); Cima, et al., *Biotech. Bioeng.* 38:145–58 (1991)). Human hepatocytes can be obtained from collagenase perfusion of tissue obtained from liver resections or from liver biopsies through the New England Organ Bank (Fontaine, et al., *J. Ped. Surg.* 30:56–60 (1995)). Rat microvascular endothelial cells can be obtained from collagenase perfusion of fat. Human microvascular endothelial cells can be obtained from Clonetics. It is unlikely that matching of tissue types for microvascular endothelium is required, as endothelium exhibits great plasticity to adapt to new environments. Embryonic stem cells (ES cells) can be cultured in the totipotent state using standard techniques with differentiation induction, for example, by replacing LIF with various cytokines.

Cells then are seeded on and within the matrix to form tissue or organs. The cells can be administered into the matrix as a mixture, since they will segregate and attach to surfaces according to their natural function. Cells which can be used include parenchymal cells which provide metabolic or organ function, endothelial cells which form linings in vessels or channels equivalent to blood vessels, nerve or nervous tissue, connective tissue (including bone, cartilage and cells differentiating into bone forming cells and chondrocytes), and undifferentiated cells, such as embryonic cells, stem cells, and other precursor cells. Cells can also be transgenic for one or more genes. For example, cells can be engineered to express CD4, so that the cells can be examined for infection with a virus that binds to the CD4 molecule.

In one embodiment, the matrix is seeded with a mixture of cells including endothelial cells, which will form "blood vessels", and at least one type of parenchymal cells, such as hepatocytes, pancreatic cells, or other organ cells. In another embodiment, the matrix is seeded with stem cells, which are then propagated. Liver is useful as a prototype tissue because it offers two highly relevant examples of the need for the unique attributes of tissue-based systems.

ES cells, derived from cells at the very early stage of the embryo, retain the potential to differentiate into almost any type of tissue in vitro and are widely used in vivo as the basis of creating transgenic mice. They can be propagated in a highly undifferentiated state in the presence of proteins which inhibit differentiation and then induced to differentiate into tissue structures in the presence of differentiation factors, although great control over the differentiation process currently does not exist. Because ES cells are obtained from the very early embryo, they may offer significantly greater longevity in vitro than other cell types and be more robust in terms of preservation and transport. They also offer the potential for creating multiple tissue types from a single source within a single scaffold.

Culture or Perfusion Media

Culture medium composition must be considered from two perspectives: basic nutrients (sugars, amino acids) and growth factors/cytokines. Co-culture of cells often allows reduction or elimination of serum from the medium due to production of regulatory macromolecules by the cells themselves. The ability to supply such macromolecular regulatory factors in a physiological way is a primary reason 3D perfused co-cultures are used. A serum-free medium supplemented with several growth factors suitable for long-term culture of primary differentiated hepatocytes (Block, et al., *J. Cell Biol.* 132:1133–49 (1996)) has been tested and found to support co-culture of hepatocytes with endothelial cells. ES cells are routinely maintained in a totipotent state in the presence of leukemia inhibitory factor (LIF) (Williams, et al., *Nature* 336:684–87 (1988)), which activates gp130 signaling pathways (Saito, et al., *J. Immunol.* 148:4066–71 (1992)). Several medium formulations can support differentiation of ES cells, with different cytokine mixes producing distinct patterns of differentiation (Millauer, et al., *Cell* 72:835–46 (1993); Gendron, et al., *Dev. Biol.* 177:332–46 (1996); Bain, et al., *Dev. Biol.* 168:342–57 (1995)). Medium replacement rates will be determined by measuring rates of depletion of key sugars and amino acids as well as key growth factors/cytokines. Growth factor depletion is a seldom-recognized limiting factor determining medium replacement rates (Reddy, et al., *Biotechnol. Prog.* 10:377–84 (1994)).

Sensors

Sensors can be used to detect changes in pH, oxygen levels, specific metabolites such as glucose, presence or absence of an indicator molecule such as a viral protein, or any other indicia of an effect on the tissues or a material exposed to the tissues within the apparatus.

In one embodiment, readouts of injury or infection are based on changes in fluorescence of the tissue as detected by a miniaturized fiber optic array which excites fluorescence via either single or multiphoton means. The nature of the excitation is a critical parameter addressed in the technology development. Multiphoton excitation offers several advantages over single photon, in terms of resolution and prevention of tissue damage.

Many types of fluorescent readouts are possible. Changes in basic metabolic parameters of the tissue can be assessed by measuring the change in NAD(P)H levels via intrinsic fluorescence of these molecules. Cells can also be pre-loaded with a dye which leaks in the case of membrane damage, resulting in a decrease of fluorescent intensity. Alternatively or in addition, reporter genes can be transfected into the cells under the control of a stress-related promoter which is activated during tissue injury to produce a fluorescent product. This latter approach is of particular interest for detecting viral infection on a rapid time scale.

The objective in the detection scheme is to provide a fast, sensitive, field-adaptable, and minimally invasive fluorescence spectroscopic readout of tissue injury. A panel of potential indicators which will vary in either fluorescence intensity and/or spectrum have been identified. Since responses may require monitoring cellular biochemical state within normal tissue structure, it may not be sufficient to analyze only the surface layer of cells in the tissue, but to selectively monitor the cellular strata several cells deep into the channel interior. These requirements can be summarized into four design criteria for the optical detection system: (1) depth selection detection in thick (300 $\mu$m) tissue, (2) flexible excitation and detection scheme to image a variety of indicators, (3) minimally invasive to the living tissue culture in the device, (4) fast signal detection with high sensitivity, (5) rugged and field adaptable.

Using single photon excitation, confocal detection is needed to separate fluorescence which originates from the channel interior from its surface. A confocal microscope is a well-developed instrument designed to optically section thick specimens. Two apertures or pinholes are arranged in conjugate planes; one in front of the light source and one in front of the detector. This design can be simplified and made more robust for on-line detection by the use of single mode fiber optics. Through a dichroic beam splitter, excitation light is introduced into a single mode fiber (FIG. 1; beam splitter is not depicted). The light emitted from the fiber can be collimated by a lens. A second lens can focus the collimated light into the channel of the tissue chip. High resolution is not critical in this application—no imaging is required—and thus low optics and the chip to provide spaces for the hydraulic design in the flow chamber. The fluorescence from the sample is collected by two relay lenses and reflected back into the single mode fiber. The small diameter fiber functions simultaneously as the excitation and emission pinhole aperture in this system. Fluorescence originated outside the focal region can not be refocused by the relay lenses on to the fiber optics and is rejected. This process provides us depth discrimination. A number of chromophores with excitation wavelengths spanning near-UV to the blue-green region of the spectra can be considered during this project. Fluorescence indicators of particular interest are the endogenous chromophores, pyridine nucleotides. The pyridine nucleotides, NAD(P)H are excited in the region 365 nm and fluoresce in the region 400–500 nm. Another indicator of interest is green fluorescence protein (GFP) which can be excited in either near UV or the blue region of the spectrum and typically emits at about 510 nm. In order to excite this wide range of chromophores, a tunable UV argon-ion laser can be acquired for this study. Although this laser is not sufficiently robust for field application, it provides the flexibility to test a large set of fluorophores. After the proper set of chromophores is identified, less flexible but more robust and compact laser system can be easily incorporated. This fiber optic confocal design is a mature technology and can be rapidly incorporated into the tissue sensor to assess the changes in cellular biochemistry under toxin stress inside the tissue chip.

Although a toxin sensitive tissue chip may be built based on one-photon confocal approach, the use of two-photon approach can improve the system by increasing fluorescence signal to noise ratio and decreasing tissue damage. This new approach to study is based on two-photon microscopy developed by Denk et al. (Denk, et al., *Science* 248:73–77 (1990)). Chromophores can be excited by the simultaneous absorption of two photons each having half the energy needed for the excitation transition. Since the two-photon excitation occurs only at the focal point of a high numerical aperture objective, a region of high temporal and spatial concentration of photons. Using two-photon excitation, over 80% of the total fluorescence intensity comes from a 1 $\mu$m thick region about the focal point for a 1.25 numerical aperture objective. This depth discrimination effect of two-photon excitation arises from the quadratic dependence of two-photon fluorescence intensity upon the excitation photon flax which decreases rapidly away from the focal plane. The depth discrimination is a result of the physics of the excitation method and no confocal detection pinhole aperture is needed. This localization of two-photon excitation can be best visualized in a simple bleaching experiment.

To demonstrate the effect of two photon excitation, a two photon excitation volume was focused in the center of a 15 $\mu$m fluorescent latex sphere. The excitation volume was scanned repeatedly along the x axis until photobleaching occurred. A 3-D image stack of the latex sphere was acquired, in which a series of images are x-y planes of the sphere at increasing distance from the center. No photobleaching was observed beyond 1 $\mu$m.

Two-photon excitation allows selective assessment of the tissue physiological state at any point in the interior of the tissue chip channel. There are a number of advantages to the multi-photon approach as compared with confocal approach where the sample's absorption and scattering coefficients are high, such as those in tissues: (1) The typical scattering and absorption in the infrared spectral range is over an order of magnitude less than the near UV or the blue-green region. Using infrared excitation in the two-photon microscope minimizes the attenuation of the excitation signal. (2) Confocal microscopy uses the emission pinhole aperture to reject out of focus light. Inside deep tissue, scattering of the signal photons is inevitable. The consequent path deviation results in a significant loss of these photons at the confocal pinhole. The collection geometry for the fluorescence photons is less critical in the two-photon case where a large area detector can be used without a pinhole aperture. Most of the forward-scattered photons can be retained. (3) Two-photon excitation minimizes tissue photo-damage. Conventional confocal techniques obtain 3-D resolution by limiting the observation volume, but fluorescence excitation occurs throughout the hourglass-shaped light path. In contrast, two-photon excitation limits the region of photo-interaction to a sub-femtoliter volume at the focal point. (4) Two-photon excitation wavelengths are typically red-shifted to about twice the one-photon excitation wavelengths. This wide separation between excitation and emission spectrum ensures that the excitation light and the Raman scattering can be rejected while filtering out a minimum of fluorescence photons. (5) Many fluorophores have found to have very broad two-photon absorption spectra. A single properly-chosen excitation wavelength can excite a wide range of fluorophores with emission bands ranging from near-UV to near-infrared.

These advantages of the two-photon approach makes it an attractive alternative to single photon approach. However, the miniaturization of a two-photon system still requires extensive research. Problems such as pulse dispersion in fiber system still have to be resolved. Therefore, a second focus of developing optical system for the tissue chip is the development of miniaturization technology for two-photon excitation spectroscopy. Two-photon microscopes can be constructed to assess tissue toxin response as a function of tissue depth in the chip channel and to optimize the optics configuration to maximize detection efficiency in the unique geometry of the tissue chip. If the two-photon approach can be shown to be advantageous as compared with that of the one-photon confocal method, a final miniaturized fluorescence detection system based on two-photon excitation can be constructed.

Miniaturized fiber optic fluorescence spectrometers are available which can be used. One system is based on an one-photon excitation and confocal detection scheme. A second system involves the use of two-photon excitation. The advantage of this system includes lower tissue damage, higher throughput and higher versatility in terms simultaneous monitoring of multiple indicators.

Sensors other than fluorescent sensors can also be used. For example, samples can be analyzed by using infrared spectrophotometers, ultraviolet spectrophotometers, gas chromatograms, high performance liquid chromotograms, and other detection means known to those of skill in the art. These can be used to measure nutrients, gases, metabolites, pH, and other indicators of cell activity, infection, and metabolism.

II. Formation and Propagation of Tissues in the Micromatrices

The overall objectives are to obtain stable tissue structures within a scaffold configuration amenable to detection of events indicating cell injury by toxins or pathogens. The approach is based on the observation that mixtures of the various cell types from a mature tissue will spontaneously reform tissue-like structures under appropriate conditions and that cultures of embryonic stem cells (ES cells) will spontaneously form transient microcapillary structures when induced to aggregate. The unique aspect of the approach described herein is the focus on formation of perfused capillary structures within the tissue of interest, to induce stable differentiation of the cells and enable long-term culture.

The size of the tissue units is geared toward that comparable to a normal capillary bed, the smallest unit of functional tissue. This size ensures that enough cells are present to establish the correct tissue micro environment yet small enough that the fluid flowing through is not depleted of nutrients. A goal is to obtain reproducible structures firmly adherent to the walls of the channel to provide uniform passage of test fluid through the tissue.

The approach is based on rational manipulation of the intrinsic ability of dissociated cells to re-form native tissue structures. Histotypic cell reaggregation has been observed in several simple systems in vitro; e.g., formation of (unperfused) 3D capillary networks in protein gels and formation of epithelial layers from dispersed keratinocytes. Biophysical analyses of the observed phenomena are yielding insights into how morphogenesis can be controlled by manipulating measurable factors such as cell—cell and cell-substrate adhesion strengths, and some level of predictive capability is now possible, although not the level of a priori design of a perfused capillary network within a tissue. Based on biophysical principles, then, and keeping in mind that the biophysics are determined in part by the underlying chemistry (i.e., the ability of cells to form bonds with each other and the substrate), one can identify a set of parameters which can be systematically varied to influence tissue morphogenesis and function in the channels, regardless of tissue type. These parameters include scaffold surface chemistry; channel microgeometry (channel dimensions and configuration in the direction normal to fluid flow); degree of cell aggregation during seeding/seeding protocol; scaffold thickness; perfusion rates; and culture medium composition (sugars, amino acids, growth factors and cytokines) and replacement schedule.

Scaffold surface chemistry exerts effects primarily through setting the balance of cell-substrate versus cell—cell adhesion forces, affecting both morphogenesis and tissue function via multiple outcomes. At least some degree of adhesion of cells to the surface is desired to provide support for the tissue under flow conditions. However, if the surface is highly adhesive, cells adjacent to the surface will tend to spread and flatten out along the surface. A high degree of cell spreading is associated with loss of function in many cell types (Mooney, et al., *J. Cell. Phys.* 151:497–505 (1992)) and may impair function of the tissue. Preferential adhesion of endothelial cells to the channel walls might lead to overgrowth of endothelial cells, as they exhibit higher proliferative potential than hepatocytes and show maximal rates of growth at high degrees of spreading (Ingber, et al., *J. Cell. Biol.* 109:317–30 (1989)). Cell adhesion and spreading can be controlled by the amount of extracellular matrix adsorbed to an otherwise poorly-adhesive surface. Both silicon and the polymer deposited on the channels during the ICP etching are relatively non-adhesive to cells in the absence of serum or other proteins. Thus, adsorption of ECM proteins such as collagen or fibronectin at relatively low, intermediate, or high coating densities will engender relatively low, medium, or high cell adhesions strengths and concomitant degrees of cell spreading relative concentration of the protein (DiMilla, et al., *J. Cell Biol.* 122:729–37 (1993); Mooney, et al., *J. Cell. Phys.* 151:497–505 (1992)), and thus one can use an extracellular matrix protein such as Type I collagen for systematically modulating cell adhesion in most studies.

Channel microgeometry also can be manipulated to affect both morphogenesis and function. The ability to manipulate the geometry of the channel walls is one of the most powerful motivations for using silicon microfabrication technology. Grooves or scallops within the walls (FIGS. 3A and 3B) with feature sizes comparable to cell diameters (10 to 20 $\mu$m) can be used to provide a template for cell organization in the direction of flow during the static seeding process. Such features may also provide a means to allow a relatively high degree of cell adhesion to the surface without concomitant cell spreading; the features force the cell into a rounded shape while providing sufficient surface area for strong cell attachment. It may also be desirable to selectively control the surface chemistry of exposed and recessed features to assist with morphogenesis and differentiation. For example, making the exposed surfaces of the channel between the grooves resistant to initial cell adhesion (FIGS. 3A and 3B) allows fluid flow at that interface immediately following seeding, but is expected to induce capillary formation over the course of several days due to the natural migration/sorting of endothelial cells to fluid/tissue interfaces (FIGS. 4A and 4B). Channels will need to have cross sectional dimensions at least 5 cell diameters (approximately 80–100 $\mu$m depending on cell type) to provide sufficient cell mass free of wall effects.

The degree of cell aggregation during seeding and seeding protocol can influence morphogenesis and protocols may be tissue-specific. Aggregates of hepatocytes and endothelial cells in free solution form spheres, with the endothelial cells lining the outer surface (fluid tissue interface) (Ammann, et al., *Toxicol. in Vitro* 11:43–56 (1997)) while spherical aggregates of ES cells in free solution form spontaneous, but transient, microcapillary networks throughout the network 4–6 days after aggregation (Doetschman, et al., *J. Embryol. Exp. Morphol.* 87:27–45 (1985); Kennedy, et al., *Nature* 386:488–93 (1997)). It thus may be preferable to allow aggregation of hepatocytes/endothelial cells to proceed within the channels during a static period of a few hours after being seeded. It may be preferable, however, that ES cells and possibly hepatocytes be allowed to aggregate in free solution, then seeded into the scaffold. No detrimental effects on cells maintained at high density in the channels with no perfusion for several hours following seeding are anticipated, as the diffusion distance of oxygen in dense tissue from culture medium equilibrated with atmospheric oxygen is about 200 $\mu$m (Cima, et al., *Bioprocess Eng.* 5:19–30 (1990); Cima, et al., *J. Biomech. Eng.* 113:143–51 (1991)); diffusion from the two open ends of the channel will thus be sufficient to supply the 300 $\mu$m thick cell aggregate during static periods.

Another potentially preferable form of seeding involves staged delivery. For example, hepatocytes could be seeded into the channels initially; following a culture period of hours to days, and then endothelial cells could be introduced in one or several layers on top of the hepatocytes. Through operation of the bioreactor in cross-flow mode (FIG. 2B) one can induce oxygen gradients within channels by reducing the oxygen tension present in the lower perfusion circuit. The endothelial cells then would be expected to exhibit an angiogenic response to this chemotactic oxygen gradient, migrating towards the areas of low oxygen tension and forming capillaries which then permeate through the aggregated hepatocytes.

Scaffold thickness sets a lower limit on the necessary perfusion rates required to maintain nutrients at appropriate levels along the entire length of the channel. A rough estimate of the acceptable length for the depth of the channel can be obtained by considering the length of capillaries in tissue, which are typically between 400 and 1000 $\mu$m. The oxygen carrying-capacity of culture medium is less than that of blood, so shorter channels (250–350 $\mu$m) are required to prevent nutrient depletion while maintaining comparable flow rates through capillaries and the same capillary volume per unit volume of tissue; detailed calculations based on tissue nutrient consumption rates may be found in Griffith et al., "In vitro organogenesis of vascularized liver tissue," *Ann. N.Y. Acad. Sci.*, 831:382–97 (1997). Oxygen partial pressure at the inlet at outlet of the scaffold can be monitored with in-line oxygen microphobes. Readout of NAD(P)H fluorescent levels as a function of position in the channel can be used to infer metabolic viability.

Perfusion rates influence morphogenesis and function via both mechanical and chemical means. Perfusion-induced shear stresses on cells activate signaling pathways which may signal damage or homeostasis depending on the level of shear. Fluid shear can negatively influence the differentiated function of epithelial cells such as hepatocytes, but can be required for maintenance of normal phenotypic function of cells normally found in shear environments, such as endothelial cells, although excessive shear can cause abnormal function in even these cells. Tissue shear rates can be estimated by mathematical modeling using known average volumetric flow rates in each channel and information on the tissue structures (dimensions and numbers of capillaries) obtained from a combination of immunostaining/multiphoton spectroscopy and histology/immunostaining. The minimum perfusion rate is determined by the oxygen consumption rate of the tissue; in the preferred embodiment, the oxygen concentration is maintained at the tissue outlet at approximately venous levels.

Perfusion rates through the tissue arrays are controlled through the use of a cross-flow bioreactor system (FIGS. 2A–2C). FIG. 2A shows separate perfusion circuits provide tangential culture medium flow across the top and bottom of the chip. Cells can be seeded into the scaffold by perfusing a cell suspension through the upper circuit. The reactor can then be operated under cross-flow conditions, where the pressure difference drives flow from the upper circuit to the lower circuit through the channels (FIG. 2B). Alternatively, the reactor may be operated under forced flow mode, where the upper circuit flow is diverted through the channels and out the lower chamber outlet (FIG. 2C).

In the cross-flow arrangement (FIG. 2B), two separate perfusion circuits are maintained, one which flows across the top of the scaffold and one which flows across the bottom. The total hydrostatic pressure in each circuit can be maintained independently (e.g., through the use of pressure release valves or throttle valves) and perfusion flow through the cells in the channels is driven by the difference in this pressure. In this arrangement, a "static" period with no perfusion rate can be maintained following seeding while keeping the oxygen and other nutrient concentration at well-defined levels on the upper and lower sides of the chip. During the "static" period, the flowrates in the top and bottom circuits are preferably the same. The oxygen partial pressure in these circuits may or may not be the same, depending on the nature of each experiment. For example, it may be desirable to decrease the oxygen tension in the lower perfusion circuit to introduce an oxygen gradient within the channels. During routine operation, the total flow rate through the upper circuit (i.e., tangential to the chip surface) is maintained at least 10-fold greater than the perfusion flowrate through the chip, ensuring that significant oxygen gradients do not develop along the surface of the chip. During routine operation, the total flow rate through the bottom circuit (i.e., tangential to the chip surface) also is maintained at least 10-fold greater than the perfusion flowrate through the chip, but this is not a requirement, as the flowrate in the bottom circuit may be lower.

The reactor shown in FIG. 2 allows for the placement of a filter downstream of the scaffold. This allows for cells to be cultured in the local environment of the channels without being removed or washed away from the scaffold by medium perfusion. In this method, a single scaffold is covered on one side by a dry 5 $\mu$m pore size filter. The pore size of the filter must be less than 10 $\mu$m in order to prevent endothelial cells from passing through the pores. It is preferably between 1 and 5 $\mu$m. The pore size is preferably greater than 0.1 μm. The filter can be held in place by bonding it to the scaffold or by being "sandwiched" in place by another silicon scaffold identical to the first, taking care to align the channels of the two scaffolds. In the latter method, the second scaffold supports the filter and eliminates the need for direct bonding to the scaffold. The construct can then be placed and secured in the reactor.

FIGS. 4A and 4B are schematics of the reorganization of cell mixtures in channels with surface texture and selectively modified surface chemistry, at an initial time (FIG. 4A) and after reorganization FIG. 4B). Directed growth of capillaries in ES cultures, which form spontaneous microvascular networks, also may occur due to preferential cell adhesion to the grooves.

Modeling the distribution of flow is an important component of the scaffold design process, as it allows one to interpret the interplay between tissue mechanics and fluid stresses in the morphogenesis of structure and tells how to vary experimental parameters such as cell adhesion to the channel walls in order to achieve appropriate structures. Predictive simulations are complicated by network compliance and the tendency for biological remodeling that might occur as a result of stresses acting on the vascular endothelium. The model is based on one developed by Kamm et al. to describe the flow of blood through the pulmonary microvascular bed (Dhadwal, et al., *J. Appl. Physiol.* 83:1711–20 (1997)). That model is used to examine the effect of physiologically relevant variability in vascular dimensions and compliance on blood flow through segments and on perfusion patterns within the capillary bed as a whole. It should be modified to reflect the appropriate boundary conditions of the channel.

Tissue organization can be assessed by both light and electron microscopic histology. For liver tissue, endothelial cells and hepatocytes can be selectively labeled and examined also with confocal microscopy. Immunostaining for endothelial markers and parenchymal markers can be used to determine blood vessel organization in histological sections; ink infiltration also can be used. Image analysis can be used to determine the vessel dimensions and density as inputs for the mathematical modeling.

Hepatocyte differentiated state can be assessed by the secretion of serum albumin (Cima, et al., *Biotech. Bioeng.* 38:145–58 (1991)) and the maintenance of P450 enzymes as assessed by metabolite production from standard probe substrates. These assays can be carried out non-invasively on long-term perfusion cultures. Differentiation of ES cells can primarily be by invasive techniques; however, detection of hematopoetic function might be achievable if migration of cells produced in the tissue into the circulating medium occurs.

The technology described herein also can be used in a bioreactor designed to propagate hard to culture cells, such as stem cells, pancreatic islet cells and differentiated nerve cells. These cells can be used directly in therapeutic applications, for example, formation of an artificial pancreas for treating diabetes. Alternatively, the cells can be transfected with genetic material while in the bioreactor and then either used directly for therapy, or used to generate various proteins which are then administered.

A problem with prior art tissue engineering of hematopoetic stem cells is that stem cell expansion in vitro has proven to be problematic. Prior methods have provided early progenitor cells, but not stem cells. When gene transfer is attempted in vitro, the genes are introduced to the progenitor cells, but not stem cells. Accordingly, the gene transfer is transient rather than permanent.

By maintaining the normal tissue architecture, for example, the endothelial-lined vessels throughout the tissue, and by appropriate design of the channel architecture to drive certain cells into certain places, one can obtain a marrow-like environment which stimulates stem cell expansion in vivo. The cells can be harvested, for example, by adding a soluble compound to the medium (for example, a chemotherapeutic agent) which causes the stem cells to extravasate into the "vascular" space as they do in the body. The cells can be harvested by reversing the direction of the flow and switching the flow to a collection filter. This is analogous to how stem cells are collected from patients, wherein the cells are harvested from the peripheral blood by first stimulating the cells to move from the marrow into the blood by giving the patient a chemotherapeutic agent.

One means for expanding stem cells is to perfuse a micro organ version of a human liver with a protease, such as collagenase, which makes the liver tissue responsive to mitogens such as epidermal growth factor (EGF).

III. Assembly of Test Systems

FIG. 5A is a schematic illustration of an apparatus for using microscale tissue arrays as part of a high-throughput batch system for chemical and biological testing. A microscale tissue array 101 is placed in each well 102 of a multi-well plate 103. The microscale tissue arrays may be held above the bottom of the wells through ridges or slots in each well. The bottom 104 of each well may consist of solid material, such as glass or plastic, filter material, such as nylon, cellulose, nitrocellulose, or PVDF, or porous material, such as porous glass or porous silicon. Culture medium or test fluid is in direct contact with the top of the microscale tissue array and permeates the tissue array.

105 is in direct contact with the top of the microscale tissue array and permeates the tissue array. If the microscale tissue array is held off the bottom of the well, a certain volume of culture medium or test fluid 105a will occupy the space between the microscale tissue array and the bottom of the well. The gas phase compositions above the multi-well plate can be adjusted so as to provide the appropriate oxygen, pH, and carbon dioxide levels throughout the microscale tissue arrays.

FIG. 5B is a schematic illustration of an apparatus for using microscale tissue arrays as part of a high-throughput batch system for chemical and biological testing, wherein the multi-well plate 115 is placed on top off a vacuum box 114. A microscale tissue array 101 is placed in each well of the multi-well plate. The microscale tissue arrays may be held above the bottom of the wells through ridges or slots in each well. The bottom 117 of each well may consist of filter material, such as nylon, cellulose, nitrocellulose, or PVDF, or porous material, such as porous glass or porous silicon. As in FIG. 5A, culture medium or test fluid is in direct contact with the top of the microscale tissue array and permeates the tissue array. If the microscale tissue array is held off the bottom of the well, a certain volume of culture medium or test fluid will occupy the space between the microscale tissue array and the bottom of the well.

In FIG. 5B, the vacuum box is configured with a gas inlet 111 and a gas outlet 112. A vacuum may be applied to the gas outlet, such that the fluid surrounding each microscale tissue array is brought through each well bottom, down through a funnel 118, and into the corresponding well 119 of a multi-well collection plate 113. Gas may be subsequently added to the vacuum box through gas inlet 111, providing a target gas phase composition and pressure in the box. The gas phase composition and pressure may be different than that of gas phase above the multi-well plate with the microscale tissue arrays. The gas phase compositions can be adjusted so as to provide the appropriate oxygen, pH, and carbon dioxide levels throughout the microscale tissue arrays.

Figure 6B:
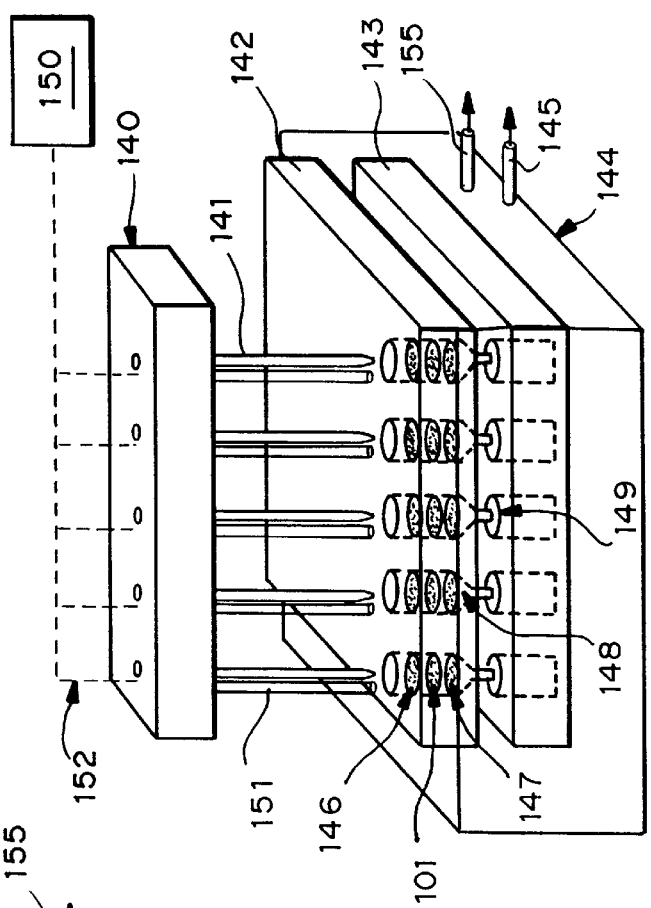
FIGS. 6A and 6B are schematics of an apparatus using microtissue arrays as part of a high-throughput batch system for chemical and biological testing, wherein the multi-well plate is placed on top of a vacuum box and a manifold system is used to deliver fluid to each well at frequent intervals (FIG. 6A), and wherein the multi-well plate is placed on top of a vacuum box, a manifold system is used to deliver fluid to each well at frequent intervals, and a sensor array is used to detect events in each well (FIG. 6B).
Figure 6A:
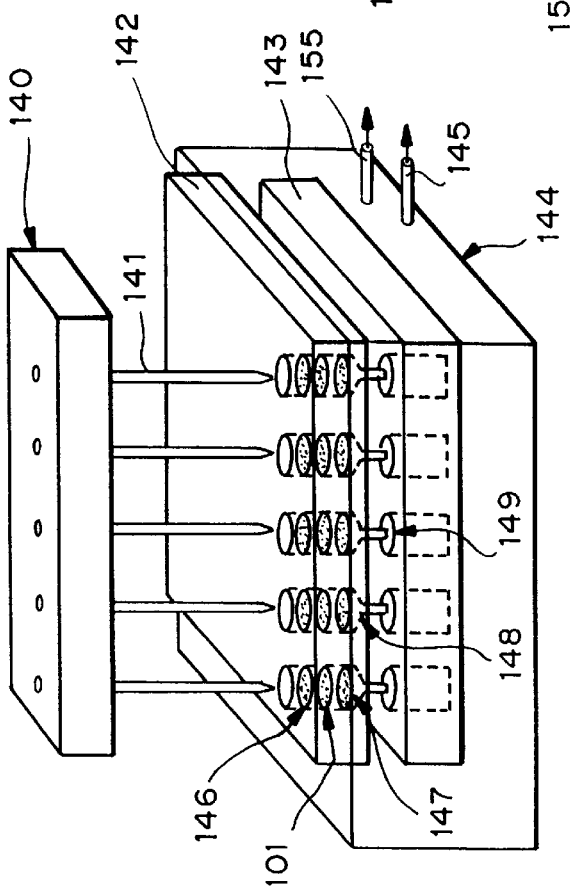

FIG. 6A is a schematic illustration of an apparatus for using microscale tissue arrays as part of a high-throughput flow system for chemical and biological testing, wherein the multi-well plate 142 is placed on top of a vacuum box 144 and a manifold system 140 is used to deliver fluid to each well at frequent intervals. A microscale tissue array 101 is placed in each well of the multi-well plate. The microscale tissue arrays may be held above the bottom of the wells through ridges, slots, or adhesive agent in each well. Filter material, such as nylon, cellulose, nitrocellulose, or PVDF, porous material, such as porous glass or porous silicon, or screens, such as metal screens, may be placed above 146 or below 147 each microscale tissue array. As in FIG. 5A, culture medium or test fluid is in direct contact with the top of the microscale tissue array and permeates the tissue array. If the microscale tissue array is held off the bottom of the well, a certain volume of culture medium or test fluid will occupy the space between the microscale tissue array and the bottom of the well.

In FIG. 6A, the vacuum box is configured with a gas inlet 155 and a gas outlet 145. A vacuum may be applied to the gas outlet, such that the fluid surrounding each microscale tissue array is brought through each well bottom, down through a funnel 148, and into the corresponding well 149 of a multi-well collection plate 143. Gas may be subsequently added to the vacuum box, providing a target gas phase composition and pressure in the box. The gas phase composition and pressure may be different than that of gas phase above the multi-well plate with the microscale tissue arrays. The gas phase compositions can be adjusted so as to provide the appropriate oxygen, pH, and carbon dioxide levels throughout the microscale tissue arrays.

In FIG. 6A, a manifold system 140 is used to deliver culture medium or test fluid to each well at frequent intervals. The fluid is delivered to each well through a small pipe or pipette tip 141. The fluid delivery system can be operated in concert with the vacuum system, such that the fluid volume in each well of the multi-well plate 142 is maintained constant or within an acceptable range. Fluid may be delivered across a broad range of intervals, such as from once per day to a few times per second. Appropriate flow conditions can be derived through design of the well geometry in the multi-well plate 142, selection of materials above 146 and below 147 the microscale tissue arrays based on flow resistance properties, design of the microscale tissue devices based on flow resistance properties, and design of the manifold and vacuum systems.

In FIG. 6A, the multi-well collection plate 143 can be removed from the vacuum box once fluid surrounding the microscale tissue arrays has been collected. The fluid in the collection plate can then be assayed and/or, through the use of the manifold delivery system, recycled back through the microscale tissue array from whence it came. When a collection plate with fluid is removed from the vacuum box, an empty collection plate can placed in the appropriate position in the box, ready to collect the fluid from the next flow cycle.

FIG. 6B is identical to FIG. 6A, except that an array of sensors 151 is used to detect events in each well. The signal from each sensor is sent through information lines 152 to a information display or processing device 150, such as a computer. Each sensor may consist of miniaturized fiber optic system, which provides single or multi-photon excitation to each microscale tissue and detects the resulting fluorescent intensity from the microscale tissue array. Other sensors may be used, such as ones which detect fluorescence, luminescence, or light absorption. Material with appropriate optical properties can be selected for use above 146 and below 147 the microscale tissue array. A large light source, or array of microscale light sources, can be placed within or below the vacuum box, such that each microscale tissue array is exposed to light from below. The tip of each sensor may be placed into the fluid above each microscale tissue array. Sensors which detect oxygen, pH, $CO_2$, or some other chemical entity may then be used. Sensors in the fluid above each microscale tissue array may also be used which detect the resistance to electron flow across the microscale tissue array. In this case, a miniature cathode or anode may extend into the fluid below each microscale tissue to complete a circuit with the respective sensor above the array.

In FIGS. 5A, 5B, 6A, and 6B, the composition of the filter, porous, or screen materials above or below the microscale tissue array should be selected so as to not bind particular chemical compounds or classes of compounds. The materials should not bind test compounds under study, their resulting metabolites, or key components of the culture medium, such as growth factors. Under many conditions, a filter composed of PVDF material fulfills this requirement. The materials may need to be precoated with certain compounds, such as albumin or collagen.

In FIGS. 5A, 5B, 6A, and 6B, the filter, porous, or screen materials below the microscale tissue array can be used which bind particular chemical compounds or classes of compounds. The materials may be such chosen or constructed so as to bind DNA molecules, DNA molecules with a particular sequence or sequences, RNA molecules, RNA molecules with a particular sequence or sequences, protein molecules, protein molecules with a particular composition or binding activity, and other biological molecules of interest. These molecules can then be captured from the fluid surrounding the microscale tissue arrays as it brought down into the collection plate through the vacuum operation. Alternatively, or in addition, these molecules can be extracted from the microscale tissue array in each well, according to standard extraction methods well known to those skilled in the art, and then captured from the extraction solution as it is brought down into the collection plate through the vacuum operation. Tests can then be performed to quantify or characterize the captured molecules.

Figure 7:
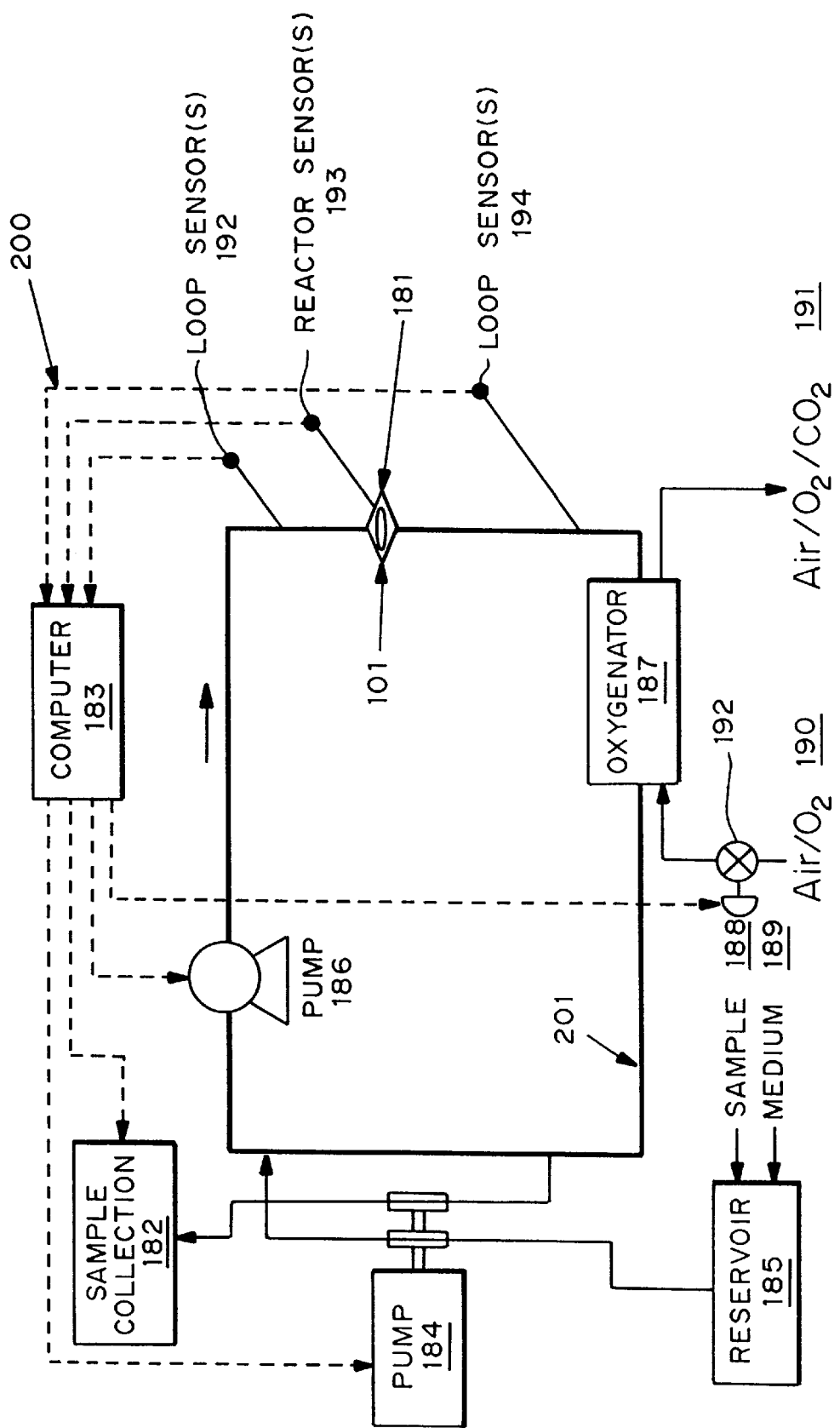
FIG. 7 is a process flow diagram showing an apparatus for using a microscale tissue array as part of a continuous flow system for chemical and biological testing.

FIG. 7 is a schematic illustration of an apparatus for using a microscale tissue array 101 as part of a continuous flow system for chemical and/or biological testing. Culture medium containing a test substance is circulated by a pump 186 through a microscale tissue array 101 contained within a reactor housing 181. The circulation rate can be controlled by a computer 183 connected to the circulation pump. The fluid recycles around a continuous flow loop 201 which, if necessary for gas exchange, can contain a flow-through oxygenator 187 which supplies oxygen and removes carbon dioxide. In certain circumstances, gas exchange through the walls of the loop tubing may be sufficient to eliminate the need for the oxygenator. The oxygenator contains gas permeable tubing, in sufficient quantity to allow for the required gas exchange with the oxygenator inlet gas 190. Oxygen transfers from the gas into the medium, while carbon dioxide transfers from the medium into the gas and is carried away as part of the exit gas 191. The flow rate of the inlet gas can be controlled through the use of a control valve 192 connected to a computer control system 183.

In FIG. 7, the composition of the circulating medium can be assessed through the use of sensors upstream 192 and/or downstream 194 of the microscale tissue array. Numerous sensors may be used at either position, including sensors which measure oxygen, pH, glucose, carbon dioxide, test substances, metabolites of test substances, or other critical biological parameters. A reactor sensor 193 can be used which penetrates through the reactor housing. The reactor sensor may consist of miniaturized fiber optic system, which provides single or multi-photon excitation to each microscale tissue and detects the resulting fluorescent intensity from the microscale tissue array. Other sensors may be used, such as ones which detect fluorescence, luminescence, light absorption, or the resistance to electron flow across the microscale tissue array.

In FIG. 7, the test sample 188 and culture medium 189 are mixed in a feed reservoir 185 in proportions so as to provide an appropriate sample concentration. The proportions may be controlled on line by the computer 183 potentially as part of a feedback control scheme. The resulting medium/sample mixture is fed by a feed/bleed pump 184 into the circulation loop. Fluid can be simultaneously removed from the circulation loop through a second head on the feed/bleed pump, such that the volume of fluid in the circulation loop is held essentially constant. The fluid removed can be sent to waste or a sample collection device 182. The sample collection device can consist of a fraction collector, of the type commonly employed in chromatography systems, operated under control of the computer and/or its own internal control program. With a fraction collector, samples taken within certain time intervals can be loaded into separate collection tubes. The samples can be subsequently analyzed for the test compound or other chemicals.

Figure 8:
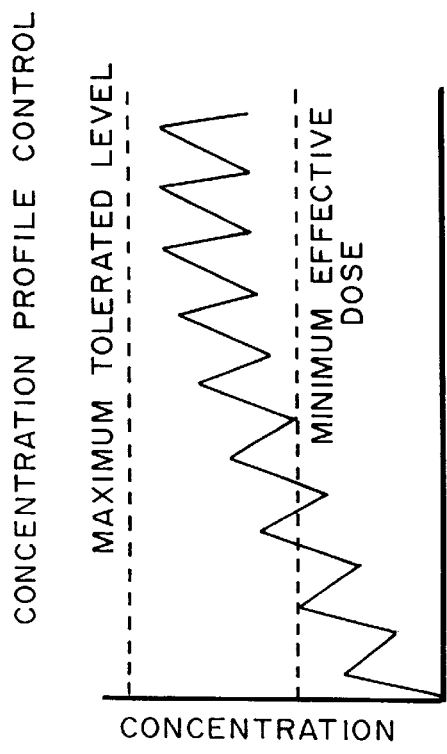
FIG. 8 is a graph illustrating a test target drug concentration profile over time, as can be provided through the use of the continuous flow system depicted in FIG. 7.

In FIG. 7, the operation of the entire continuous flow test system can be controlled by a computer 183. Feedback control schemes may be executed based on readings from the sensors or results from tests run on samples. A control scheme can be implemented to provide a target profile concentration versus time, such as shown in FIG. 8, for a test chemical or biological agent.

Alternatively, a control scheme may be implemented to provide a target profile of reaction rate versus time for a reaction occurring in the microscale tissue array. The rate could be assessed continuously through the use of the upstream and downstream sensors. The continuous flow system depicted in FIG. 7 is highly flexible and can be operated according to a wide variety of control schemes.

Figure 9:
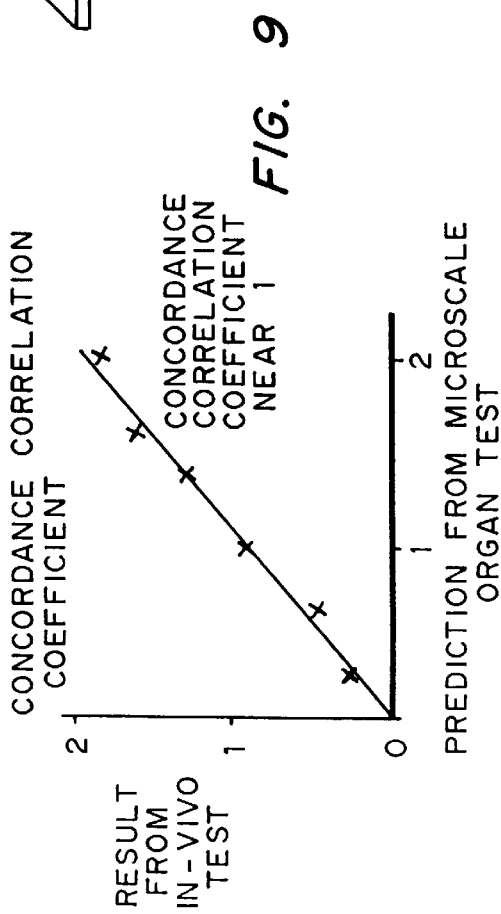
FIG. 9 is a graph illustrating the correlation coefficient between an in vivo test and the prediction from a microscale organ test.

FIG. 9 illustrates a set of results from a validation study concerning the qualification of a microscale tissue array as a microscale organ array. In such a study, the effect of a chemical or biological agent on a particular characteristic of a microscale tissue array is determined through the use of an appropriate test system, such as those illustrated in FIGS. 5A, 5B, 6A, 6B, or 7. The results from the test are entered in to an appropriate scale-up model to predict the effect of the agent on an organ in vivo. The prediction is then compared to the result from a separate study which determines the effect of the agent on the particular characteristic of an isolated organ perfused in vivo. The microscale tissue test, corresponding prediction and corresponding in vivo assessment are performed across a range of agent concentrations and/or compositions. The results are plotted on a graph, as shown in FIG. 9, and the concordance correlation coefficient is determined. If the concordance correlation coefficient is near 1 or at least above an acceptable lower limit, the microscale tissue array used in the respective test system qualifies as a microscale organ array for the particular characteristic tested.

Figure 10:
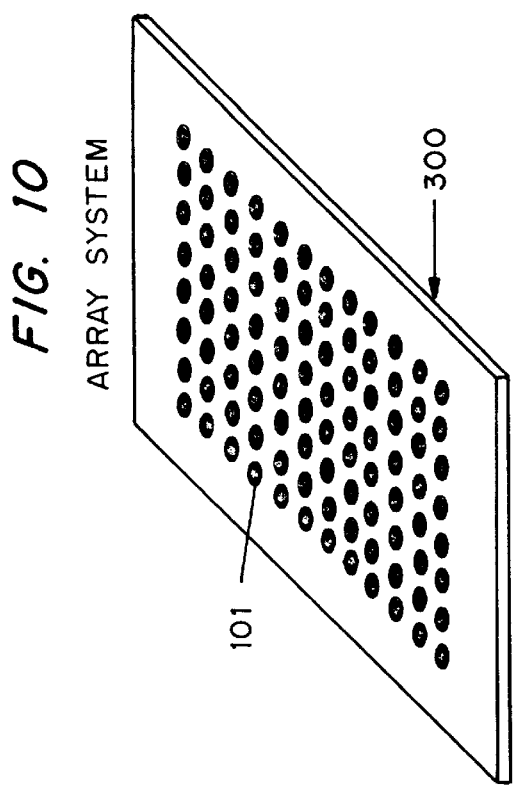
FIG. 10 is a schematic of an array of microscale tissue arrays.

FIG. 10 is an array of microscale tissue arrays. A series of microscale tissue arrays was constructed out of a single piece of substrate 300, which may be made of, but not limited to, silicon, polymeric material, or other suitable materials. The resulting fabrication can be placed, with appropriate gaskets, into a housing with multiple chambers such that each microscale tissue array 101 is contained within a well. Filter material, porous material, or screens may be incorporated into the housing so as to occupy a position above and/or below each microscale tissue array. The resulting device is analogous to a multi-well plate and can be used in systems such as those shown in FIGS. 5A, 5B, 6A, or 6B.

Figure 12A:
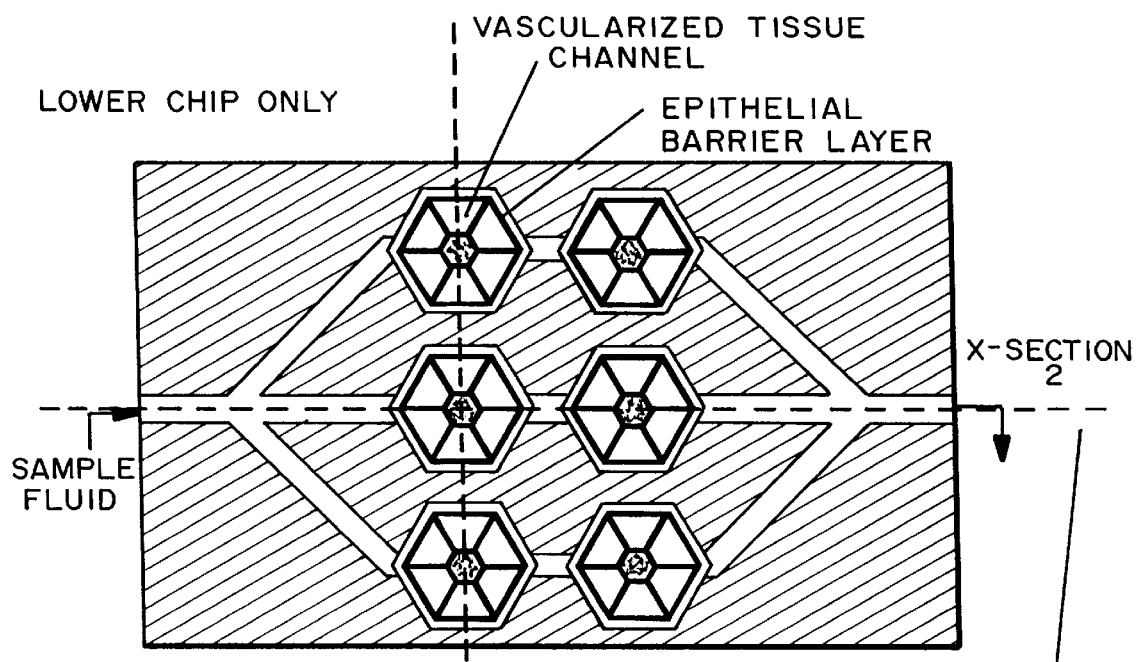
FIGS. 12A and 12B are schematics of the design of an epithelial barrier layer construction using 2 chips, a lower chip with vascularized tissue channels (FIG. 12A), and cross-sectional views of the upper and lower chips showing the connections between the open channels and the epithelial barrier (FIG. 12B).
Figure 12B:
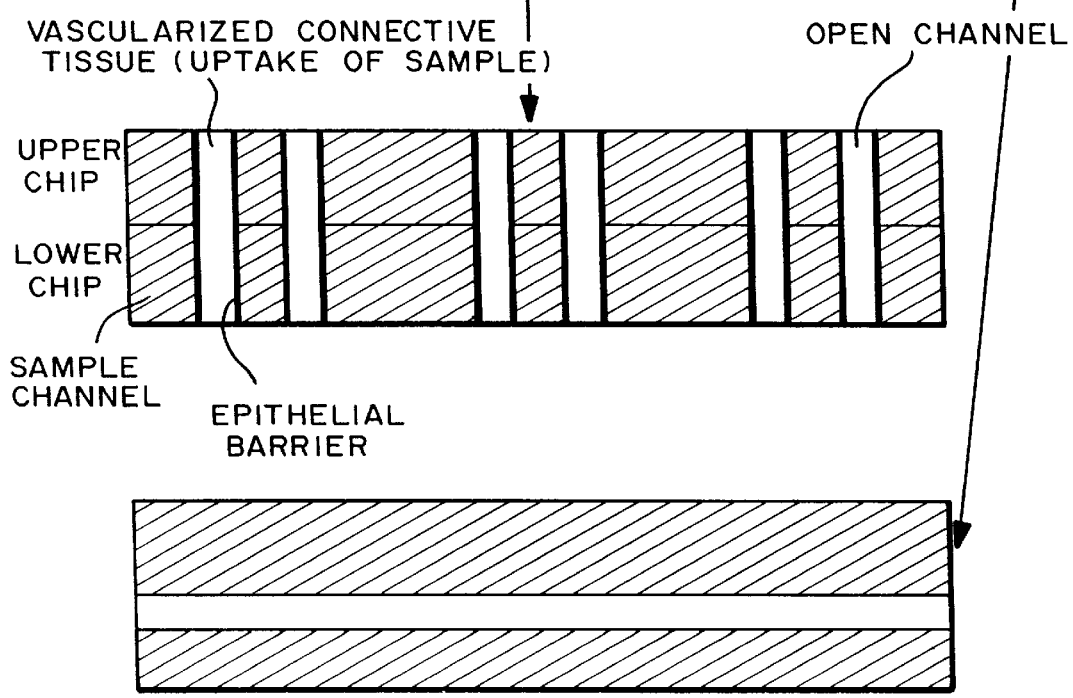

FIG. 12 is a schematic of the design of an epithelial barrier layer construction using two chips. FIG. 12A shows the lower chip 200 showing six channels 202 to form vascularized tissues 204 in the core of the channels 202, surrounded by epithelial tissue 206. As shown by the cross-sectional view in FIG. 12B, the sample is applied via sample channel 208 in lower chip 200, which connects with upper chip 210. The epithelial barrier layer 206 separates the sample from the vascularized channel 202, equivalent to applying a sample to vascularized tissue.

IV. Testing of Materials in the Microtissue or Micro-Organ Systems

Many different materials can be tested using these devices. These can be administered directly to the cells or indirectly via perfusion. The materials can be compounds which affect the cells, or potentially affect the cells (for example, a drug which has desirable effects may first be tested in these devices for toxicity), to see if the cells degrade the materials (for example, to predict in vivo half-lives), or infected by a virus, bacteria or other pathogen, then treated with a material to look at the effect.

Test systems using microscale tissue arrays have a broad range of uses for in vitro assays. Using the arrays, one can study biotransformation, clearance, metabolism, and activation of xenobiotics. The bioavailability and transport of chemical and biological agents across epithelial layers and across the blood-brain barrier can be studied. The acute basal toxicity, acute local toxicity or acute organ-specific toxicity, teratogenicity, genotoxicity, carcinogenicity, and mutagenicity, of chemical agents can also be studied. Infectious biological agents, biological weapons, harmful chemical agents and chemical weapons can be detected. Infectious diseases and the efficacy of chemical and biological agents to treat these diseases, as well as optimal dosage ranges for these agents, can be studied. The response of organs in vivo to chemical and biological agents, and the pharmacokinetics and pharmacodynamics of these agents can be predicted. The impact of genetic content on response to the agents can be studied.

The amount of protein expression in response to chemical or biological agents can be determined. Changes in metabolism in response to chemical or biological agents can be studied. The impact of agents can be predicted through database systems and associated models, expert systems or structure-based models.

Specific representative assays are described below.
1. Studies on Gene Transcription in Response to Chemical or Biological Agents Filter or porous material below microscale tissue may be chosen or constructed so as bind denatured, single-stranded DNA. Nitrocellulose filters can be used in this manner. The captured DNA can then be characterized through hybridization techniques using oligonucleotide probes. Alternatively, the filter or porous material may contain immobilized probes which capture denatured, single stranded DNA with specific sequences. The captured DNA may be analyzed in place or after subsequent release, and may be amplified through PCR or other similar techniques. Alternatively, the microscale tissue may be contained in each sample well of a flowthrough genosensor. These genosensors are illustrated on page 218 of Doktycz, et al., "Genosensors and Model Hybridization Studies" in *Automation Technologies for Genome Characterization*, T. J. Beugelsdijk, ed. (John Wiley & Sons, New York 1997).

Filter or porous material below microscale tissue may be chosen or constructed so as to bind RNA. Chemically-treated cellulose filters, nylon filters, and under certain circumstances, nitrocellulose filters, fulfill this requirement. The captured RNA can then be characterized through hybridization techniques using oligonucleotide probes. Alternatively, the filter or porous material may contain immobilized probes which capture denatured, single-stranded RNA with specific sequences. The captured RNA may be analyzed in place or after subsequent release, and may be amplified through PCR or other similar techniques. Alternatively, the microscale tissue may be contained in each sample well of a flowthrough genosensor. These genosensors are illustrated on page 218 of Doktycz, et al., "Genosensors and Model Hybridization Studies" in *Automation Technologies for Genome Characterization*, T. J. Beugelsdijk, ed., (John Wiley & Sons, New York 1997).

2. Analysis of Metabolites

Toxic substances, including compounds that are intrinsically toxic to all cells (e.g., cyanide) and those that are metabolically converted to toxic metabolites (usually electrophiles) by parenchymal cells, can also be detected using a comprehensive approach to detect an event that will lead to cell death. This can be general and not specific; i.e., not specific for an individual toxin, but general for the entire class. Examples include mitochondrial poisons, DNA-damaging agents, and membrane-damaging agents.

Metabolite detection may be achieved by monitoring the fluid effluent from the micro-organ using in-line detection methods such as UV, visible, or fluorescence detectors and/or mass spectrometry. In addition, the effluent from micro-organs can be sampled periodically and analyzed for the presence of metabolites in an off-line fashion using standard analytical techniques.

The filter or porous material below the micro-organ may be designed to incorporate trapping agents and/or substrates as a method for detecting metabolites. These trapping agents (i.e. peptides or nucleophilic organic species) would be exposed to the fluid emanating from the micro-organs and would covalently bond to reactive metabolites generated by the micro-organs and released into the perfusate. The complex formed by covalent linkage of the trapping agent and the reactive metabolite could then be detected in-situ or could be released from the filter or porous material by cleavage of a labile bond connecting the trapping agent to the filter or porous material. This labile bond could be cleaved by chemical means, the activity or an enzyme, or by the exposure of specific wavelengths of light.

3. Detection of Viral or Other Pathogen Infection

Detection of viral or other pathogen infection presents greater challenges as the time course of infection is relatively long and cellular changes may be subtle. The inability to transmit hepatitis B virus (HBV) and hepatitis C virus (HCV) infection to laboratory animals other than chimpanzees or to propagate the virus in cell lines has severely hampered efforts to understand the life cycle of HBV and HCV. The major hypothesis is that HBV and HCV will infect and replicate in primary human hepatocytes that are sufficiently differentiated to maintain viral cell surface receptors and transcription factors required for initiation of complete viral replicate life cycle within the cell. Thus, HBV and HCV represent very good generic models of potential pathogens which require higher-order tissue function in order for pathogenicity to be detected, regardless of whether the pathogen is known or unknown.

Three potential fluorescent readouts of infection, each as a function of the time course, are cytosolic enzyme leakage, cytosolic NAD(P)H reduction, and expression of GFP linked to stress-inducible promoters in either endothelial cells or hepatocytes.

Hepatitis B virus is the prototype member of the hepadnavirus family, a group of enveloped DNA virus that primarily infect the liver (Moradpour, et al., *New Engl. J. Med.* 332:1092–93 (1995)). The HBV genome consists of a partially double-stranded 3.2 kb DNA molecule arranged in a relaxed circular conformation. Sequence analysis of the genome reveals that HBV encodes four partially overlapping open reading frames (ORF) that direct the synthesis of at least seven viral gene products. Viral RNA, DNA, and protein expression can be examined in primary human hepatocyte cultures infected or transfected with HBV (Li, et al., *J. Virol.* 70:6029–35 (1996); Scaglioni, et al., *J. Virol.* 71:345–353 (1997); Melegari, et al., *J. Virol.* 71:5449–54 (1997)). The molecular confirmation of HBV replication and propagation can be based on the following measurements:

a) RT-PCR of plus and minus strand HBV-DNA;
b) RNAse protection assays of 2.1 and 3.5 pregenomic RNA species;
c) Encapsidation of pregenomic RNA into core particles; and
d) Secretion of hepatitis B surface antigen (HBsAg), hepatitis B core antigen (HBcAg) and hepatitis B e antigen (HBeAg) in the culture medium by radioimmunoassay and detection of viral proteins in cells by immunohistochemistry.

In brief, primary human hepatocyte cultures are incubated with HBV particles for 24 h. culture medium and cells are then sampled at various times up to two months. Transfection studies can be performed with a full-length HBV-DNA clone using cationic liposomes to assure that human hepatocytes can support HBV replication using methods described by Moradpour, et al., *Hapatology* 22:1527–37 (1995). Viral replication can be detected using monoclonal anti-HBV capture followed by PCR analysis. Intact virions are captured by a high infinity monoclonal antibody directed against the envelope protein linked to a solid phase support followed by heat denaturation to release viral DNA. The viral DNA is detected by PCR analysis using primers derived from the envelope, core and polymerase gene regions (Liang, et al., *J. Clin. Invest.* 84:1367–71 (1989)). Viral infection and replication can commence two to three weeks after inoculation. The early steps of the viral life cycle can be investigated, which previously has not been possible to investigate in a primary cell culture system (Li, et al., *J. Virol.* 70:6029–35).

Hepatitis C virus is a positive strand RNA virus with a genome length of about 9.5 kb. One large open reading frame codes for a polyprotein precursor of about 3000 amino acids which is processed by a combination of host and viral proteases into at least 10 different structural and nonstructural proteins (Wakita, et al., *J. Biol. Chem.* 269:14205–10 (1994)). Monoclonal antibodies against the NS3 (viral specific serine protease) and NS5 (RNA polymerase) nonstructural proteins of HCV (Geissler, et al., *J. Immunol.* 158:1231–37 (1997); Encke, et al., *J. Immunol.* 161(9):4917–23 (1998)) have been prepared. All of the structural and non-structural genes have been inserted into suitable expression vectors in order to produce probes for in situ hybridization of infected cells. The molecular confirmation of HCV replication and propagation can be based on the following measurements:

a) RT-PCR analysis of plus and minus strand viral RNA using primers derived from the highly conserved 5' non-coding and core regions of the genome.

b) Assess gene expression by in situ hybridization using probes derived from the core and NS3 and NS5 gene regions.

c) Examine protein expression by immunohistochemistry using monoclonal antibodies against recombinant core, NS3 and NS5 proteins.

Primary human hepatocyte cultures can be incubated with $1 \times 10^6$ HCV genomes as measured by semi-quantitative PCR assay. Cell culture medium and hepatocytes can be analyzed for HCV replication by analysis of positive and negative strand viral RNA using RT-PCR. Hepatocytes can be examined for viral RNA gene expression by in situ hybridization using probes specific for structural and non-structural genes. Expression of both structural and nonstructural proteins can be detected by immunohistochemistry of infected cells. The hepatocyte culture system can support HCV replication at a low level and the replicative life cycle of HCV can be at least partially characterized.

Fluorescent Readouts of Infection

Hepatitis infection is associated with elevation of liver enzymes in the blood due to cytosolic leakage from hepatocytes. Thus, the two approaches described for assessing effects of toxins, NAD(P)H levels and membrane leakage, may also provide readouts of viral infection.

Very early events in viral infection may lead to an increased expression of stress-inducible promoters in either hepatocytes or endothelial cells. These events can be detected by liking these promoters to GFP or a new more sensitive reporter, β-lactamase (Zlokarnik, et al., *Science* 279:84–87 (1998)). Lee, et al. have cloned the Egr-1 promoter 5' to the gene for enhanced green fluorescent protein (eGFP) in an expression plasmid, and demonstrated that primary endothelial cells transfected with this construct exhibit rapid gene induction at the eGFP wavelength following mechanical stimulation. Although the Egr-1 promoter is commonly associated with mechanical stress, expression is also stimulated during active viral infection (Tatarowicz, et al., *J. Neurovirol.* 3:212–24 (1997)). Notably, it has been shown that the Egr-1 protein associates with the hepatitis B virus X (HBx) protein, allowing Hbx to participate in the regulation of immediate-early genes (Yoo, et al., *J. Clin. Invest.* 97:388–95 (1996)).

Infection via stress-inducible promoters can be detected by at least two methods. The existing system developed by Lee, constructs of Erg-1/GFP and Erg-1/β-lactamase transfected into primary endothelial cells, can be used to assess whether viral infection in 3D perfused liver cultures can be detected via stress on the sinusoidal endothelial cells. The same Erg-1 constructs can be transfected into primary human hepatocytes. Transfection efficiency and expression can be screened by stressing the cells mechanically or osmotically under standard (petri-dish) culture techniques. Low transfection efficiencies can be tolerated because each sensor contains thousands of cells, and the readout is change in total fluorescent intensity. Once a transfection protocol is established for the primary hepatocytes, transfected cells can be tested in the perfusion tissue sensor. A readout can be provided which gives a signal within a few minutes or hours of applying the sample. In the event that Erg-1 readout is present but occurs relatively late in the infection process, a variety of other known stress-inducible promoters can be screened.

4. Assays for Cytotoxicity

Biological toxins act by different mechanisms and may exhibit different sensitivities and time courses of actions compared to chemical toxins. Biological toxins can be evaluated for their effects on both liver and ES cells. Representative examples include Shiga-like toxin (SLT or verotoxin), produced by Enterohemorrhagic *Escherichia coli* (EHEC), and Vac (vacuolating toxin), produced by *Helicobacter pylori*. SLT stops host cell protein synthesis by inactivating the 60S subunit of host cell ribosomes (Tesh, et al., *Mol. Microbiol.* 5:1817–22 (1991)). Vac toxin binds to cells through an unknown receptor, and induces vacuole formation, probably by inhibiting sodium-potassium ATPase activity.

The technical challenges associated with monitoring cytotoxicity in real time within the context of this dynamic tissue sensor can be met using a variety of Laser Induced Fluorescence (LIF) techniques. LIF provides detection limits in the low femtomoles ($10^{-15}$ moles), and for ideal analytes, attomole ($10^{-18}$ moles) detection limits are possible. Two primary endpoints have been identified for monitoring the effects of toxic insult to the tissue sensor: decrease in NAD(P)H levels within the cells and a loss of cellular membrane integrity.

A decrease in intracellular NAD(P)H in response to toxin exposure is observed in the case of mitochondrial poisons (e.g., menadione or cyanide) due to disruption of the respiratory chain. Intracellular NADH and NAD(P)H levels are also depleted in response to nuclear toxins (e.g., nitrogen mustards) via the process of poly ADP-ribosylation of proteins associated with DNA. The cellular pool of NAD(P)H can be monitored by in-situ fluorescence spectroscopy as described above for fluctuations in response to toxin or pro-toxin exposure.

A loss of membrane integrity is a common endpoint for all cytotoxic pathways (i.e., necrosis or apoptosis) and can be observed after all cytolethal exposures to the tissue-based sensor. The loss of membrane integrity is accompanied by a leakage of intracellular constituents into the perfusate. One approach to capitalize on this loss of membrane integrity can be to load the cells of the bio-sensor with poly-esterified derivatives of fluorescein (e.g., Calcein AM, Abs: 494 Em: 517). These non-fluorescent derivatives passively enter the cells after which esterases hydrolyze them to poly-anionic fluorescent dyes that are retained in the cells. An increase in cell membrane permeability due to a toxic insult can lead to loss of dye to the perfusate. Thus, monitoring a decrease in fluorescence of the dye retained by the cells can provide a readout of cytotoxicity.

Another approach to quantify cytotoxicity by loss of membrane integrity can be to observe an increase in enzymatic activity (e.g., alkaline phosphatase and γ-glutamyl transpeptidase) released into the perfusate. This can be accomplished through LIF spectroscopy of an in-line enzyme detector consisting of immobilized pro-fluorophore or pro-chromophore enzyme substrates.

For example, this approach could be used to monitor γ-glutamyl transpeptidase activity released into the perfusate by micro-organ array after toxic insult. A rhodamine derivative has been designed that is non-fluorescent until the action of γ-glutamyl transpeptidase liberates the free amine. The resulting product is highly fluorescent (Abs: 492 Em: 529) and remains bound to the solid support. The use of an in-line immobilized substrate allows for monitoring a cumulative signal and dramatically improves the sensitivity, as compared to detecting the signal from a soluble fluorophore circulating in the perfusate. A similar strategy can be employed to monitor alkaline phosphatase activity using an immobilized fluorescein diphosphate derivative.

One configuration of in-line detector involves immobilizing the pro-fluorophore and/or pro-chromophore enzyme substrate(s) onto the filter or porous material situated below each micro-organ. A micro-organ array (e.g. as illustrated in FIGS. 5, 6, and 10) would therefore contain an array of filter immobilized pro-fluorophores/chromophores tailored to react to specific cellular responses emanating from each micro-organ. Such a filter array can be designed to include substrates that respond with varying sensitivities to the same cellular response and substrates that respond to different cellular responses. In addition, redundancy (i.e., the same pro-fluorophore/chromophore present under more than one micro-organ within an array) can be distributed throughout the micro-organ array. The pro-fluorophores/chromophores are designed to respond to numerous cellular responses including but not limited to enzyme leakage from the cells, fluctuations in effluent pH, and release of reactive oxygen species.

The fluorescence signal produced by each filter or porous material is proportionate to the extent of the cellular response. The array of filters or porous materials would demonstrate a characteristic fluorescence intensity pattern that would be indicative of the status of the micro-organ array. The fluorescence signal from the array can be collected on a periodic basis as necessary using the instrumentation outlined above in the section describing sensors. The data obtained from the array of fluorophores can be interpreted by pattern recognition software to correlate the fluorescence signal pattern to the status of the micro-organ array.

V. Use of the System as a Bioreactor

Figure 11:
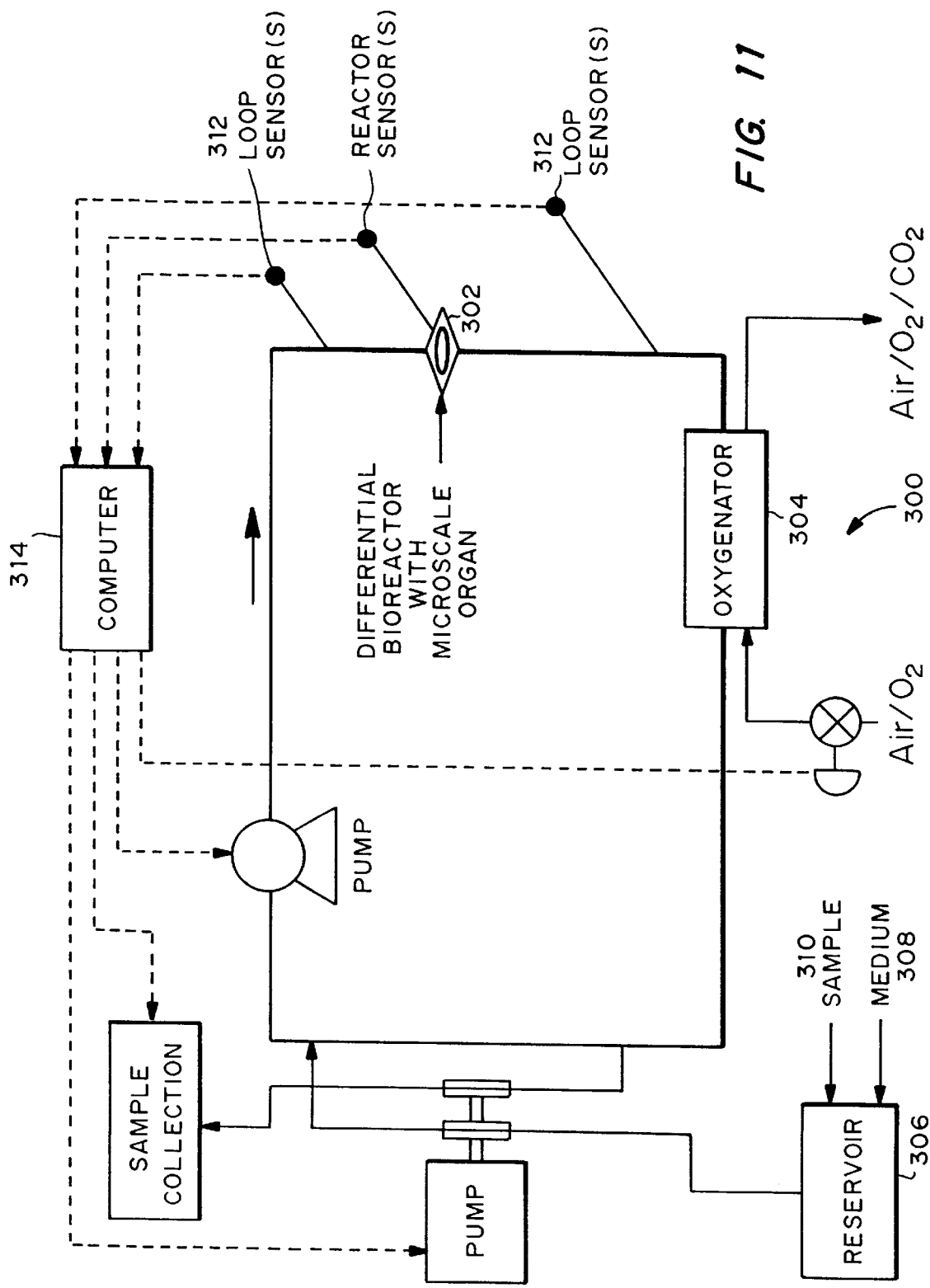
FIG. 11 is a process flow diagram of a differential bioreactor.

An example of a suitable bioreactor is shown in FIG. 11. In the bioreactor 300, a microscale organ 302 is provided, along with an oxygenator 304, a reservoir 306 providing nutrient medium 308, and a sample of an agent 310 to be processed by the organ. The medium and the agent are pumped through the organ, and samples collected as desired. Various sensors 312 are included at different portions of the loop. The system is controlled by a computer 314.

The present invention will be further understood by reference to the following non-limiting examples.

EXAMPLE 1

Scaffold Design and Fabrication

An initial set of scaffolds has been fabricated using the ICP deep-trench etching approach to define appropriate etch times, photoresist properties, and the appearance of the resulting channels. Small channels etch more slowly than large channels and thus small channels determine the etch time. Because the channel dimensions which are optimal for production of tissue are unknown, a combinatorial approach was taken in designing the array. Two channel geometries were considered (square-cornered channels and round-cornered channels) and the channel dimensions for each systematically varied over the range of 75 to 600 $\mu$m.

Discs were etched then polished to a final thickness of 300 $\mu$m. The channels in the scaffolds were visualized by SEM, which showed that the channel cross sections show fidelity to the mask pattern, that the walls are vertical, and that only very slight (less than 1 $\mu$m) texture is present on the surface of the channels. These results indicate that the sorts of complex patterns depicted in FIGS. 3A and 3B will be possible to produce by ICP deep-trench etching and that faceting does not occur to any observable extent. The discs were cleaned in acid and macroporous filters (plasma-treated PDVF, nominal pore size of 5 $\mu$m) were bonded to one side of the disc using a thermal process which leaves the filter pore structure intact. Filters remained stably attached after a standard cell-seeking process in which the scaffold is placed in a syringe filter holder and a cell suspension is slowly forced into the scaffold from a syringe.

The use of PEG brushes to inhibit protein adsorption and cell adhesion is well-accepted in the biomaterials literature. The relationships between grafting conditions and the achievable chain densities and resulting protein resistance have been delineated in several previous studies (Irvine, et al., *Macromolecules* 29: 6037–43 (1996); Irvine, et al., *J. Biomed. Mat. Res.* 40:498–509 (1998); Walton, et al., *Macromolecules* 30:6947–56 (1997)). Laibinis et al. have developed a family of new organotrichlorosilanes, $CH_3(OCH_2CH_2O)_{2,3}(CH_2)_{11}SiCl_3$, which allow more facile treatment of Si surfaces to product stable, non-adsorptive surface layers which inhibit cell adhesion in serum-containing and serum-free medium (Lee & Laibinis, *Biomaterials* 19:1669–75 (1998)). The feasibility of tethering growth factors to silicon substrates has been demonstrated for a practical prototype, epidermal growth factor (EGF) (Kuhl, et al., *Nature Med.* 2:1022–27 (1996)). Tethered EGF retained full biological activity and could be used to stimulate cells in a dose-dependent manner, as well as to induce changes in cell morphology.

EXAMPLE 2

Liver Cell Isolation and Culture

A reproducible and readily available source of primary (i.e., tissue-derived) cells for forming tissue was developed using rat cells. Liver parenchyma comprises four major cell types: hepatocytes, endothelial cells, macrophages (Kupffer cells), and stellate cells (fibroblast-like cells). Isolated suspensions of each cell type were prepared and combined in defined proportions to create the tissue. The minimal two cell types, hepatocytes and endothelial cells, were the initial focus. The standard procedure for isolating primary hepatocytes (the 2-step Seglen perfusion method) produces a cell population comprising 95–99% hepatocytes, with the purification based primarily on the significant size difference between hepatocytes (about 25 $\mu$m diameter) and the other cell types (10–12 $\mu$m diameter). A mixed fraction of the non-hepatocyte cell types (typically referred to as "non-parenchymal cells") can be obtained from the same cell isolation, but purification of the individual cell types from this mixture requires many steps. Therefore, the use of a more readily available primary endothelial cell source, bovine aortic endothelial cells (BAECs), was investigated. The culture experiments described below were carried out using mixtures of primary rat hepatocytes and BAECs. All culture experiments in both petri dish culture and 3D reactor configurations were carried out in a serum-free culture medium optimized for hepatocytes, "HGM", based on DMEM with added EGF, transferrin, selinium, insulin, dexamethasone, galactose, nicotinamide, pyruvate, and L-glutamine.

Due to the potential incompatibility of primary rat hepatocytes with bovine endothelial cells, the behavior of BAECs was compared with two different sources of primary rat microvascular endothelial cells using morphology of primary co-cultures of rat hepatocytes with the test endothelial cells in petri-dish culture as an indicator of differences in the performance of the endothelial cell types. Rat lung microvascular endothelial cells are available from commercial vendors, such as Vascular Endothelial Cell Technologies (Renssalear, N.Y., USA) and are reported to maintain their phenotype over multiple subcultures. Co-cultures of primary rat hepatocytes with either bovine aortic endothelial cells or rat lung microvascular endothelial cells were prepared. Each cell type was seeded at a density of $3 \times 10^4$ cells/cm$^2$. Cells were cultured on polystyrene petri dishes coated with 3 µg/ml or 0.03 µg/ml type I collagen. Phase contrast micrographs were taken after 1, 3, or 5 days in culture. Phase contrast images of co-cultures show that the rat endothelial cells integrated with the hepatocytes to a much greater extent and lead to the formation of more tissue-like architectures than the bovine aortic endothelial/hepatocyte cell cultures.

Protocols to isolate and culture rat sinusoidal endothelial cells also were developed, because rat lung endothelial cells exhibit rapid proliferation even in the serum-free medium optimized for hepatocytes and the phenotype characteristic of lung may persist even when they are in contact with hepatocytes. Rat liver sinusoidal endothelial cells were isolated form the nonparenchymal cell supernatant through a two-step Percoll gradient and a selective cell adhesion. Rat liver sinusoidal endothelial cells and Kupffer cells migrate together to the region between a 1.037 g/ml and 1.066 g/ml Percoll cushion. Because Kupffer cells attach to tissue culture plastic in 15 minutes while endothelial cells require 1–2 hr, seeding the mixed fraction on tissue culture plates allows for purification of the endothelial cell fraction. Following the 15 minute Kupffer cell attachment, the medium containing the unattached endothelial cell fraction was removed and reseeded in separate plates.

The endothelial cell fraction did not attach to tissue culture plastic so attachment to extracellular matrix (ECM)-coated plates was tested. Endothelial cells did not attach to plates coated with 5 µg/ml fibronectin, but exhibited attachment to 5 µg/ml Amgel- or Matrigel-coated surfaces. However, cell detachments began within 36 hours, with 90% detachment occurring after 72 hours. It therefore may be preferred to maintain the cells within gels rather than on gels.

EXAMPLE 3

Tissue Engineering

Mixtures of primary rat hepatocytes and bovine aortic endothelial cells seeded into the channels of biodegradable polymer scaffolds were observed to show histotypic reorganization of the cells over the first two days in culture, with endothelial cells sorting to the fluid-tissue interface as predicted by Steinberg, et al., *Proc. Natl. Acad. Sci. USA* 91:206–09 (1994). The macroscopic appearance of a "cord" of hepatocytes and endothelial cells spanning the corner of an 800×800 µm channel made of biodegradable polyester was examined and the observed structure is similar to the native cords in liver, in which a plate of hepatocytes is lined by sinusoidal endothelium. Although occasionally tissue-like cell densities could be achieved, the total cell density in the scaffold was generally lower than that in tissue; the scaffolds were relatively large (approximately 0.5 cm$^3$, about 100-fold greater in volume than the proposed scaffolds) and contained many different microenvironments. The hepatocytes maintained in these scaffolds under perfusion conditions maintained metabolic function for the two-week studies as assessed by secretion of albumin into the medium.

Biophysical parameters affecting tissue organization were defined by investigating biophysics of hepatocytes, endothelial cells, and co-cultures on defined 2-D substrata. The morphology of hepatocyte aggregates cultured on 2-D substrata were either spheroidal or spread ("monolayer"), demonstrating that morphology was dictated by a balance of cell-substrate adhesion forces and cell contractile strength (Powers, et al., *Biotech. Bioeng.* 53:415–26 (1997)). These studies have since been expanded to include hepatocyte and endothelial cell co-cultures. The morphogenetic and organizational behavior of these cells in vitro can be predictably modified through variation in substrate adhesive properties (i.e., adsorbed extracellular matrix concentration). The resulting structures consist of cell types which sort from one another as monolayers (high adhesion strength), multilayers (intermediate adhesion strength), or spheroids (low adhesion strength) depending on the relative differential affinities of the cell—cell and cell-substratum interactions which are present in the culture system. These results indicate that the formation of liver tissue structures may be possible through simple modulation of the biophysical features of the substratum.

Preliminary work suggests that the channels in silicon wafers processed by ICP deep-trench etching are also conducive to histotypic tissue organization. Endothelial cells readily attach to the walls of these channels and form structures which are capable of spanning across the channel lumens. Similar results are observed when the silicon wafers are seeded with hepatocytes.

EXAMPLE 4

Metabolic Activity of Perfused Micro-Organ

The metabolic activity of perfused micro-organs established in the channels of silicon wafers using probe substrates for enzymatic activity (specifically the activity of Cytochrome P450 enzymes) were evaluated. These micro-organs contained primary hepatocytes and endothelial cells that had undergone a period of reorganization within the channels of the silicon wafers. The assay involved dissolving the enzyme substrate into chemically defined media and perfusing it through the micro-organ array maintained within a configuration such as illustrated in FIG. 7. The effluent from the perfused micro-organ array was collected in sequential fractions and these fractions analyzed by fluorescence detection for the presence of metabolite.

Figure 13:
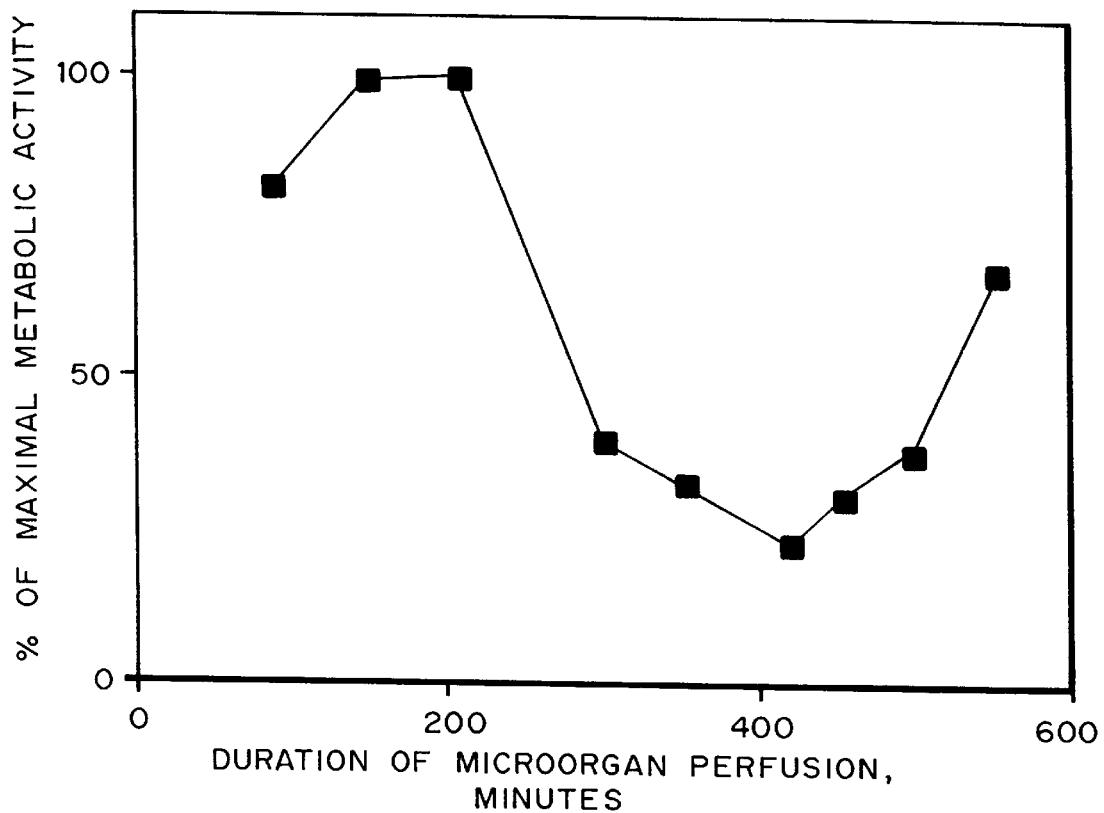
FIG. 13 is a graph illustrating metabolic activity data collected in the laboratory from a micro-organ array consisting of hepatocytes and endothelial cells situated within the channels of a silicon wafer, plotted as percent of maximal metabolic activity versus duration of micro-organ perfusion in minutes. Metabolic activity was determined by quantifying metabolite present in the micro-organ array perfusate. The micro-organ array was perfused with media containing a probe substrate for enzymatic activity in the absence of any inhibitors of enzymatic activity (t=0–240 minutes), in the presence of inhibitor (t=240–385 minutes) and then again in the absence of inhibitor (t=385–585 minutes).

FIG. 13 shows representative results for this type of assay. In this case, the micro-organ array was perfused with media containing a probe substrate for enzymatic activity in the absence of any inhibitors of enzymatic activity (t=0–240 minutes), in the presence of inhibitor (t=240–385 minutes) and then again in the absence of inhibitor (t=385–585 minutes). Metabolic activity paralleled the inhibitor concentration.

These experiments demonstrate that the micro-organ arrays readily metabolize compounds introduced into the perfusion media and achieve a steady state level of enzymatic activity. Further, the enzyme activity was inhibited by the inclusion of a reversible inhibitor to the perfusion media and then recovered when the inhibitor was removed. Importantly, the cells in the micro-organ arrays respond to their environment and actively metabolize substrates added to the perfusion media.

Micro-organ arrays have also been treated with small molecules added to the perfusion media that include the transcription of metabolic enzymes. Higher levels of enzyme derived metabolite production have been observed concomitant with such treatment. This demonstrates high levels of tissue and cellular differentiation as well as maintenance of multiple cellular functions. For example, in order for the induced enzymes to be active, they must be combined with the appropriate prosthetic heme group and the resulting holoenzymes must then localize to the appropriate region of the cell. Thus, the observed elevated activity in response to inducing agents added to the perfusion media demonstrates that the cells in the micro-organ arrays have intact nuclear receptors, functional transcriptional and translational machinery, and biosynthetic activity for heme production.

EXAMPLE 5

Two-Photon Deep Tissue In Vivo Imaging Based on NAD(P)H Fluorescence

The capability of two-photon microscopy has been demonstrated by imaging deep tissue structure of in vivo human skin (Masters, et al., *Biophys. J.* 72:2405–12 (1996)). A Ti-Sapphire laser is tuned to 730 nm with an average power of about 10 to 20 mW. No extrinsic fluorescent labeling is required. Fluorescence contrast is obtained by exciting cellular endogenous chromophores primarily consisting of β-nicotinamide-adenine dinucleotide phosphate (NAD(P)H). The production of NAD(P)H is associated with the cellular metabolism and the intracellular redox state. Typically, a higher metabolic rate generates a higher concentration of NAD(P)H and produces brighter images.

Two photon microscopy was performed on human skin in vivo. The x-z and y-z planes of the reconstructed volume from the two-photon data were evaluated, and showed a brightly fluorescent layer at the top which corresponds to the stratum corneum, and a second bright layer about 100 $\mu$m below the skin's surface with an "egg carton" like morphology which most likely corresponds to the basal cell layer at the dermal-epidermal junction. The higher fluorescence from this layer correlated well with the high activity level of the basal cells. Good correlation between the two-photon results and the known skin physiology is observed using either scanning electron microscopy (SEM) or confocal microscopy.

EXAMPLE 6

Behavior of 3D Co-Cultures in Reactor Prototype I

An initial reactor configuration included a perfusion circuit in which medium maintained in a single reservoir was pumped through an oxygenator, through the chip/microarray, and then returned to the reservoir. Chips were placed in a stainless steel filter-holder (13 mm, Millipore). An initial chip design included 73 rounded-corner rectangular channels with dimensions 200 $\mu$m×200 $\mu$m, 100 $\mu$m×400 $\mu$m, or 200 $\mu$m×400 $\mu$m all 150–200 $\mu$m deep. A macroporous PTFE filter was thermally bonded to the chip array to retain cells in the channels. Culture medium was pumped via a peristaltic pump through silicone tubing to perfuse the cells and the entire circuit was maintained in a humidified $CO_2$ incubator for appropriate gas exchange.

The seeding and culture protocol used with this configuration is shown in FIGS. 14A–14C, which illustrates the configuration of the flow chamber for Prototype I. Cells (FIG. 14A) are seeded in the chamber under forced convection (FIG. 14B). The upper part of the chamber is then removed so that the cells can be maintained in 3D static culture in a $CO_2$ incubator for 24–48 hrs (FIG. 14C). The chamber then is reassembled for perfusion culture.

In initial experiments, it was found that initiating perfusion at physiological perfusion rates (30–50 $\mu$l/min) immediately after cell seeding compressed the cells in the channels, causing significant back pressure and occasionally causing the chips to crack. Cells were therefore cultured for 24–48 hrs. in static culture before initiating perfusion. Static culture allowed cell reorganization and morphogenesis into structures which could be readily perfused.

The rate of albumin secretion, a specific differentiated function of hepatocytes which is rapidly lost under standard culture conditions (e.g., monolayer cultures of pure hepatocytes), was used as a means of assessment of the appropriate static culture period for these cell-scaffold constructs. Primary rat hepatocytes and bovine aortic endothelial cells (each at $10^5$/ml cell medium) were seeded via syringe injection into scaffolds with channel sizes of 200 $\mu$m×200 $\mu$m, 100 $\mu$m×400 $\mu$m, or 200 $\mu$m×400 $\mu$m (FIG. 14A). Following a static culture period of 24–48 hr. the cell-scaffold constructs were perfused with culture medium at a rate of 30 $\mu$l/min. After an initial perfusion period of 30 min., the effluent was collected in two consecutive 900 $\mu$l (30 min.) samples.

For comparative analysis, these cells also were seeded onto 35 mm petri dishes coated with 3 $\mu$g/ml type I collagen (each at $3\times10^4$/cm$^2$ surface area). During the scaffold perfusion period, these dishes were provided with 2 ml fresh medium and cultured for approximately 2 hrs., after which the medium was collected.

Figure 15A:
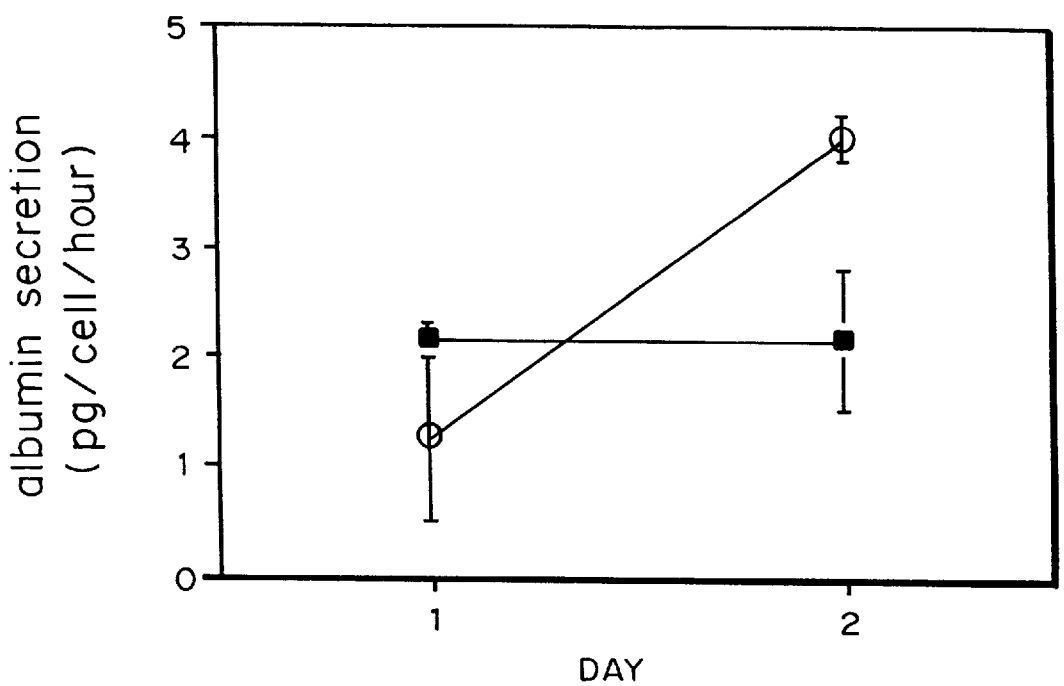
FIGS. 15A and 15B are graphs showing albumin secretion from perfused cell-scaffold constructs over time.

Medium samples were analyzed for rat albumin and normalized on a per cell basis (cell number quantified by bis-benzamide DNA analysis/albumin measured by). Results are shown in FIG. 15A. It is clear from this analysis that the perfused scaffolds exhibit significantly increased levels of albumin secretion after 48 hrs. static culture when compared with similar data after 24 hrs. static culture. Furthermore, the 48 hr. static culture scaffolds clearly secrete higher levels of albumin than petri dish cultures. These data suggest that the required period for cellular organization, structure formation, etc. is likely to be at least two days, and that such behavior does not take place under standard in vitro conditions (i.e., petri dishes).

In order to determine the ability of these scaffolds to sustain albumin secretion over more extended periods of time in the flow configuration of Prototype I, cells were seeded onto 200 $\mu$m×400 $\mu$m scaffolds as described previously and cultured under static conditions for 48 hrs. The scaffolds were then perfused with culture medium at 15 $\mu$l/min. for 330 min. After 30 min. initial perfusion the effluent was collected from each scaffold in five consecutive 900 $\mu$l (60 min.) samples.

Figure 15B:
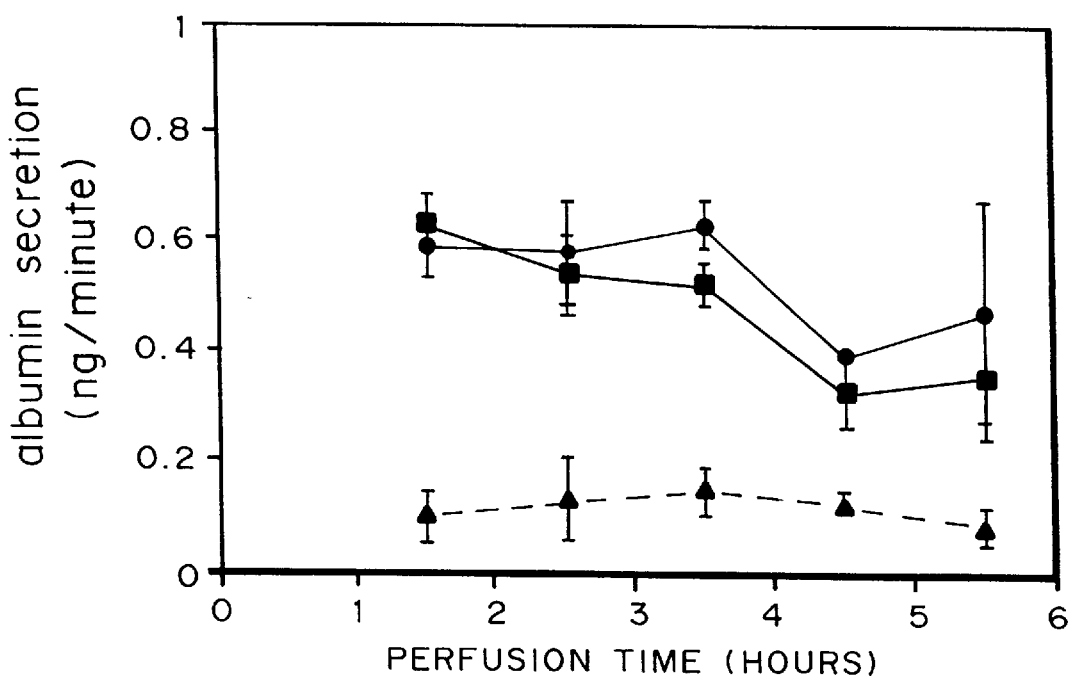

Results for three separate scaffolds are shown in FIG. 15B and suggest that these culture systems are able to support stable function for several hours but that significant scaffold—scaffold variability exists in the efficiency of seeding using the configuration in Prototype I.

EXAMPLE 7

Cross Flow Bioreactor

A cross-flow bioreactor was developed as described above and tested. Two fabrication methods were used. In the first fabrication route, the microchannels were microfabricated in silicon while the housing of the bioreactor was machined in stainless steel using standard machining. This design was used for the initial proof-of-the-principle laboratory testing. The second fabrication route incorporating anodic bonding provided means for large volume production of bioreactors.

Prototype I presented several operational problems. Uniform seeding was difficult and the nutrient concentrations (particularly oxygen) at the outlet could not be controlled independently of the perfusion rate.

Initial testing of the Prototype II system was performed with a variety of channel sizes (100 $\mu$m×250 $\mu$m, 100 $\mu$m×400 $\mu$m, 200 $\mu$m×200 $\mu$m×200 $\mu$m×400 $\mu$m). Culture medium (without cells) was recirculated independently through the upper and lower chambers at flowrates of 0.5–5 ml/min. In each instance, the reservoir feeding the upper chamber gradually decreased in volume while the reservoir feeding the lower chamber gradually increased in volume. These observations indicate that the hydrostatic pressure induced by the difference in height between the upper and lower chambers is sufficient to drive flow through the channels of the scaffold.

Initial studies of cell seeding in these reactor systems focused on using the existing hydrostatic pressure to guide cells into the scaffolds and provide perfusion flow. A solution of 5×10$^4$ primary rat hepatocytes and rat lung microvessel endothelial cells/ml was recirculated through the upper chamber with a peristaltic pump at a rate of approximately 1 ml/min. The cells were stirred at approximately 60 rpm in order to maintain the cells in suspension. Culture medium without cells was pumped through the lower reservoir at the same rate. Following a 4 hr seeding period, the upper chamber reservoir was replaced with cell-free culture medium. Perfusion flow was measured to be 20–40 $\mu$l/min. during cell seeding, and less than 10 $\mu$l/min. during the subsequent culture period. The system was then maintained for a period of 36 to 72 hr. and analyzed for cell engraftment using both phase contrast and two-photon microscopy. These techniques indicate that a large percentage of channels were observed to achieve a "tissue-density" using these seeding methods. In order to facilitate endothelial cell visualization with fluorescence microscopy, the cells were labeled with 5 $\mu$M Cell Tracker Green (Molecular Probes, Eugene, Oreg.).

The scaffold providing support for cell attachment and growth, as well as perfusion with nutrient and oxygen, is made out of silicon using a highly anisotropical deep reactive ion etching. The same etch through process employed to form microchannels also is used to cut the silicon wafer into individual disks without increasing the number of processing steps. Dicing the wafer into individual devices is thereby eliminated. This approach offers high flexibility, but its machining (a serial process) is costly. Alternatively, the cost of the perfusion bioreactor can be significantly reduced by using batch microfabrication techniques. These parallel techniques can yield inexpensive and disposable cartridge-like bioreactors. In one approach, these bioreactors can be built from silicon and glass wafers bonded together. For example, scaffolds with microchannels and perforated or porous screens can be microfabricated in a silicon wafer. The microchannels can be encapsulated by anodically bonding Pyrex (e.g. 7740) borosilicate wafers to the upper and lower surfaces of the silicon wafer (Wallis & Pomerantz, *J. Appl. Physics* 40: 3946 (1969)). Besides encapsulation, the top Pyrex wafer provides the same functions as the optically transparent disk described above. The bottom Pyrex wafer allows backside illumination of the microchannels, if necessary. Bonding can be accomplished on a hot plate in atmosphere or vacuum at temperatures and voltages typically between 180 and 500° C. and 200 to 1000V, respectively (Madou, *Fundamentals of Microfabrication* (CRC Press 1997)). A pressure usually is applied to force the wafers together during bonding. The coefficients of thermal expansion of silicon and Pyrex are closely matched. This is critical not only for the bonding process but also for rapid cryopreservation of tissues structures. Prior to anodic bonding, large conducting channels parallel to the wafer surface can be etched in Pyrex, which can be done, for example, in HF solution. These channels can be coupled to the outer environment by etched or ultrasonically (or laser) drilled holes. The aniodic bonding technique will preserve the features both in silicon and Pyrex. Since features in both silicon and Pyrex are present, precise alignment of the silicon and Pyrex wafers is mandatory. This task can be accomplished, for example, using an Electronic Visions/ Aligner Bonder (available in Microtechnology Technology Laboratories at the Massachusetts Institute of Technology). After bonding, the stack of Pyrex and silicon wafers can be diced into individual die. Depending on the application, the die can contain a desirable number of completely isolated microchannel arrays, each array having its own input and output. Therefore, an array of bioreactors can be fabricated on a single chip.

Design Parameters

Parameters of the reactor system have been designed to be physiologically relevant. In the absence of convective transport, the diffusion distance of oxygen in tissue was bathed in cell medium to be approximately 150 $\mu$m. Oxygenation from two sides of the tissue (as in the cross-flow reactor) allows for at least 300 $\mu$m of tissue to be penetrated.

Blood flow in the liver is approximately 1 ml/min./g tissue (Arias et al., eds., *The Liver* (Raven Press, New York, N.Y. 1988)). Performing an oxygen mass balance on the cells in the reactor system, assuming that these cells consume oxygen at a rate similar to that of in vivo tissue and neglecting the role of oxygen diffusion from the surface of the tissue, this flowrate is found to be approximately 9×10$^{-8}$ ml/cell/min. Much of this increased flow requirement of the perfused scaffold compared with in vivo liver cells is likely due to the decreased oxygen carrying capacity of cell medium compared with blood (about 1:4). Factoring in the diffusion distance of oxygen from the surface of the scaffold would also reduce the calculated requirement. The total medium flowrate in the sinusoids present in the system can nonetheless be reduced to more physiological levels by decreasing the scaffold thickness if necessary (i.e., decreasing the length of each "acinus"). For a 300 $\mu$m scaffold the maximum flowrate requirements are calculated to be in the range of 1 to 10 $\mu$l/min.

The reported pressure drop across sinusoids in vivo is typically about 1 to 2 mm Hg (Arias, et al.; Lautt, et al., *Drug Metabolism Rev.* 29:369–95 (1997)). Assuming that each channel in the perfused scaffold has at least one "capillary", the pressure drop can be calculated as a function of flowrate. Based on the previous analysis, the pressure drop present in the system would be expected to be less than 0.2 to 2 mm Hg.

EXAMPLE 8

Assays for Chemical Toxins

An essential first step in evaluating toxin response is determining the viability of cellular metabolic pathways. For many xenobiotic toxins, biotransformation is required to yield the ultimate toxic species. Frequently, the same classes of metabolic enzymes responsible for the normal metabolism of endogenous and exogenous compounds carry out this "bioactivation" of xenobiotics to toxins. The reactions catalyzed by these xenobiotic metabolizing enzymes traditionally are divided into two groups: phase I biotransformations and phase II biotransformations. Phase I reactions involve the unveiling or introduction of functionality, typically through hydrolysis, reduction or oxidation. Phase II biotransformations are characterized by conjugation of the xenobiotic with a hydrophilic cofactor such as an amino acid or sugar. The hepatotoxin aflatoxin illustrates this process as it undergoes epoxidation (phase I) followed by conjugation with the tri-peptide glutathione (phase II). In this case, the phase I reaction produces the bioactivated toxin and the phase II reaction inactivates this toxic species.

By far, the most important mammalian phase I enzymes are the cytochrome P450s (P450). These enzymes constitute a family of constitutively and/or inductibly expressed haemoproteins derived from multiple genes that catalyze the hydroxylation, dealkylation, and/or oxidation of a wide array of substrates. Frequently, a P450 is involved in the first step of bioactivation of a xenobiotic to a toxic species (i.e., P450 3A4 is the human P450 isozyme responsible for the epoxidation of aflatoxin). The expression and activity levels of the various P450s in hepatocytes are key indicators of the differentiated status of these cells in primary culture.

Bioreactor constructs using an assay that measures the activity of one representative P450 isozyme, cytochrome P450 1A1, was evaluated. This enzyme is present in all mammalian species and is highly inducible by polycyclic aromatic hydrocarbons as well as other agents. 7-Ethoxyresorufin is a selective substrate of rat P450 1A1 which catalyzes its de-ethylation to the highly fluorescent resorufin. Subsequent to P450 1A1 catalyzed de-ethylation, resorufin can be exported from the cell or undergo phase II conjugation. There are two possible phase II conjugation products resulting from the enzyme catalyzed addition of sulfate or glucoronic acid to the 7-hydroxyl group of resorufin. Thus, from this assay one can quantitatively determine the activity of P450 1A1 and the phase II conjugation enzymes. One also can qualitatively evaluate cell viability, hepatocyte uptake of compounds introduced into the perfusion media, and the effects of flow rate or reactor volumes on rates of xenobiotic biotransformation.

The 7-ethoxyresorufin O-dealkylation (EROD) assay involved dissolving the substrate into the chemically defined media (final concentration of 10–20 $\mu$M) and perfusing it through the tissue array. The effluent was collected in sequential fractions which then were analyzed by fluorescence detection for the presence of resorufin. Total conversion within each fraction was determined by incubating an aliquot from the fraction with enzymes that hydrolyze the phase II conjugates of resorufin back to the free alcohol. Comparison of this value to the value obtained without hydrolysis of phase II conjugates provided a measure of the amount of resorufin formed that undergoes phase II conjugation.

Experiments were conducted in the Prototype I forced flow reactor system. After a period of static culture at 37° C. and 5% $CO_2$, the bioreactor was reassembled and placed in-line with the perfusion circuit. Initial studies were conducted 14–20 hrs after seeding the silicon scaffolds with hepatocytes and endothelial cells. While some EROD activity could be observed, the levels were much lower (about $1/10^{th}$) than those of the controls (hepatocytes and endothelial cells plated on Type I collagen coated petri dishes). Additionally, there was a high rate of chip failure that could be linked to the excessive back pressure which developed during perfusion. These observations suggested that significant cell loading into the channels of the silicon chips was obtained (also confirmed by phase contrast microscopy and cell number analysis after removing the chips from the housing), but that the cells had not yet reorganized to produce flow channels. Therefore, the period of static culture prior to introducing the chips to perfusion culture was extended.

Figure 17:
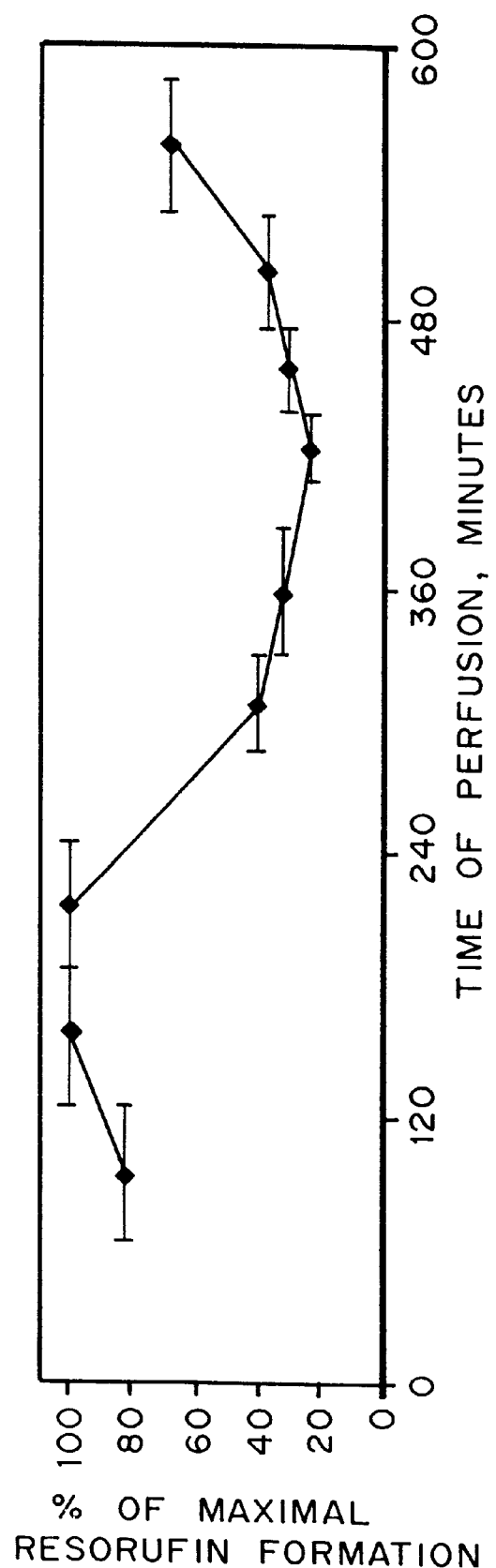
FIG. 17 is a graph of the EROD activity of the perfused bioreactor, graphing percent of maximal resorufin formation over time of perfusion in minutes.

FIG. 17 shows the results obtained from a bioreactor chip that was left in static culture for about 2.5 days with daily media changes prior to its introduction to perfusion culture. Perfusion of the bioreactor was initiated at t=0 min with chemically defined media containing ethoxyresorufin (10 $\mu$M). At t=240 min, the media was switched for media containing both ethoxyresorufin (10 $\mu$M) and the P450 1A1 inhibitor, naphthoflavone, (20 $\mu$M) until t=385 min when the media without inhibitor was returned. This extended period of static culture allowed the cells more time for reorganization and channel formation and led to a bioreactor without significant back pressure during perfusion and EROD activity comparable to the control cells in petri dishes. In this case, the chip was perfused with media containing ethoxyresorufin in the absence of a P450 1A1 inhibitor (t=0–240 minutes), in the presence of inhibitor (t=240–385 minutes) and then again in the absence of inhibitor (t=385–585 minutes). The time delay associated with reaching steady state after each addition reflects the length of time needed to flush the upper and lower chambers of the reactor housing ($V_{upper}$=0.45 ml and $V_{lower}$=0.15 ml).

This experiment demonstrated that the tissue arrays in the bioreactor readily metabolize compounds introduced into the perfusion media and achieve a steady state level of metabolite formation. Further, the enzyme activity was inhibited by the inclusion of a reversible inhibitor to the media and then recovered when the inhibitor was removed (this experiment was not further continued to observe the eventual return to steady state levels of resorufin production). Importantly, the cells in this bioreactor were responding to their environment and actively metabolizing substrate for nearly ten hours before the perfusion was halted.

A parallel experiment was run with a second bioreactor that had been treated with media containing 3-methylcholanthrene (a known P450 1A1 inducer) for its final 24 hours in static culture. This bioreactor showed a similar response curve as in FIG. 17, but its absolute level of resorufin formation was increased approximately five fold (calculated as attomoles resorufin formed per minute per hepatocyte) which was comparable to the increase observed with control cells (three to four fold increase under comparable exposure conditions). As 3-methylcholanthrene is a transcriptional inducer of P450 1A1, the cellular response to this agent demonstrated the viability of numerous cellular systems. For example, in order for the induced enzyme to be active, it must be combined with its prosthetic heme group and the holoenzyme must then localize to the endoplasmic reticulum. Thus, the observed elevated activity demonstrated that the cells in the bioreactors have intact nuclear receptors, functional transcriptional and translational machinery, and biosynthetic activity for heme production.

EXAMPLE 9

Development of Readouts for Viral Infection

Constructs for fluorescent readout were examined. The fluorescent indicator evaluated in this experiment was CCF- 2/AM. CCF-2/AM enters a cell, is esterized so it cannot leave the cell, and via FRET fluoresces a green color on excitation at 409 nm (coumarin-fluorescein transfer). In the presence of beta lacatamase, CCF-2 is split into a fluorescein and a coumarin, which fluoresces blue under excitation at 409 nm. As a result, the presence of beta-lacatamase can be determined by loading a cell with CCF-2/AM, and observing the blue-green ratio under excitation at 409 nm.

These chemicals have been tested in CHO cells (because of high transfection efficiency) with success, and it has also been verified that the Topaz GFP (green fluorescent protein) and beta-lacatamase positive cells (the blue cells post loading with CCF-2/AM) are well-correlated. Thus, there should be good co-transfection rates with the cationic lipid techniques.

These chemicals also were tested in human aortic smooth muscle cells (SMCs) and endothelial cells. Beta-lactamase gene expression was driven by the viral SV-40 promoter. Cells were loaded with CCF-2/AM and viewed with a fluorescent microscope (Olympus BX60) and a triple pass emission filter (RGB), excited with a UV/violet filter (400/15 nm). The presence of beta-lactamase activity was demonstrated by increased levels of blue fluorescence as seen by a triple pass filter.

Dual photon techniques have been used to establish quantitative detection of promoter-driven fluorescent reporter activity. This required additional filter optimization, but demonstrated the ability to detect cleavage of the CCF2/AM substrate. In addition, cells with promoter-driven green fluorescent protein and detected promoter activity have been successfully transfected. These tools can be adapted for fluorescent detection for quantitating gene expression.

EXAMPLE 10

Biotoxin Interactions with Hepatic Cells

Representative toxins were investigated, focusing initially on toxin produced by Helicobacter species. *H. pylori*, the bacterium associated with stomach ulcers and cancers in humans, produces a toxin which creates vacuoles in cultured cells and thus the toxin is called the vacuolating (Vac) toxin. Other Helicobacter species are believed present in rodents, including *H. hepaticus* which infects mice and *H. bilis* which infects rats, also produce similar Vac toxins. Thus, the interactions of toxins produced by these strains with mouse and rat hepatocytes were characterized. It is important to understand how these toxins interact with rodent cells not only as models for the human case, but also because these toxins are believed to be endogenously present and unrecognized in cell cultures, affecting results in subtle ways unreported in the literature.

Toxin Interactions with Mouse Liver Cell Line CCL 9.1

*H. hepaticus* infects mice and is found in the GI tract and liver. A toxin extract from *H. hepaticus* cultures was prepared by culturing *H. hepaticus* in standard culture medium, spinning the culture to form a pellet, resuspending in phosphate buffered saline (PBS) for 3 hours at 37° C. followed by overnight at 4° C., then pelleting the cells and removing the supernatant containing the toxin. This partially purified material exhibits cytotoxic activity on monolayers of cultured hepatic cell lines.

The mouse liver cell line CCL 9.1, like many cell types, typically exhibits vacuoles under standard culture conditions. These vacuoles are visible as clear areas in the cytoplasm when cells are viewed with phase contrast optical microscopy. A standard assay for the pH of vacuoles is neutral red staining. Neutral red is a membrane-permanent amine which accumulates in acidic vacuoles where it is protonated, thus staining acidic vacuoles red. CCL 9.1 cells cultured under standard conditions and incubated with neutral red do no exhibit staining of vacuoles. In contrast, CCL 9.1 cells cultured under standard conditions and subjected to the *H. hepaticus* toxin extract exhibit intense red staining of vacuoles, indicating that the toxin decreases the pH of the vacuoles by some mechanism.

Endogenous Vacuoles and *H. hepaticus*- and *H. bilis*-Induced Vacuoles in Primary Rat Hepatocytes Primary rat hepatocytes typically exhibit at least some level of vacuole formation under standard culture conditions, although the number of vacuoles per cell can be highly variable from isolation to isolation. It has generally been observed that cultures with an unusually large number of vacuoles generally perform atypically—usually poorer—than cultures with few vacuoles. To investigate this, cultures exhibiting abnormally high vacuole formation were stained with neutral red on the second day of culture. These cultures exhibited strong staining. These results suggested the primary rat cells are endogenously infected with a toxin-secreting Helicobacter strain. To investigate this further, hepatocyte isolations were performed on a pair of rats, fecal and cecum samples from these same animals were examined, and helicobacter culture isolations and direct DNA extraction for PCR analysis of specific helicobacter strains in these samples were conducted. PCR results with generic helicobacter primers showed positive results with both rats. Interestingly, although the PCR analysis of the GI tissue samples indicated infection with both *H. bilis* and *H. hepaticus*, the cell cultures exhibited few vacuoles, and the vacuoles present did not stain with neutral red on day 5 of culture. Addition of 25 µl of either *H. hepaticus* toxin or *H. bilis* toxin (prepared as described above for *H. hepaticus* toxin) to the 2 ml culture media (35 mm plates) resulted in some observable cell death and formation of vacuoles which stained with neutral red, consistent with results for CCL 9.1. These results indicate that the Helicobacter toxins interact with mouse cell lines and primary hepatocytes in a similar manner.

Strikingly, the control cultures, which did not exhibit staining on Day 5, stained moderately on Day 6, suggesting that a latent infection had blossomed over the course of the 6-day incubation. This finding is consistent with the PCR results indicating infection by both *H. bilis* and *H. hepaticus* in the rats from which the cells were obtained. The mode of infection of the cultures may arise from endogenous presence of the bacteria in the liver, as has been documented for *H. hepaticus* in mice, or it may arise via contamination by GI fluid during the cell isolation.

EXAMPLE 11

Spectroscopy and Microscopy Instrumentation

Fabrication of a prototype tissue reactor capable of directly monitoring tissue status is an essential step in optimizing the seeding and maintenance of cells in the channels. The development of the tissue sensor requires the optimization of a large number of parameters such as the silicon scaffold surface chemistry, the scaffold channel geometry, and the hydrodynamic parameters related to the perfusion medium. The reactor scaffold housing design is constrained by three criteria. First, the chamber must be compatible with a variety of microfabricated silicon scaffold designs. Second, the chamber must allow easy control of the perfusion condition. (In particular, the perfusion rates of the medium above and below the silicon scaffold have to be adjustable individually, and the hydrodynamic pressure and flow rate across the scaffold need to be specified.) Third, for a typical silicon scaffold with thickness on the order of 100 to 300 μm, the chamber has to be compatible with optical microscopy observation throughout the thickness of its channels.

Based on these three requirements, a cross-flow reactor was designed, as depicted schematically in FIG. 2 and shown in detail in FIG. 16. The reactor features top and bottom compartments. When completely assembled, these two compartments are separated by the silicon scaffold. The design is flexible and can accommodate any 1" diameter silicon wafer with thickness from 100 to 300 μm. Both the top and bottom compartments feature independent inlets and outlets for the perfusion medium, which allows independent control of medium flow rate at each compartment. The pressure differential across the compartment depends on these flow rates as well as the channel design of the silicon scaffold. Finally, the design of the chamber is optimized for high resolution optical microscopy observation. In order to achieve sub-micron resolution imaging, high numerical aperture objectives are needed. A major limitation of high numerical aperture objectives is their short working distances. The top window of the chamber is a standard cover glass. The chamber was designed for a chosen set of objectives (Zeiss, Achroplan water immersion series objectives 20X, 0.4 N.A., 1.2 mm W.D.; 63X, 0.9 N.A. 1.46 mm; 100X, 1.0 N.A., 0.97 mm), which were chosen to simultaneous optimize three constraints: high numerical aperture, large viewing area, and long working distance. The reactor dimension was optimized such that this set of objectives can view through both the top chamber and the full thickness of the silicon scaffold.

Optical Characterization of the Tissue Culture Reactor

The reactor design was verified to be compatible with high resolution optical microscopy. The suitability of the reactor design for optical microscopy was tested using a two-photon microscope. As a first experiment, co-culture of hepatocytes and endothelial cells were grown in the tissue culture reactor using a silicon wafer with a thickness of 150 mm (the detail of cell culture procedures and results are presented elsewhere). The hepatocytes were unlabeled with Cell Tracker Green dye (Molecular Probes, Eugene, Oreg.). The hepatocytes can be easily visualized by their autofluorescence, due to their high NAD(P)H content. The co-culture was studied using two-photon microscope using a Zeiss Achroplan 63× objective. The excitation wavelength was set at 780 nm. The hepatocytes and epithelial cell co-culture were clearly visualized in the silicon scaffold channel. The cells in the channel were found to be visualized in 3D with excellent depth discrimination. Sequential optical sections (10 μm) of a bridging structure across a 100×400 μm channel and a 3D reconstruction of the images indicate that the cells are bridging across the channels yet leaving significant open volume. In addition, many hepatocytes were not covered by endothelial cells, in contrast to previous results from 2D and 3D co-cultures. In these preliminary experiments, most channels were filled with only 1–2 layers of cells, but the cells occupied a significant fraction of the cross sectional area.

Design of a Dedicated Optical Spectroscopic System to Characterize Tissue State

Figure 18:
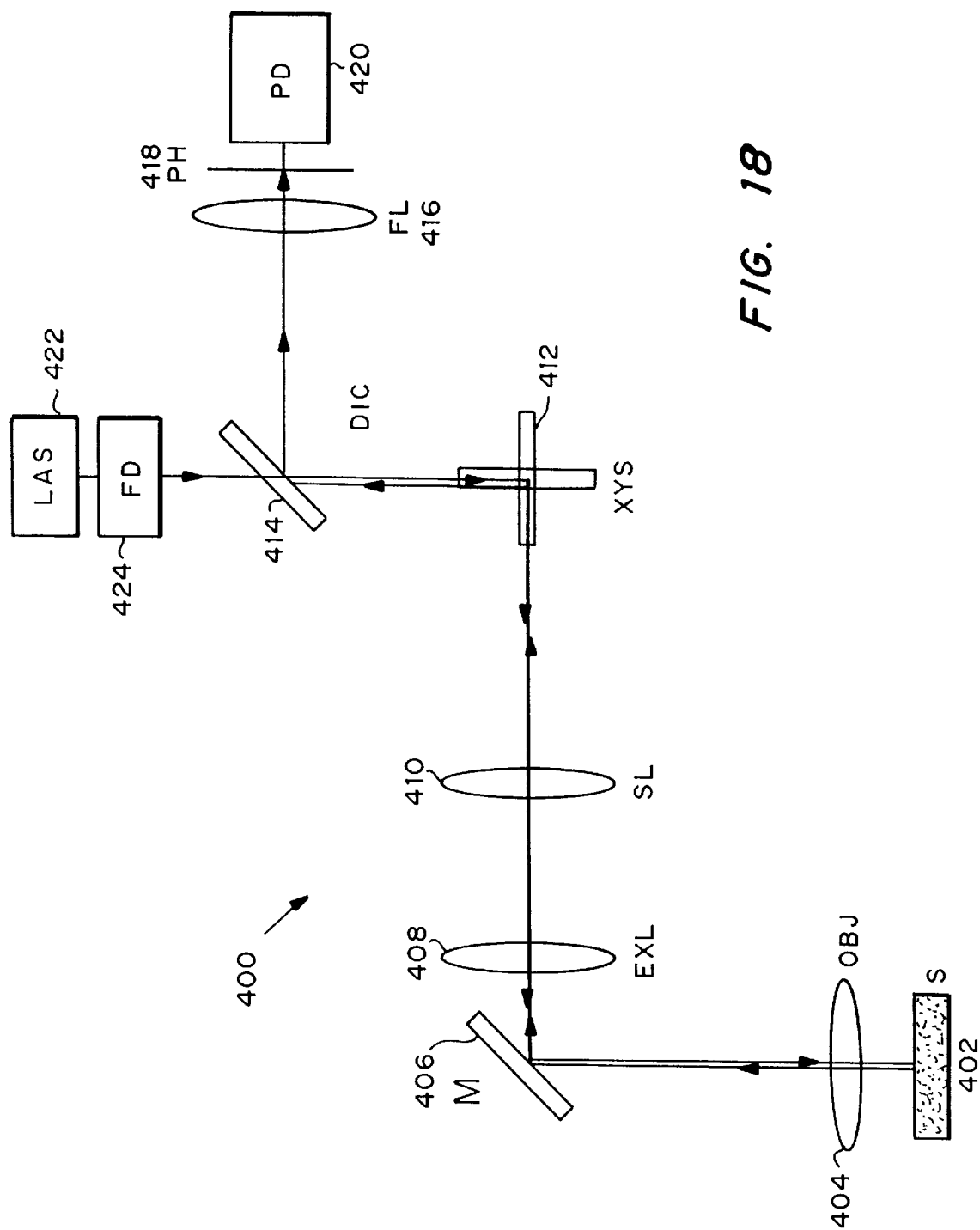
FIG. 18 is a schematic of a sampling system.

Since the tissue channel can be up to a few hundreds of micrometers thick, tissue morphology generally cannot be resolved by viewing from the surface alone. Also, metabolite distribution can vary along the channel. Therefore, tissue morphological and biochemical state should be monitored at different depths. This requirement dictates that the optical detection system must have depth discrimination capability. Accordingly, a general purpose confocal microscopy and spectroscopy system were developed, which should provide rapid determination of tissue morphology and biochemistry and optimizing optical readout probes such as fluorescent reporter genes. A design of this generation confocal detection system 400 is presented in FIG. 18, wherein S 402 is the sample, OBJ 404 is the imaging objective, M 406 is a mirror, EXL 408 is the excitation tube lens, SL 410 is the scan lens, XYS 412 is the x-y scanner, DIC 314 is the dichoric mirror, FL 416 is the focusing lens, PH 418 is the pinhole aperture, PD 420 is the photodetector, LAS 422 is the Ti-Sapphire laser system, and FD 424 is the frequency doubler.

The light source used in the frequency-doubled output of a Ti-Sapphire laser system (Spectra Physics, Mountain View, Calif.). The infrared light emitted by the Ti-Sapphire laser is converted to UV/blue/green light using a frequency doubler (Inrad, Northvale, N.J.). While the Ti-Sapphire laser system is not suitable for field implementation, its tunability facilitates economical exploration of wavelengths ranges from 350 nm to 500 nm, and therefore optimization of the experimental condition for a large variety of fluorescent reporters, such as NAD(P)H, Indo I, GFP, and CCF2. It was verified that up to 100 mW of 370 nm radiation can be generated from the frequency doubler. The spatial of the frequency doubled light was excellent and is well suited for high resolution confocal imaging.

The excitation light was reflected by a dichoric mirror into a galvanometer driven x-y scanner (Cambridge Technology, Cambridge, Mass.). The dichoric mirrors were custom-made long pass filters (Chroma Technology Inc., Brattleboro, Vt.). Microscopic images were generated by raster scanning the x-y mirrors. The excitation light was directed by the x-y scanner into a modified epiluminescence light path of a high throughput optical microscope (Axioscope I, Zeiss, Thornwood, N.Y.). The scan lens was positioned such that the x-y scanner was at its eye-point while the field aperture plane was at its focal point. Since the objectives are infinity-corrected, a tube lens was positioned to re-collimate the excitation light. The scan lens and the tube lens functioned together as a beam expander which over-filled the back aperture of the objective lens. The excitation light was reflected by a broad band mirror to the objective. The microscope field of view was about 50–100 mm on a side, and the typical frame rate was about two seconds. In order to address the different channels over the 1.25 cm diameter silicon scaffold, the tissue chamber was mounted on a x-y stage translator (Prior Systems, Rockland, Mass.) which allowed sample placement over a range of 5 cm with a precision better than 1 mm. The axial imaging plane was adjusted by two positioning systems operating in tandem. A piezo-driven objective position with a range of 100 μm provide rapid z-positioning (PI Inc., Auburn, Mass.) while a stepper motor driven stage position allowed convenient gross alignment.

The fluorescence emission was collected by the same objective and transmitted backward through the excitation beam path. The fluorescence emission was descanned as it exited the microscope system through the x-y scanner. The fluorescence was deflected by the dichoric mirror toward the emission path. An additional barrier filter was used to further attenuate the scattered excitation light. The fluorescence signal at each pixel was detected by a R5600-P PMT (Hamamatsu, Bridgewater, N.J.) which is a compact module with high quantum efficiency and low noise. The signal was conditioned by a low noise pre-amplifier and a single photon discriminator. The resultant digital signal was acquired by a custom interface card and was recorded by the data acquisition computer.

Modifications and variations of the methods and apparati described herein will be obvious to those skilled in the art from the foregoing detailed description. Such modifications and variations are intended to come within the scope of the appended claims.

We claim:

1. An apparatus comprising
   a) a matrix comprising one or more channels which support the viability of cells,
   b) endothelial cells within the channels of the matrix, and
   c) means for detecting changes in the cells or in compounds exposed to the cells,
   wherein the matrix allows perfusion of the cells with nutrients and oxygen sufficient to maintain the viability of the cells and the matrix allows formation of microvascular networks, wherein the nutrients are provided by culture medium which perfuses through the microvascular networks.

2. The apparatus of claim 1 wherein the matrix comprises a silicon chip with an array of open channels.

3. The apparatus of claim 2 wherein the channels have a depth of between 150 and 400 micrometers.

4. The apparatus of claim 1 wherein means for detecting changes in the cells or in compounds exposed to the cells comprises a miniaturized fiber optic system which provides single or multi-photon excitation to individual channels.

5. The apparatus of claim 1 wherein the channels are coated with a substance selected from the group consisting of peptides or proteins promoting cell adhesion on biocompatible polymers.

6. The apparatus of claim 1 wherein the matrix comprises a polymer with an array of open channels.

7. The apparatus of claim 1 wherein the matrix is prepared using a method selected from the group consisting of micromolding, electro-deposition machining, laser ablation, laser drilling, micromachining, wet etching, reactive ion etching, and embossing.

8. The apparatus of claim 1 wherein the matrix further comprises a bioactive agent.

9. The apparatus of claim 8 wherein the bioactive agent is selected from the group consisting of cell growth, differentiation, and migration modulators.

10. The apparatus of claim 1 wherein the means for detecting changes in the cells or in compounds exposed to the cells comprises sensors which detect changes in pH, oxygen levels, specific metabolites, or the presence or absence of an indicator molecule.

11. The apparatus of claim 1 further comprising cells selected from the group consisting of parenchymal cells which provide metabolic or organ function, nerve or nervous tissue, connective tissue, and undifferentiated cells, wherein the cells are attached to the endothelial cells within the channels of the matrix.

12. The apparatus of claim 11 wherein the undifferentiated cells are selected from the group consisting of embryonic cells, stem cells, and other precursor cells.

13. The apparatus of claim 1 wherein the cells are transgenic for one or more genes.

14. The apparatus of claim 1 wherein the surface of the channel walls is grooved or scalloped for controlling cell adhesion, spreading, morphogenesis, or function.

15. The apparatus of claim 1 which is suitable for cryopreservation of tissue structures.

16. The apparatus of claim 1 wherein the rate of cell perfusion is controllable via a flow of perfusate.

17. The apparatus of claim 1 wherein the flow is across at least one side of the channels or is forced through the channels.

18. The apparatus of claim 1 wherein the matrix comprises two or more independent perfusion circuits.

19. The apparatus of claim 18 wherein one circuit is above the channel and one circuit is below the channel.

20. The apparatus of claim 1 wherein the cells are attached within the channel.

21. The apparatus of claim 1 wherein the cells form aggregates or spheroids within the channel.

22. A method for screening drugs for biological activity, toxicity or teratogenicity comprising adding a drug to an apparatus which comprises:
   a) a matrix comprising one or more channels which support the viability of cells,
   b) cells forming microvascular networks within the channels of the matrix, and
   c) means for detecting changes in the cells or in compounds exposed to the cells,
   wherein the cells are perfused with nutrients and oxygen through the microvascular network sufficient to maintain the viability of the cells.

23. A method for propagating stem cells comprising:
   a) providing an apparatus which comprises:
      a matrix, which includes:
         i) one or more channels within the matrix,
         ii) endothelial cells within the channels of the matrix, and
         iii) means for detecting changes in the cells or in compounds exposed to the cells,
      wherein the matrix allows perfusion through the channels of the matrix of the cells with nutrients and oxygen sufficient to maintain the viability of the cells; and
   b) propagating the cells on the matrix.

24. The method of claim 23 further comprising adding a soluble compound to the medium which causes the stem cells to extravasate from the matrix.

25. The method of claim 24 wherein the compound is a chemotherapeutic agent.

26. The method of claim 24 further comprising harvesting the cells.

27. The method of claim 26 wherein the cells are harvested by collection on a filter.

28. A method for screening a compound for at least one activity under physiological conditions in a microarray comprising exposing cells in an apparatus, which comprises a matrix, which includes:
   i) one or more channels within the matrix,
   ii) endothelial cells within the channels of the matrix, and
   iii) means for detecting changes in the cells or in compounds exposed to the cells,
   wherein the cells form microvascular networks in the channels of the matrix and the channels allow perfusion of the cells with nutrients and oxygen sufficient to maintain the viability of the cells exposed to a compound to be tested and screened for at least one effect of the compound on the cells.

* * * * *

UNITED STATES PATENT AND TRADEMARK OFFICE
CERTIFICATE OF CORRECTION

PATENT NO.    : 6,197,575 B1
DATED         : March 6, 2001
INVENTOR(S)   : Linda Griffith et al.

It is certified that error appears in the above-identified patent and that said Letters Patent is hereby corrected as shown below:

<u>Column 1,</u>
Line 8, before "BACKGROUND OF THE INVENTION", insert the following:

-- STATEMENT REGARDING FEDERALLY SPONSORED RESEARCH OR DEVELOPMENT
    This invention was made with government support under grant number 9157321-BCS and EEC-9543790 awarded by the National Science Foundation. The government has certain rights in the invention. --

Signed and Sealed this

Eleventh Day of February, 2003

JAMES E. ROGAN
*Director of the United States Patent and Trademark Office*